(12) United States Patent
Biftu et al.

(10) Patent No.: US 6,420,392 B1
(45) Date of Patent: Jul. 16, 2002

(54) COMPOUNDS AND METHODS FOR THE TREATMENT OF CARDIOVASCULAR, INFLAMMATORY AND IMMUNE DISORDERS

(75) Inventors: Tesfaye Biftu, Westfield, NJ (US); Xiong Cai, Framingham, MA (US); Sajjat Hussoin, Lexington, MA (US); Gurmit Grewal, Waltham, MA (US); T Y Shen, Great Falls, VA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 08/669,371

(22) PCT Filed: Jan. 6, 1995

(86) PCT No.: PCT/US95/00060

§ 371 (c)(1), (2), (4) Date: Oct. 9, 1996

(87) PCT Pub. No.: WO95/18610

PCT Pub. Date: Jul. 13, 1995

Related U.S. Application Data

(63) Continuation-in-part of application No. 08/178,222, filed on Jan. 6, 1994, now Pat. No. 5,463,083.

(51) Int. Cl.$^7$ .................. A01N 43/06; C07D 401/00; C07D 409/00; C07D 307/02

(52) U.S. Cl. .................. 514/336; 514/438; 514/471; 514/473; 546/283; 546/284; 549/483; 549/484; 549/488; 549/491; 549/496; 549/497; 549/498; 549/499; 549/500; 549/501; 549/502

(58) Field of Search .................. 514/336, 438, 514/471, 473; 546/283, 284; 549/483, 484, 488, 491, 496, 497, 498, 499, 500, 501, 502

(56) References Cited

U.S. PATENT DOCUMENTS

| | | | |
|---|---|---|---|
| 2,690,988 A | 10/1954 | Jones et al. ............ 514/44 |
| 2,913,494 A | 11/1959 | Lobby .................. 564/283 |
| 2,956,062 A | 10/1960 | Lunsford .............. 564/283 |
| 3,038,004 A | 6/1962 | Copp et al. ............ 548/556 |
| 3,161,654 A | 12/1964 | Shen .................... 544/64 |
| 3,647,858 A | 3/1972 | Hinkley et al. ......... 514/916 |
| 3,654,349 A | 4/1972 | Shen et al. ............ 206/53 |
| 3,714,226 A | 1/1973 | Ruyle et al. ........... 514/825 |
| 4,166,452 A | 9/1979 | Generales, Jr. ........ 273/446 |
| 4,256,108 A | 3/1981 | Theeuwes ............. 128/260 |
| 4,265,874 A | 5/1981 | Bonsen et al. ......... 424/15 |
| 4,522,811 A | 6/1985 | Eppstein et al. ....... 514/2 |
| 4,539,332 A | 9/1985 | Biftu et al. ........... 514/461 |
| 4,595,693 A | 6/1986 | Biftu et al. ........... 514/513 |
| 4,604,407 A | 8/1986 | Haslanger et al. ..... 514/575 |
| 4,656,190 A | 4/1987 | Shen et al. ........... 514/529 |
| 4,757,084 A | 7/1988 | Biftu et al. ........... 514/438 |
| 4,841,968 A | 6/1989 | Dunn et al. ........... 128/332 |
| 4,845,129 A | 7/1989 | Anderson et al. ...... 514/600 |
| 4,871,756 A | 10/1989 | Gillard et al. ......... 514/381 |
| 4,873,259 A | 10/1989 | Summers, Jr. et al. .. 514/443 |
| 4,876,346 A | 10/1989 | Musser et al. ......... 546/172 |
| 4,891,363 A | 1/1990 | Nakamura et al. ...... 514/94 |
| 4,910,206 A | 3/1990 | Houlihan .............. 514/292 |
| 4,916,145 A | 4/1990 | Tilley et al. .......... 514/357 |
| 4,959,361 A | 9/1990 | Walser ................. 514/220 |
| 4,987,132 A | 1/1991 | Mase et al. ............ 514/252 |
| 4,992,428 A | 2/1991 | Houlihan et al. ....... 514/63 |
| 4,996,203 A | 2/1991 | Biftu et al. ........... 514/231.5 |
| 5,001,123 A | 3/1991 | Biftu et al. ........... 514/235.2 |
| 5,037,853 A | 8/1991 | Brooks et al. ......... 514/598 |
| 5,047,420 A | 9/1991 | Graham et al. ........ 514/484 |
| 5,110,831 A | 5/1992 | Magolda et al. ....... 514/645 |
| 5,112,848 A | 5/1992 | Brooks et al. ......... 514/424 |
| 5,169,854 A | 12/1992 | Brooks et al. ......... 514/314 |
| 5,175,183 A | 12/1992 | Brooks et al. ......... 514/438 |
| 5,183,818 A | 2/1993 | Brooks et al. ......... 514/231.5 |
| 5,187,192 A | 2/1993 | Brooks et al. ......... 514/510 |
| 5,234,950 A | 8/1993 | Edwards et al. ....... 514/473 |
| 5,244,896 A | 9/1993 | Borcherding et al. ... 514/258 |
| 5,288,751 A | 2/1994 | Brooks et al. ......... 514/438 |
| 5,326,787 A | 7/1994 | Brooks et al. ......... 514/507 |

(List continued on next page.)

FOREIGN PATENT DOCUMENTS

| | | |
|---|---|---|
| DE | 3701344 | 7/1987 |
| DE | 3724031 | 1/1988 |
| DE | 3724164 | 1/1988 |
| DE | 3936828 | 5/1990 |

(List continued on next page.)

OTHER PUBLICATIONS

Backvall, et al., "A Stereocontrolled Organopalladium Route to 2,5–Disubstituted Pyrrolidine Derivatives. Application to the Synthesis of a Venom Alkaloid of the Ant Species *Monomorium latinode*," *J. Org. Chem.*, 55:826–831 (1990).

(List continued on next page.)

*Primary Examiner*—John Kight
*Assistant Examiner*—Raymond Covington
(74) *Attorney, Agent, or Firm*—Peter F. Corless; Christine C. O'Day; Edwards & Angell, LLP

(57) ABSTRACT

2,5-Diaryl tetrahydrofurans, 2,5-diaryl tetrahydrothiophenes, 1,3-diaryl cyclopentanes are disclosed that reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i.e., by acting as both a PAF receptor antagonist and inhibitor of 5-lipoxygenase. Also disclosed is a method to treat disorders mediated by PAF and/or leukotrienes that includes administering an effective amount of one or more of the above-identified compounds or a pharmaceutically acceptable salt thereof, optionally in a pharmaceutically acceptable carrier, to a patient in need of such therapy.

11 Claims, No Drawings

U.S. PATENT DOCUMENTS

| | | | |
|---|---|---|---|
| 5,334,616 A | 8/1994 | Brooks et al. | 514/473 |
| 5,334,843 A | 8/1994 | Guthrie et al. | 250/486.1 |
| 5,358,938 A | 10/1994 | Cai et al. | 514/731.5 |
| 5,420,164 A | 5/1995 | Mishina et al. | 514/596 |
| 5,434,151 A | 7/1995 | Cai et al. | 514/231.5 |
| 5,463,083 A | 10/1995 | Biftu et al. | 549/71 |
| 5,530,141 A | 6/1996 | Shen et al. | 549/39 |
| 5,639,782 A | 6/1997 | Shen et al. | 514/440 |

FOREIGN PATENT DOCUMENTS

| | | |
|---|---|---|
| DE | 4006471 | 9/1990 |
| EP | 0 144 804 | 6/1985 |
| EP | 0 199 324 | 10/1986 |
| EP | 0 217 204 | 4/1987 |
| EP | 0 252 823 A1 | 1/1988 |
| EP | 0 257 921 | 3/1988 |
| EP | 0 319 947 A2 | 6/1989 |
| EP | 0 322 033 | 6/1989 |
| EP | 0 338 993 A1 | 10/1989 |
| EP | 0 365 089 A2 | 4/1990 |
| EP | 0 367 110 A1 | 5/1990 |
| EP | 0 388 309 A2 | 9/1990 |
| EP | 0 402 150 A1 | 12/1990 |
| EP | 0 402 151 | 12/1990 |
| EP | 0 402 155 | 12/1990 |
| EP | 0 402 156 | 12/1990 |
| EP | 0 416 609 | 3/1991 |
| EP | 0 617 032 | 9/1994 |
| GB | 2 197 650 | 5/1988 |
| GB | 2 233 974 | 1/1991 |
| GB | 2 263 109 | 7/1993 |
| WO | WO 90/12015 | 10/1909 |
| WO | WO 89/04299 | 3/1988 |
| WO | WO 91/17157 | 11/1991 |
| WO | WO 92/09566 | 6/1992 |
| WO | WO 92/13848 | 8/1992 |
| WO | WO 92/15294 | 9/1992 |
| WO | WO 93/01191 | 1/1993 |
| WO | WO 93/16075 | 8/1993 |
| WO | WO 94/01430 | 1/1994 |
| WO | WO 94/04537 | 3/1994 |
| WO | WO 94/06790 | 3/1994 |
| WO | WO 95/18610 | 7/1995 |
| WO | WO 96/00212 | 1/1996 |

OTHER PUBLICATIONS

Bartroli, J., "Design of Potent Linear PAF Antagonists," *J. Med. Chem.*, 34:3328–3334 (1991).

Biftu, T., et al., Abstr. of 6th Int. Conf. on Prostaglandins and Related Compounds, Florence, Italy, p. 302 (Jun. 3–6, 1986).

Biftu, T., et al., "Confirmation and Activity of Tetrahydrofuran Lignans and Analogues as Specific Platelet Activating Factor Antagonists," *J. Med. Chem.*, 29(10):1917–1921 (1986).

Bigi, et al., "Modificaton of the Nickl Reaction . A General Synthetic Approach to 2–Vinyl–2,3–Dihydrobenzofurans," *Tetrahedron*, 19(1):169–174 (1983).

Bowles, et al., A Convenient Preparation of Cyclic Ether Acetals Mediated by Trifluoroacetic Anhydride, *Synlett*, pp. 111–112 (1993).

Carcellar, E., et al., "4–Substituted 2–Alkoxytetrahydrofurans as Potent and Long–Lasting PAF Antagonists," *J. Med. Chem.*, 35(4):676–683 (1992).

Carter, et al., "5–Lipoxygenase Inhibitory Activity of Zileuton," *J. of Pharmacol. and Exp. Thera.*, 256(3);929–937 (1991).

Corey, E.J. et al., "Dual Binding Modes to the Receptor for Platelet Activating Factor (PAF) of Anti–PAF Trans–2, 5–Diarylfurans," *Tetrahedron Letters*, 29(24):2899–2902 (1988).

Crawley, G.C., "Methoxytetrahydropyrans. A New Series of Selective and Orally Potent 5–Lipoxygenase Inhibitors," *J. Med. Chem.*, 35(14):2600–2609 (1992).

Cusic and Robinson, "Autonomic Blocking Agents. II. Alkamine Esters and Their Quaternaries," Presented befor eht Medicinal Division of the American Chemical Society, Philadelphia, PA (Apr., 1950).

Danyoshi et al., "Pyrrolidine Derivatives as Inhibitors of Platelet Aggregation Induced by Platelet Activating Factor," *Chem. Pharm. Bull.*, 37(7):1969–1970 (1980).

Dess and Martin, "Readily Accesible 12–I–5' Oxidant for hte Conversion of Primary and Secondary Alcohols to Aldehydes and Ketones," *J. Org. Chem.* 48:4156–4158 (1983).

Erez, et al., "Narcotic Antagonistic Potency of Bivalent Ligands Which Contain Beta–Naltrexamine. Evidence for Bridging between Proximal Recognition Sites," *J. of Med. Chem.*, 25(7):847–849 (1982).

Feinmark, S. J., "Leukotriene, $C_4$ Biosynthesis During Polymorphonuclear Leukocyte–Vascular Cell Interactions," *Methods in Enzymology*, Murphy and Fitzpatrick, eds., Academic Press, Inc., Harcourt Brace Jovanovich, publishers, New York, NY, vol. 187, pp. 559–560 (1990).

Foye, (Editor) "Bioisosterism," *Principles of Med. Chem.*, Second Edition, pp. 80–81 (Lea & Febiger, Philadaelphia, 1981).

Glover and Sandler, "Trends in Pharmacological Sciences," *TIPS*, 10:1–3 (1989).

Goldstein, et al., "Dual Inhibitors of Platelet Activating Factor and 5–Lipoxygenase. I., 2,40Diaryl–1,3–dithiolanes," *Med. Chem. Res.*, 2:443–450 (1992).

Goldstein, et al., "Dual Inhibitors of Platelet Activating Factor and 5–Lipoxygenase. II. Novel 2,4–Diaryl–1,3–dithiolanes with Iron–Chelating Functionalities," *Med. Chem. Res.*, 2:451–456 (1992).

Graham, D.W., et al., "1,3–Diarylcyclopentanes: A New Class of Potent PAF Receptor Antagonists," 197th ACS National Meeting, Division of Medicinal Chemistry, poster No. 25, Dallas, Texas (Apr. 9–14, 1989).

Guthrie, R.W., et al., "Propenyl Carboxamide Derivatives As Antagonists of Platelet Activating Factor," *J. Med. Chem.*, 33:2856–2864 (1990).

Hwang, S., "Specific Receptors of Platelet–Activating Factor, Receptor Heterogeneity, and Signal Transduction Mechanisms," *J. Lipid Mediators*, 2:123–158 (1990).

Hwang, S., et al., "Trans–2, 5–bis–(3,4,5–trimethoxyphenyl)tetrahydrofuran," *Journal of Biological Chemistry*, 260(29):15639–15645 (1985).

Hwang, S., et al., "Biochemical and Pharmacological Charactgerization of L–659, 989: An Extremely Potent, Selective and Competitive Receptor Antagonist of Platelet–Activating Factor," *J. Pharmacol. Ther.*, 246(2):534–541 (1988).

Ikeda et al., "Preparation of Hydroxamic Acid and N–Hydroxyurea Derivatives and Their Use as Lipoxygenase Inhibitors," *Chemical Abstracts*, vol. 118, Abstract No. 59426 (1993).

Jamali, et al., "Enantioselective Aspects of Drug Action and Disposition: Therapeutic Pitfalls," *J. of Pharm. Sci.,* 78(9):695–715 (1989).

Kasuya, et al., "Hypotensive actions of some analogues of platelet–activating factor (PAF) with higher potencies than natural PAF," *Can. J. Physiol. Pharmcol.,* 62:457–459 (1984).

Katsuki and Sharpless, "The First Practical Method for Asymmetric Epoxidation," *J. Am. Chem. Soc.,* 102:5974–5976 (1980).

Lange, et al., "Stimulation of Rat Gastric Mucosal Leukotriene $C_4$ Formation by Ethanol and Effect of Gastric Protective Drugs," *Advances in Prostaglandin, Thromboxane, and Leukotriene Research,* 17:299–302 (1987).

Lavè, D., et al., "Pyrrolo [1,2–c]Thiazole Derivatives: Potent PAF Receptor Antagonists," *Drugs of the Future,* 14(9):891–898 (1989).

McColl, S.R., "Determination of 5–Lipoxygenase Activity in Human Polymorphonuclear Leukocytes Using High–Performance Liquid Chromatography," *J. Chromatography,* 378:444–449 (1986).

Musser, J.H., et al., "5–Lipoxygenase: Properties, Pharmacology, and the Quinolinly(bridged)aryl Class of Inhibitors," *J. Med. Chem.,* 35(14):2502–2524 (1992).

O'Donnell, M., et al., "Comparison of the Pulmonary Pharmacoogy of Leukotrienes and PAF: Effects of Their Antagonists," *Therapeutic Approaches to Inflammatory Disease,* Proceedings of the Fourth International Conference of the Inflammation Research Association, pp. 169–193; White Haven, Pennsylvania (Oct. 23–27, 1988).

Ogiso, A., et al., "The Structure of Futoenone, A Novel Spiro–Cyclohexadienone Derivative," *Tetrahedron Letters,* No. 16, pp. 2003–2008 (1968).

Ogiso, a., et al., "The Structure and Total Synthesis of Futoenone, a Constitute of *Piper futokadzura* SIEB. et ZUCC.[1)]," *Chem. Pharm. Bull.,* 18(1):105–114 (1970).

Page, C. et al., "PAF: New Antagonists, New Roles in Diseases and a Major Role in Reproductive Biology," *Trends in Pharmacol. Sci.,* pp. 256–257 (1989).

Ponpipom, M.M., et al., "(±)–TRANS–2–(3–Methoxy–5–Methylsufonyl–4–Propoxyphenyl)–5–(3,4,5–Trimethoxyphenyl) Tetrahydrofuran (L–659,989), A Novel, Potent PAF Receptor Antagonist," *Biochemical and Biophysical Research Communications,* 150(3):1213–1220 (1988).

Ponpipom, M.M., et al., "Structure–Activity Relationships of Kadsurenone Analogues," *J. Med. Chem.,* 30:136–142 (1987).

Sahoo, et al., "Synthesis and Biological Activity of MK 287 (L–680,573): A Potent, Specific, and Orally Acitive PAF Receptor Antagonist," *Bioorg & Med. Chem. Lett.,* 1(6):327–332 (1991).

Schwenk, et al., "Identification of 5–Oxo–15–hydroxy–6,8,11,13–eicosatetraenoic Acid as a Novel and Potent human Eosinophil Chemotactic Eicosanoid," *J. Biol. Chem.* 267(18):12482–12488 (1992).

Seminaro and Gleich, "The role of eosinophils in the pathogenesis of asthma," *Curr. Opin. in Immunol.,* 6:860–864 (1994).

Shen, T.Y., "Characterization of a Platelet–Activating Factor Receptor Antagonist Isolated from Haifenteng (*Piper futokadsura*): Specific Inhibition of in vitro and in vivo Platelet–Activating Factor–Induced Effects," *Proc. Nat'l. Acad. Sci. USA,* 82:672–676 (1985).

Shen, T.Y., et al., "The Chemical and Biological Properties of PAF Agonists, Antagonists, and Biosynthetic Inhibitors," *Platelet–Activating Factor and Related Lipid Mediators,* Plenum Press, New York, NY, pp. 153–190 (1987).

Shen and Hussaini, "Kadsurenone and Other Related Lignans as Antagonists of Platelet–Activating Factor Receptor," *Methods in Enzymol.,* 187:446–454 (1990).

Shizuri, et al., "Synthesis of some physiologically active substances using anodic oxidation of phenols as a key–step," *Tennen Yuki Kagobutsu Toronkai Koen Yoshishu, Chem. Abstracts,* Abstract 209491p (1983).

Talapatra, et al., "Maglifloenone,a novel spirocyclohexadienone neolignan and other constituents from Magnolia liliflora," *Chem. Abstracts,* Abstract No. 52493k (1982).

Terashita, et al., "CV–3988—A Specific Antagonist of Platelet Ativating Factor (PAF)," *Life Sciences,* 32(17):1975–1982 (1983).

Weber, K.H., et al., "Hetrazepines as Antagonists of Platelet Activating Factor," *Medicinal Research Reviews,* 9(1):181–218 (Jan.–Mar. 1989).

Wood, et al., "Cyclic Ether Acetal Platelet Activating Factor (PACF) Receptor Antagonists II: Imidazo[4,5–c]Pyridyl Derivatives," *Bioorg. & Med. Chem. Lett.,* 3(8):1499–1504 (1993).

Woods and Miura, "The NMR Spectra of Futoenone and Derivative Partial Decoupling as an Aid in the Assignment of Complex Spectra, and Further Observations of Overhauser Effects," *Tet. Letts.,* 16:2209–2014 (1968).

Yeadon, et al., "Effect of BW B70C, a novel inhibitor of arachidonic acid 5–lipoxygenase, on allergen–induced bronchoconstriction and late–phase lung eosinophil accumulation in sensitised guinea–pigs," *Agents and Actions,* 38:8–18 (1993).

COMPOUNDS AND METHODS FOR THE TREATMENT OF CARDIOVASCULAR, INFLAMMATORY AND IMMUNE DISORDERS

The present invention application claims priority to International application No. PCT/US95/00060, filed Jan. 6, 1995 and U.S. application No. 08/178,222, filed Jan. 6, 1994.

FIELD OF THE INVENTION

This invention is in the area of compounds, pharmaceutical compositions and methods for the treatment of inflammatory, cardiovascular and immune disorders. The compounds and compositions of the present invention exhibit these biological activities by acting as PAF receptor antagonists and/or by inhibiting the enzyme 5-lipoxygenase.

BACKGROUND OF THE INVENTION

Platelet activating factor (PAF, 1-0-alkyl-2-acetyl-sn-glycerol-3-phosphorylcholine) is a potent inflammatory phospholipid mediator with a wide variety of biological activities. PAF is generated and released by monocytes, macrophages, polymorphonuclear leukocytes (PMNs), eosinophils, neutrophils, natural killer lymphocytes, platelets and endothelial cells, as well as by renal and cardiac tissues under appropriate immunological and non-immunological stimulation. PAF causes the aggregation and degranulation of platelets at very low concentrations. The potency (active at $10^{-12}$ to $10^{-9}$ M), tissue level (picomoles) and short plasma half life (2–4 minutes) of PAF are similar to those of other lipid mediators such as thromboxane $A^2$, prostaglandins, and leukotrienes.

While PAF mediates essential biological responses, it also appears to play a role in pathological immune and inflammatory responses. Many published studies have provided evidence for the involvement of PAF in human diseases, including arthritis, acute inflammation, asthma, endotoxic shock, pain, psoriasis, ophthalmic inflammation, ischemia, gastrointestinal ulceration, myocardial infarction, inflammatory bowel diseases, and acute respiratory distress syndrome. Animal models also demonstrate that PAF is produced or increased in certain pathological states. Thus, compounds and/or pharmaceutical compositions which act as PAF receptor antagonists will be useful in the treatment of these and other disease states in which excessive amounts of PAF are present.

Leukotrienes, like PAF, are potent local mediators, playing a major role in inflammatory and allergic responses, including arthritis, asthma, psoriasis, and thrombotic disease. Leukotrienes are straight chain eicosanoids produced by the oxidation of arachidonic acid by lipoxygenases. Arachidonic acid is oxidized by 5-lipoxygenase to the hydroperoxide 5-hydroperoxyeicosatetraenoic acid (5-HPETE), which is converted to leukotriene $A_4$, which in turn can be converted to leukotriene $B_4$, $C_4$, or $D_4$. The slow-reacting substance of anaphylaxis is now known to be a mixture of leukotrienes $C_4$, $D_4$, and $E_4$, all of which are potent bronchoconstrictors. There has been a long established research effort to develop specific receptor antagonists or inhibitors of leukotriene biosynthesis, to prevent or minimize pathogenic inflammatory responses mediated by these compounds. As such, compounds and/or pharmaceutical compositions which inhibit the 5-lipoxygenase enzyme will be useful in the treatment of disease states in which excessive amounts of leukotrienes are present.

Given the significant number of pathological immune and inflammatory responses that are mediated by PAF and leukotrienes, there remains a need to identify new compounds and compositions that exhibit PAF receptor antagonistic activity and/or inhibit the enzyme 5-lipoxygenase (5-LO).

SUMMARY OF THE INVENTION 2,5-Diaryl tetrahydrothiophenes, tetrahydrofurans and 1,3-diaryl cyclopentanes depicted in Formula 1 are inhibitors of PAF and/or 5-LO. They can be used for the treatment of pathological immune, inflammatory or cardiovascular disorders.

Formula I

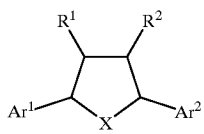

wherein:

$Ar^1$ is either

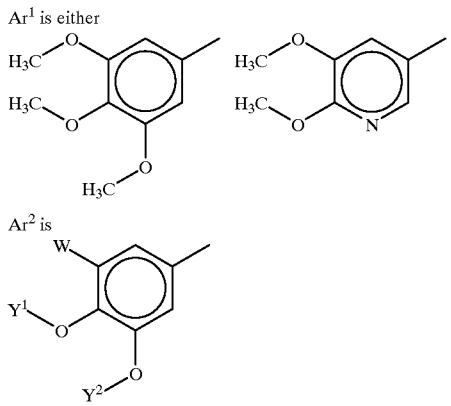

$Ar^2$ is and wherein:

W is independently selected from the group consisting of: —AN(OM)C(O)N($R^3$)$R^4$, —AN($R^3$)C(O)N(OM)$R^4$, —AN(OM)C(O)$R^4$, —AC(O)N(OM)$R^4$, —N(OM)C(O)N($R^3$)$R^4$, —N($R^3$)C(O)N(OM)$R^4$, —N(OM)C(O)$R^4$, —C(O)N(OM)$R^4$, —S(O)$_n$$R^3$, —S(O)$_n$CH$_2$C(O)A, —S(O)$_n$—CH$_2$CH(OH)A, and —C(O)NHA, X is O, S, S(O) C$R^5$;

$Y^1$, $Y^2$ are independently selected from the group consisting of:
(a) hydrogen;
(b) lower alkyl, lower alkoxy, lower alkenyl, lower alkynyl, alkylaryl;
(c) —AN(OM)C(O)N($R^3$)$R^4$, —AN ($R^3$)C(O)N(OM)$R^4$, —AN(OM)C(O)$R^4$, —AC(O)N(OM)$R^4$, —AN($R^3$)C(O)N(OM)$R^4$, —C(O)N(OM)$R^4$, and —C(O)NH$R^3$;

wherein A is selected from the group consisting of substituted or unsubstituted lower alkyl, lower alkyl-alkoxy, -lower alkyl-heterocycle-lower alkyl-, specifically including —CH$_2$-heterocycle-CH$_2$—, wherein the heterocycle is preferably furan or pyridine, more preferably, wherein the alkyl substituents are in the 2 and 5 positions of the furan ring, or the 2 and 6 positions of the pyridine ring, lower alkenyl, lower alkynyl, alkaryl or aralkyl; M is selected from hydrogen, a pharmaceutically acceptable cation, and a metabolically cleavable leaving group; $R^1$ and $R^2$ are independently selected from hydrogen, lower alkyl, preferably lower alkyl of 1–6 carbon atoms, e.g., methyl, cyclopropyl-methyl, ethyl, isopropyl, butyl, pentyl and hexyl, as well as $C_{3-8}$, cycloalkyl, for example, cyclopentyl, halo lower alkyl, especially $C_{1-6}$ haloalkyl, for example, trifluoromethyl, halo, especially fluoro, —COOH; $R^3$ and $R^4$ are independently selected from the group consisting of hydrogen, substituted or unsubstituted alkyl, substituted or unsubstituted alkyl where one or more carbon atoms are replaced by S, N, or O, substituted or unsubstituted cycloalkyl of from 3 to 10 carbon atoms, substituted or unsubstituted cycloalkyl of from 3 to 10 carbon atoms, where one or more carbons are replaced by S, N, or O, preferably lower alkyl, alkenyl, preferably lower alkenyl, alkynyl, preferably lower alkynyl, aryl, preferably phenyl, aralkyl, preferably benzyl, alkaryl, preferably toluyl, $C_{1-6}$ alkoxy-$C_{1-10}$ alkyl, $C_{1-6}$ alkylthio-$C_{1-10}$ alkyl, $C_{1-6}$ hydroxy-$C_{1-6}$ alkyl, $C_{1-6}$ carbonyl-$C_{1-6}$ alkyl, $C_{1-6}$ amino- $C_{1-6}$ alkyl;

$R^5$ is selected from the group consisting of:
(a) hydrogen,
(b) lower alkyl, lower alkenyl, lower alkynyl, alkaryl;
(c) —AN(OM)C(O)N($R^3$)$R^4$, —AN($R^3$)C(O)N(OM)$R^4$, —AN(OM)C(O)$R^4$, —AC(O)N(OM)$R^4$, —AC(O)N(OM)$R^4$, —AS(O)$_n R^3$, —AS(O)$_n$—CH$_2$C(O)$R^3$, —AS(O)$_n$—CH$_2$CH(OH)$R^3$, —AC(O)NH$R^3$, wherein each n is independently 0, 1 or 2; A is selected from the group consisting of substituted or unsubstituted lower alkyl, lower alkoxy, lower alkenyl, lower alkynyl, alkaryl or aralkyl; M is selected from hydrogen, a pharmaceutically acceptable cation, or a metabolically cleavable leaving group.

Preferred compounds of Formula I have the following structure:

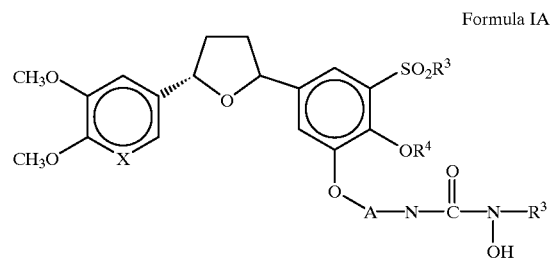

Formula IA wherein A, $R^3$, and $R^4$ are all independently selected from the groups as defined above, X is N or C—OCH$_3$ and n is as defined above, and pharmaceutically acceptable salts thereof.

More preferred compounds of Formula I have the following structure:

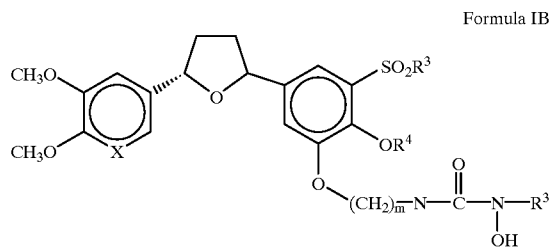

Formula IB wherein $R^3$ and $R^4$ are independently selected from the groups defined above, preferably $R^3$ and $R^4$ are independently selected from the preferred groups defined above; X is N or C—OCH$_3$ and m is 2–10, and pharmaceutically acceptable salts thereof.

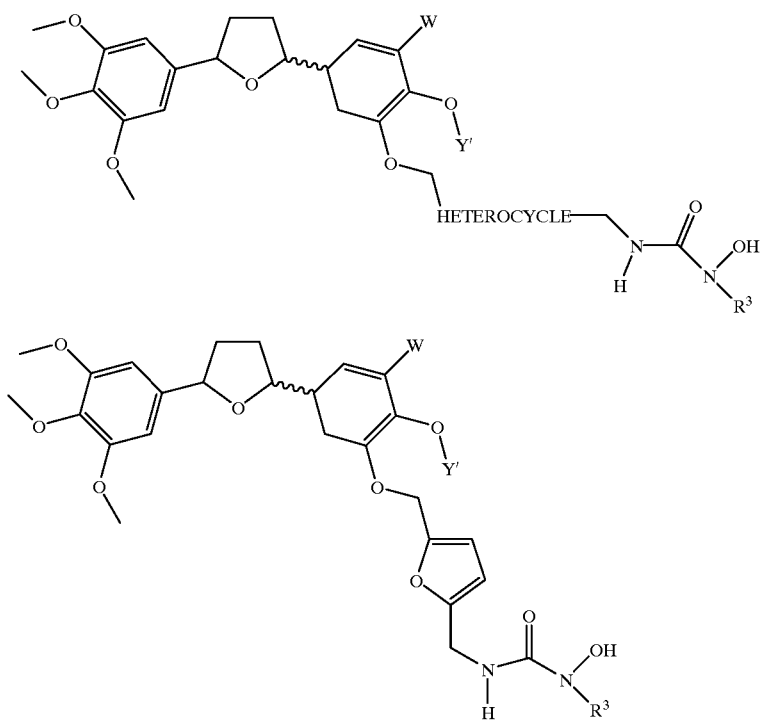

-continued

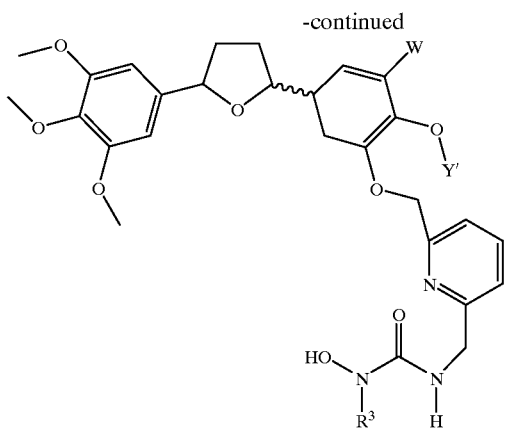

DETAILED DESCRIPTION OF THE PREFERRED EMBODIMENTS

A. Description and Properties of the Preferred Compounds

The term alkyl, as used herein, unless otherwise specified, refers to a saturated straight, branched, or cyclic hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term lower alkyl, as used herein, and unless otherwise specified, refers to a $C_1$ to $C_6$ saturated straight, branched, or cyclic (in the case of $C_{5-6}$) hydrocarbon, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term alkenyl, as referred to herein, and unless otherwise specified, refers to a straight, branched, or cyclic (in the case of $C_{5-6}$) hydrocarbon of $C_2$ to $C_{10}$ with at least one double bond.

The term lower alkenyl, as referred to herein, and unless otherwise specified, refers to an alkenyl group of $C_2$ to $C_6$, and specifically includes vinyl and allyl.

The term lower alkylamino refers to an amino group that has one or two lower alkyl substituents.

The term alkynyl, as referred to herein, and unless otherwise specified, refers to a $C_2$ to $C_{10}$ straight or branched hydrocarbon with at least one triple bond.

The term lower alkynyl, as referred to herein, and unless otherwise specified, refers to a $C_2$ to $C_6$ alkynyl group, specifically including acetylenyl and propynyl.

The term aryl, as used herein, and unless otherwise specified, refers to phenyl or substituted phenyl, wherein the substituent is halo or lower alkyl.

The term halo, as used herein, includes fluoro, chloro, bromo, and iodo.

The term halo (alkyl, alkenyl, or alkynyl) refers to a (alkyl, alkenyl, or alkynyl) group in which at least one of the hydrogens in the group has been replaced with a halogen atom.

The term heterocycle or heteroaromatic, as used herein, refers to an aromatic moiety that includes at least one sulfur, oxygen, or nitrogen in the aromatic ring. Non-limiting examples are pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl.

The term aralkyl refers to an aryl group with an alkyl substituent.

The term alkaryl refers to an alkyl group that has an aryl substituent.

The term substituted (e.g., substituted alkyl) refers to one or more substituent groups selected from the following: halogen, hydroxy, amino, $C_1$–$C_6$ alkylamino, $C_2$–$C_{15}$ dialkylamino, carbamoyl, $C_1$–$C_6$ N-alkylcarbamoyl, $C_2$–$C_{15}$ N,N-dialkylcarbamoyl, cyano, nitro, $C_2$–$C_{15}$ dialkylsulfamoyl, $CF_3$, $C_1$–$C_6$ acyl, $C_1$–$C_6$ alkoxy, carboxy, $C_2$–$C_6$ carboxylic acid, carboxamido, allyl, thio, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_2$–$C_6$, haloalkoxy, and the like.

The term organic or inorganic anion refers to an organic or inorganic moiety that carries a negative charge and can be used as the negative portion of a salt.

The term "pharmaceutically acceptable cation" refers to an organic or inorganic moiety that carries a positive charge and that can be administered in association with a pharmaceutical agent, for example, as a countercation in a salt. Pharmaceutically acceptable cations are known to those of skill in the art, and include but are not limited to sodium, potassium, and quaternary amine.

The term "metabolically cleavable leaving group" refers to a moiety that can be cleaved in vivo from the molecule to which it is attached, and includes but is not limited to an organic or inorganic anion, a pharmaceutically acceptable cation, acyl (for example (alkyl)C(O), including acetyl, propionyl, and butyryl), alkyl, phosphate, sulfate and sulfonate.

The term pharmaceutically acceptable salts or complexes refers to salts or complexes that retain the desired biological activity of the above-identified compounds and exhibit minimal undesired toxicological effects.

The term PAF receptor antagonist refers to a compound that binds to a PAF receptor with a binding constant of 30 $\mu M$ or lower.

The term 5-lipoxygenase inhibitor refers to a compound that inhibits the enzyme at 30 $\mu M$ or lower in a broken call system.

The term pharmaceutically active derivative refers to any compound that upon administration to the recipient, is capable of providing directly or indirectly, the compounds disclosed herein.

Preferred 2,5-diaryl tetrahydrothiophenes, and tetrahydrofurans and 1,3-diaryl cyclopentanes of the present invention exhibit PAF receptor antagonist activity with an $IC_{50}$ of from about 1 nM to about 1 $\mu$M, and/or they inhibit the enzyme 5-lipoxygenase with an $IC_{50}$ of from about 50 nM to about 10 $\mu$M, or they have dual activity, and are thus useful in the treatment of mammals, including humans, who have immune, allergic or cardiovascular disorders that are mediated by PAF or products of 5-lipoxygenase.

B. Stereochemistry

The 2,5-diaryl tetrahydrofurans, tetrahydrothiophenes, and 1,3-cyclopentanes disclosed herein exhibit a number of stereochemical configurations. Carbon atoms 2 and 5 in the center ring are chiral, and thus the center ring exists at a minimum as a diastereomeric pair. Each diastereomer exists as a set of enantiomers. Therefore, based on the chiral $C_2$ and $C_5$ atoms alone, the compound is a mixture of four enantiomers. The present invention is thus directed to each of the separated enantiomers, as well as to all of the possible mixtures thereof.

If nonhydrogen substituents are located on carbon atoms 3 and 4 in the center ring, then the $C_3$ and $C_4$ atoms are also chiral, and can also exist as a diastereomeric pair, that is also a mixture of four enantiomers.

The R groups in the active compounds described herein can likewise include chiral carbons, and thus, optically active centers.

C. Pharmaceutical Compositions

Humans, equine, canine, bovine and other animals, and in particular, mammals, suffering from inflammatory diseases, and in particular, disorders mediated by PAF or products of 5-lipoxygenase can be treated by administering to the patient an effective amount of one or more of the above-identified compounds or a pharmaceutically acceptable derivative or salt thereof in a pharmaceutically acceptable carrier or diluent to reduce formation of oxygen radicals. The active materials can be administered by any appropriate route, for example, orally, parenterally, intravenously, intradermally, subcutaneously, or topically, in liquid, cream, gel or solid form.

The active compound is generally included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01–3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. An oral dosage of 25–250 mg is usually convenient.

The active ingredient should be administered to achieve peak plasma concentrations of the active compound of about 0.01–30 mM, preferably about 0.1–10 mM. This may be achieved, for example, by the intravenous injection of a solution or formulation of the active ingredient, optionally in saline, or an aqueous medium or administered as a bolus of the active ingredient.

The active compound or pharmaceutically acceptable derivatives or salts thereof can also be mixed with other active materials that do not impair the desired action, or with materials that supplement the desired action, such as antibiotics, antifungals, other anti-inflammatories, or antiviral compounds.

D. Biological Activity

A wide variety of biological assays have been used to evaluate the ability of a compound to act as a PAF receptor antagonist, including the ability of the compound to bind to PAF receptors, and the effect of the compound on various PAF mediated pathways. Any of these known assays can be used to confirm the ability of the compounds disclosed herein to act as PAF receptor antagonists.

For example, PAF is known to induce hemoconcentration and increased permeability of microcirculation leading to a decrease in plasma volume. PAF mediated acute circulatory collapse can be used as the basis of an assay to evaluate the ability of a compound to act as a PAF antagonist, by analyzing the effect of the compound on PAF induced decreased plasma volume in an animal model such as mouse.

Endotoxemia causes the release of chemical mediators including eicosanoids, PAF, and tumor necrosis factor (TNF) that stimulate a variety of physiologic responses including fever, hypotension, leukocytosis, and disturbances in glucose and lipid metabolism. Endotoxemia can result in severe shock and death. Endotoxin-induced mouse mortality is a useful animal model to evaluate the pharmacological effect of compounds on endotoxic shock.

A wide variety of biological assays have also been used to evaluate the ability of a compound to inhibit the enzyme 5-lipoxygenase. For example, a cytosol 5-lipoxygenase of rat basophilic leukemia cells (RBL) has been widely utilized in studies on leukotriene biosynthesis. Compounds that inhibit 5-lipoxygenase decrease the levels of leukotrienes.

Another biological assay used to evaluate the ability of a compound to inhibit the enzyme 5-lipoxygenase is based on the classic pharmacological model of inflammation induced by the topical application of arachidonic acid to the mouse ear. On application, arachidonic acid is converted by 5-lipoxygenass to various leukotrienes (and other mediators), which induce changes in blood flow, erythema, and increase vasodilation and vasopermeability. The resulting edema is measured by comparing the thickness of the treated ear to a control ear. Agents that inhibit 5-lipoxygenase reduce the edematous response, by lowering the amounts of biochemical mediators formed from arachidonic acid.

E. Syntheses of the Preferred Compounds

The 2,5-diaryl tetrahydrofurans and tetrahydrothiophenes disclosed herein can be prepared in a variety of ways known to those skilled in the art, including by methods disclosed by Biftu, et al. in U.S. Pat. Nos. 4,539,332, 4,757,084, 4,996, 203 and 5,001,123, and European Patent Application Nos. 90306234.7, 90306235.4, and 89202593.3.

1,3-Diaryl cyclopentanes can be prepared using the procedure of Graham, et al. (1.3-Diaryl Cyclopentanes: A New Class of Potent PAF 5 Receptor Antagonists. 197th ACS National Meeting, Dallas, Tex., Apr. 9–14, 1989, Division of Medicinal Chemistry, poster no. 25 (abstract)), or by other known methods.

A general procedure for preparing a hydroxyurea is:

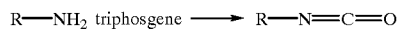
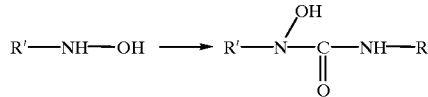

wherein R is a 2,5-diaryl tetrahydrothiophene or tetrahydrofuran; 1,3-diaryl cyclopentane with or without a linking moiety, and R' is a moiety as defined in detail above.

General procedures for preparing reverse hydroxyureas are:

1.
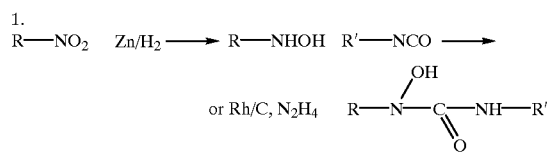

2.
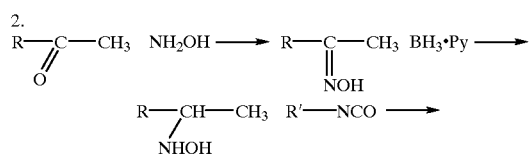

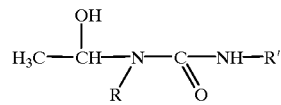

A general procedure for preparing a hydroxamic acid is:

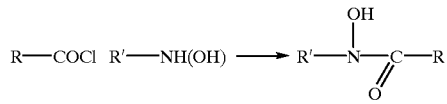

A general procedure for preparing a reverse hydroxamic acid is:

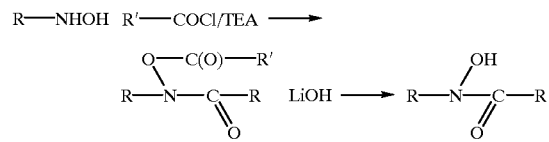

The following schemes (1–10) illustrate the preferred synthetic methods utilized herein. The examples which follow these schemes are reflective thereof. These examples are merely illustrative, and are not intended to limit the scope of the present invention.

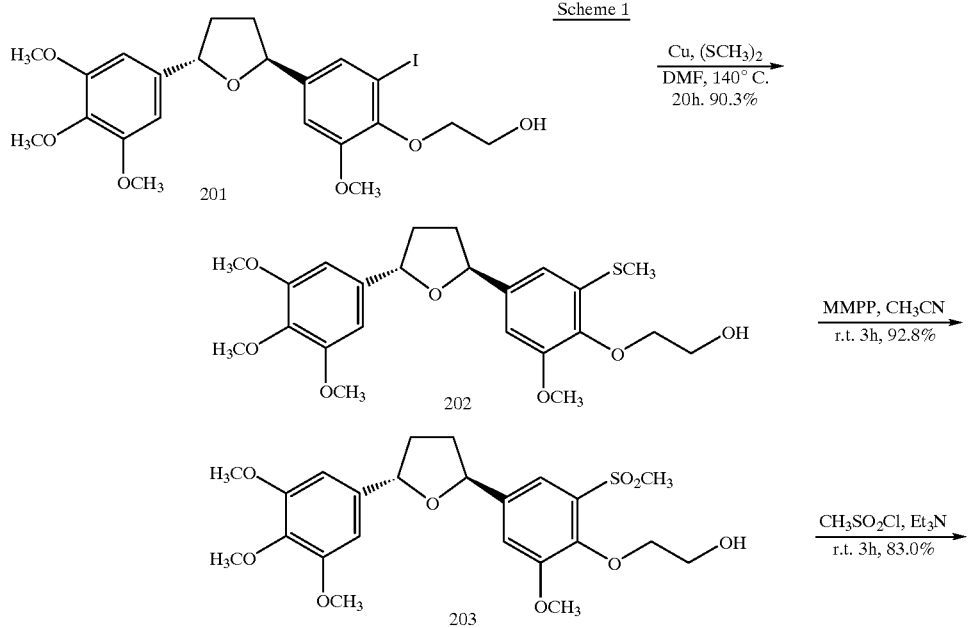

Scheme 1

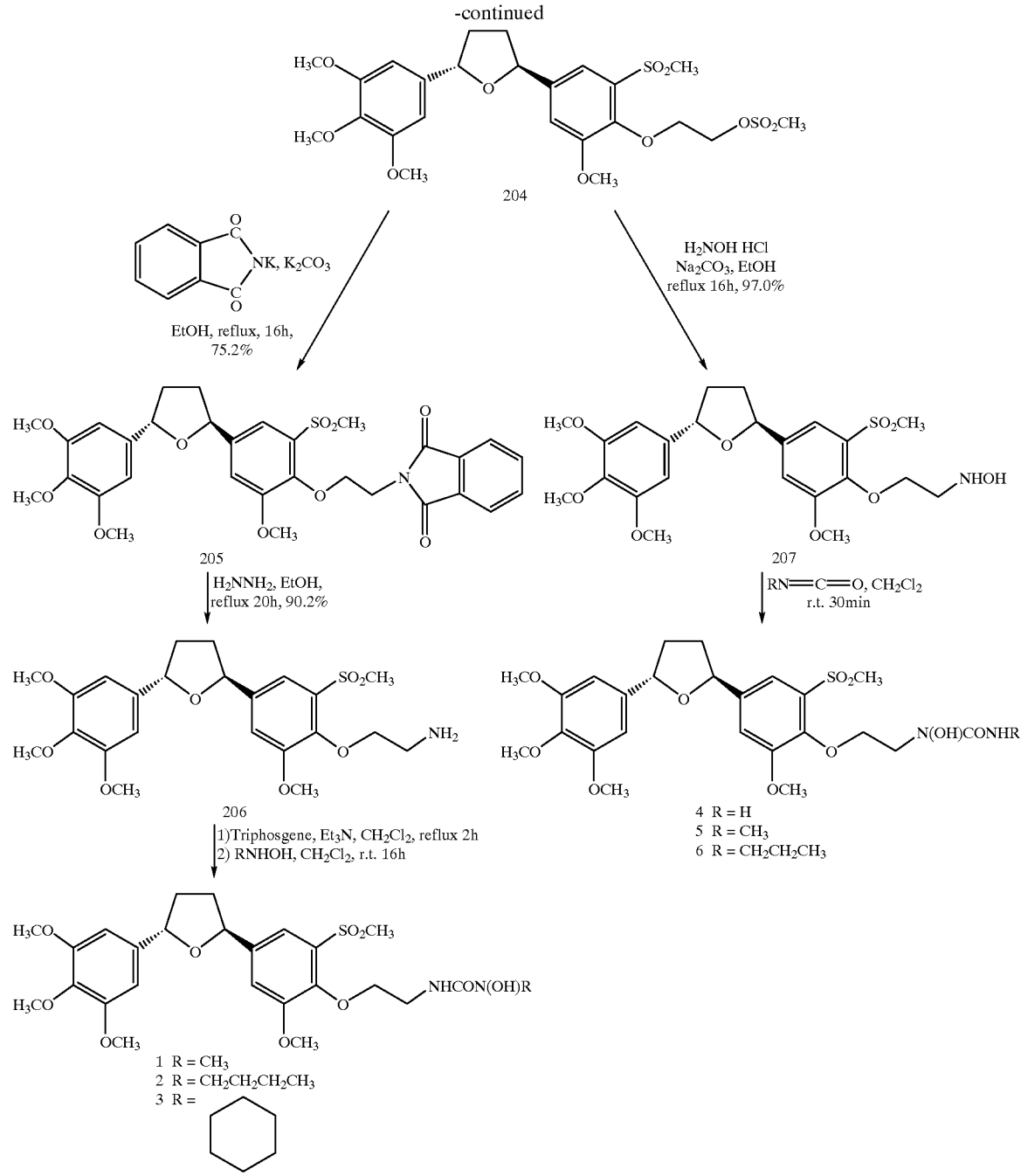

Scheme 2
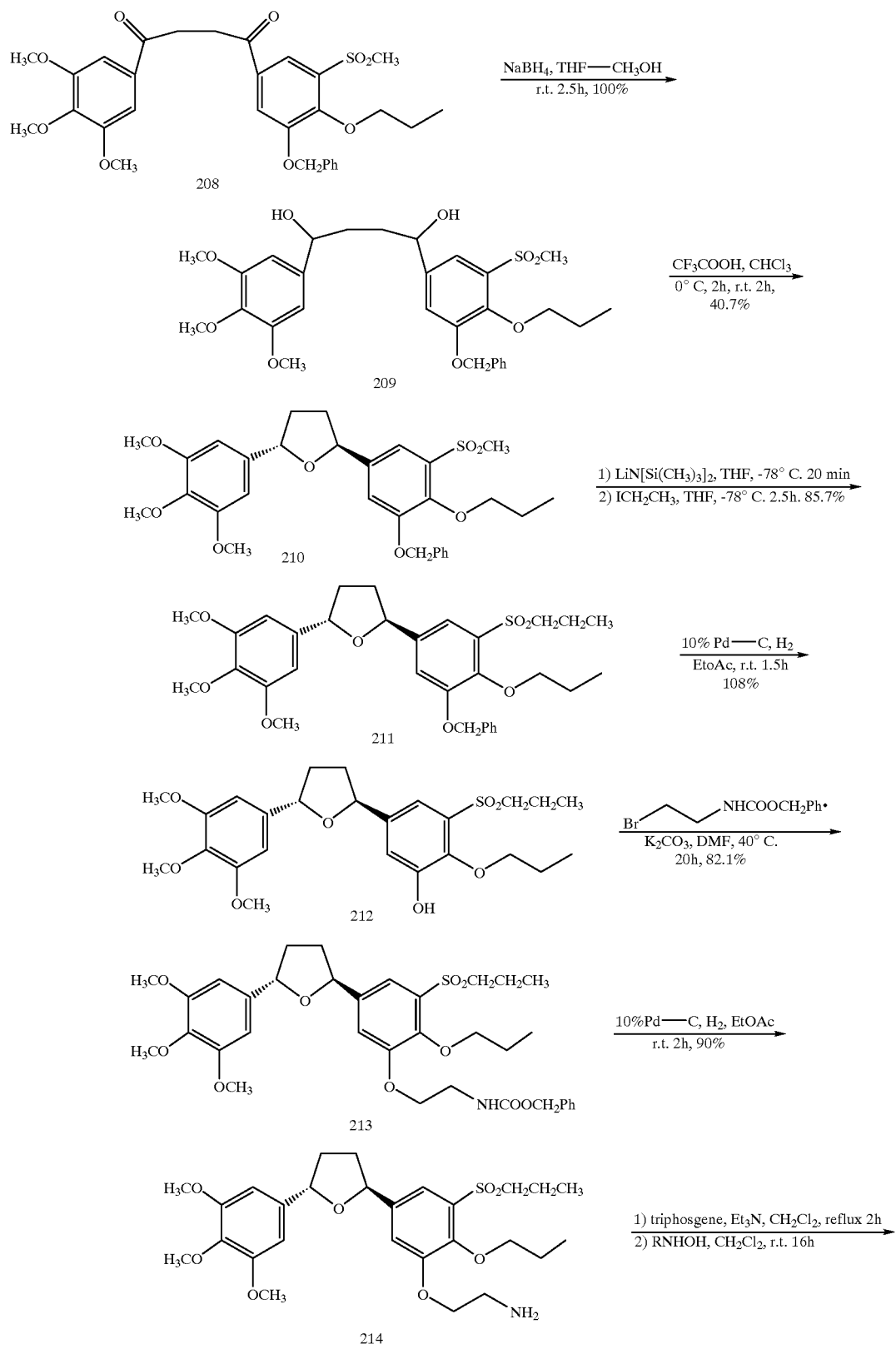

-continued
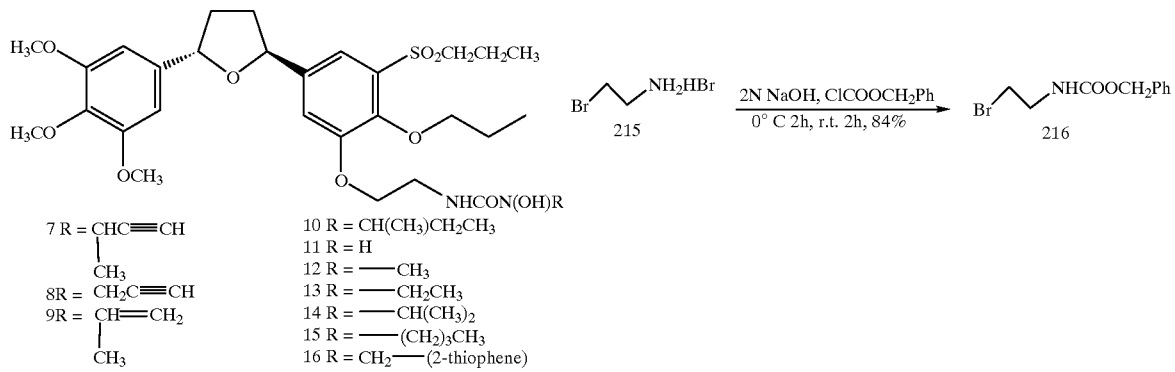
Scheme 3
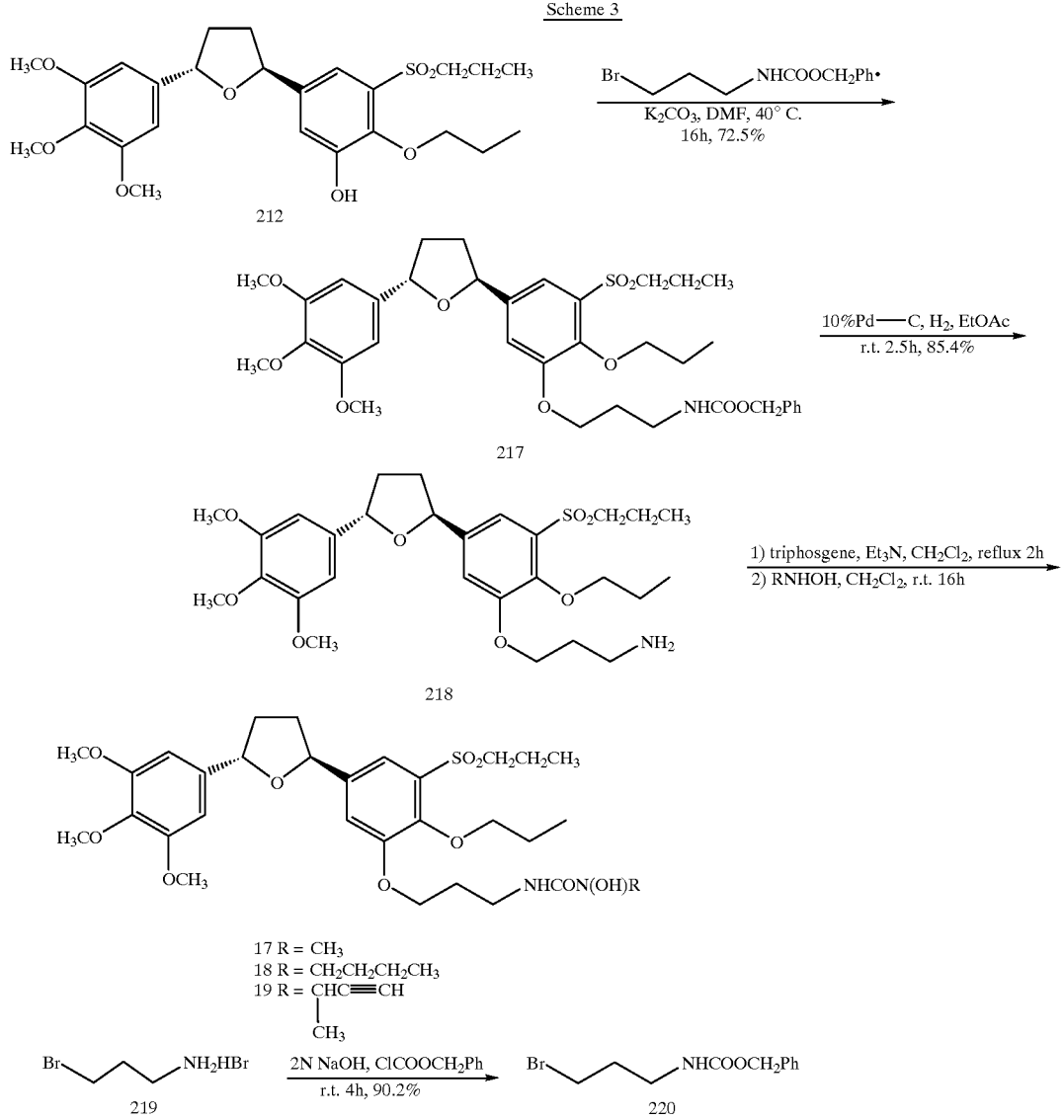

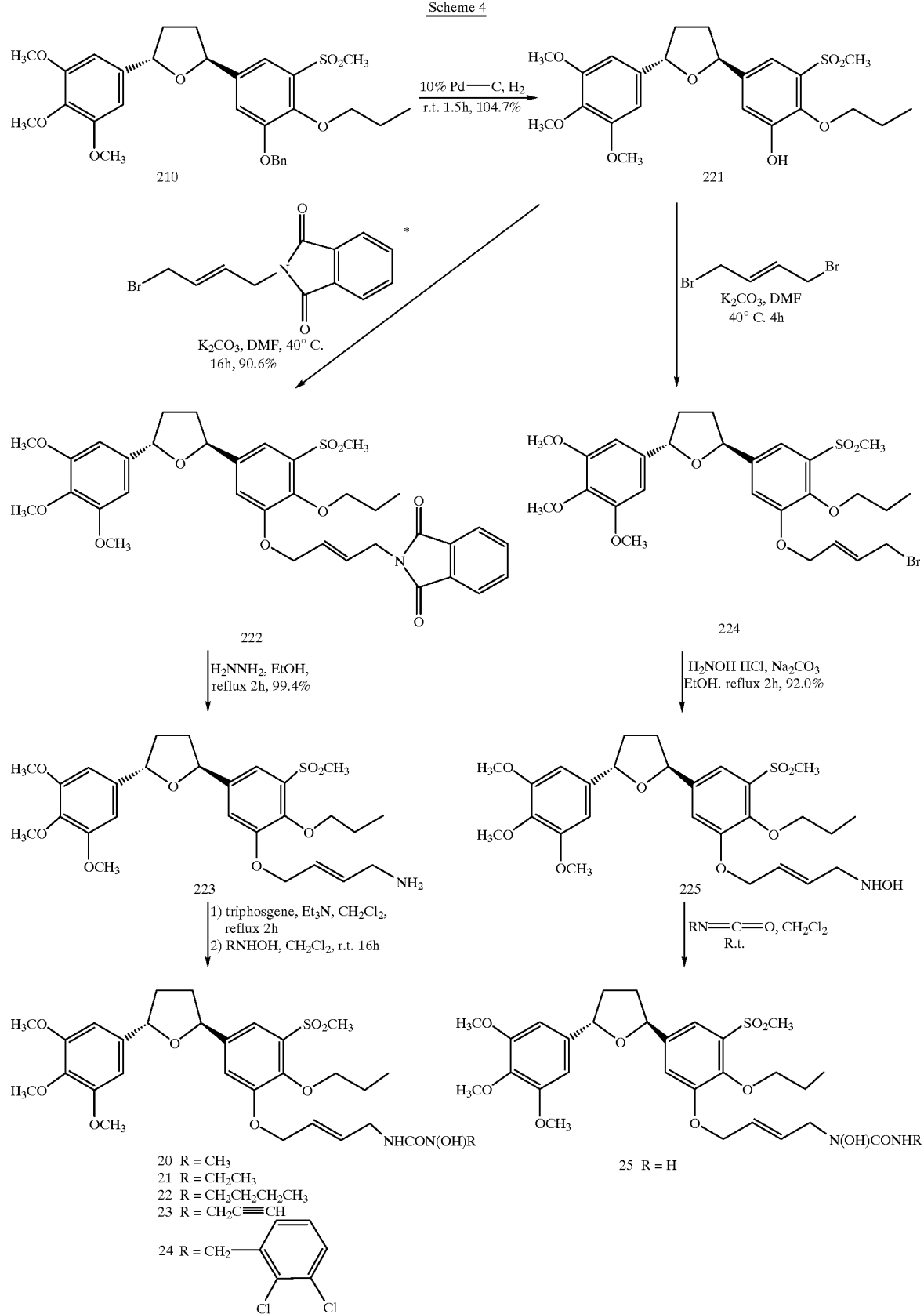

-continued
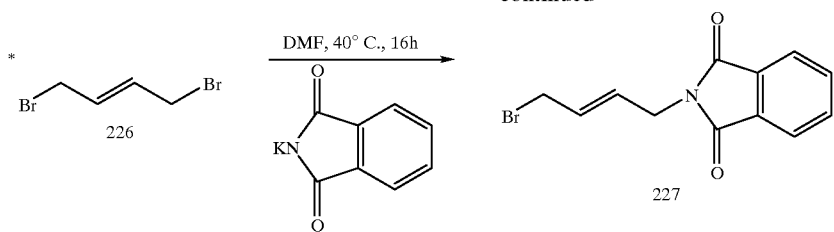
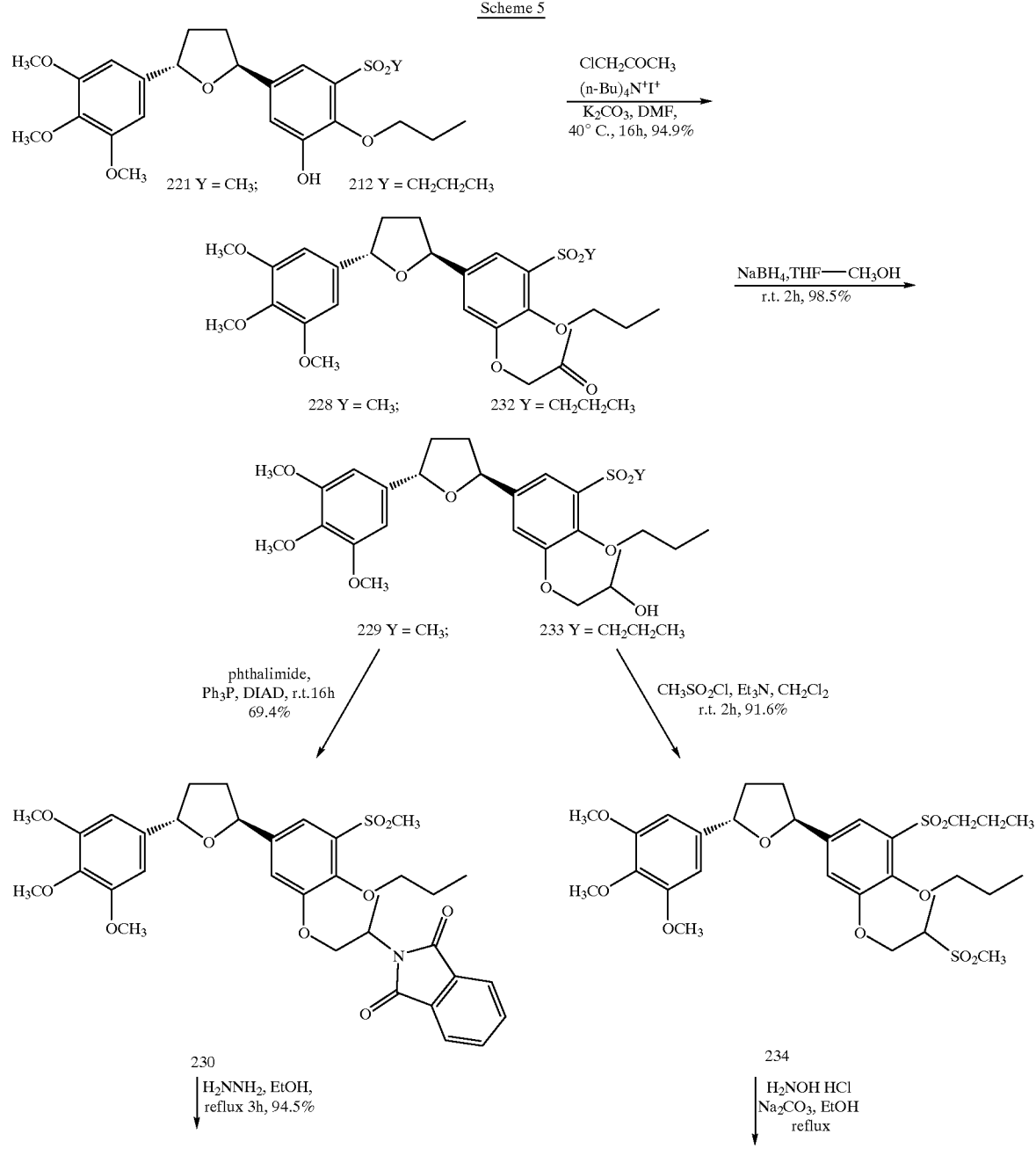
Scheme 5

-continued
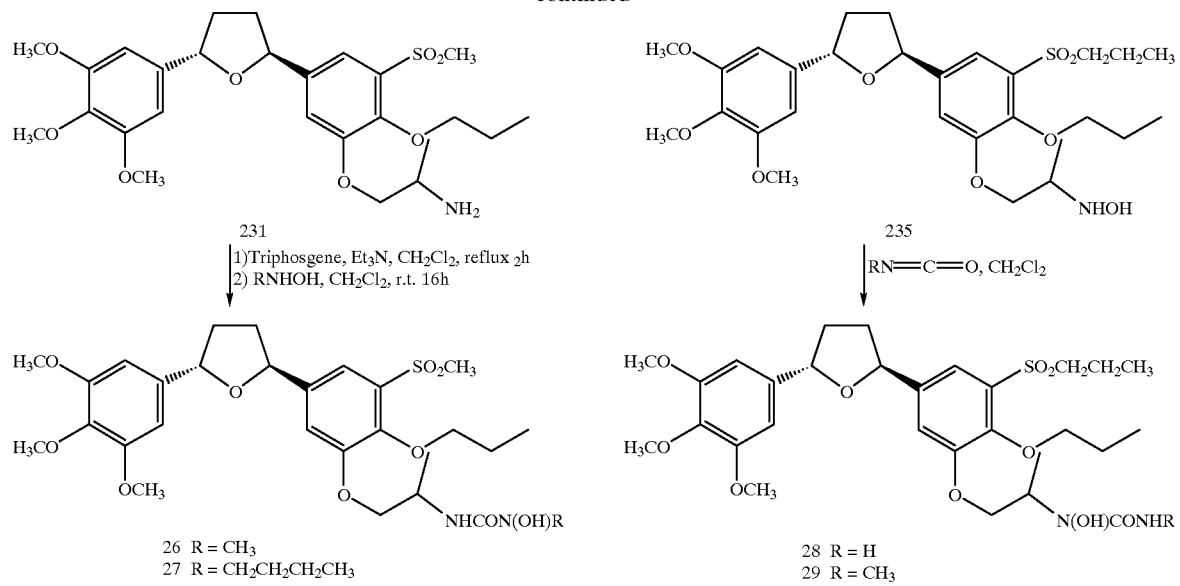
Scheme 6
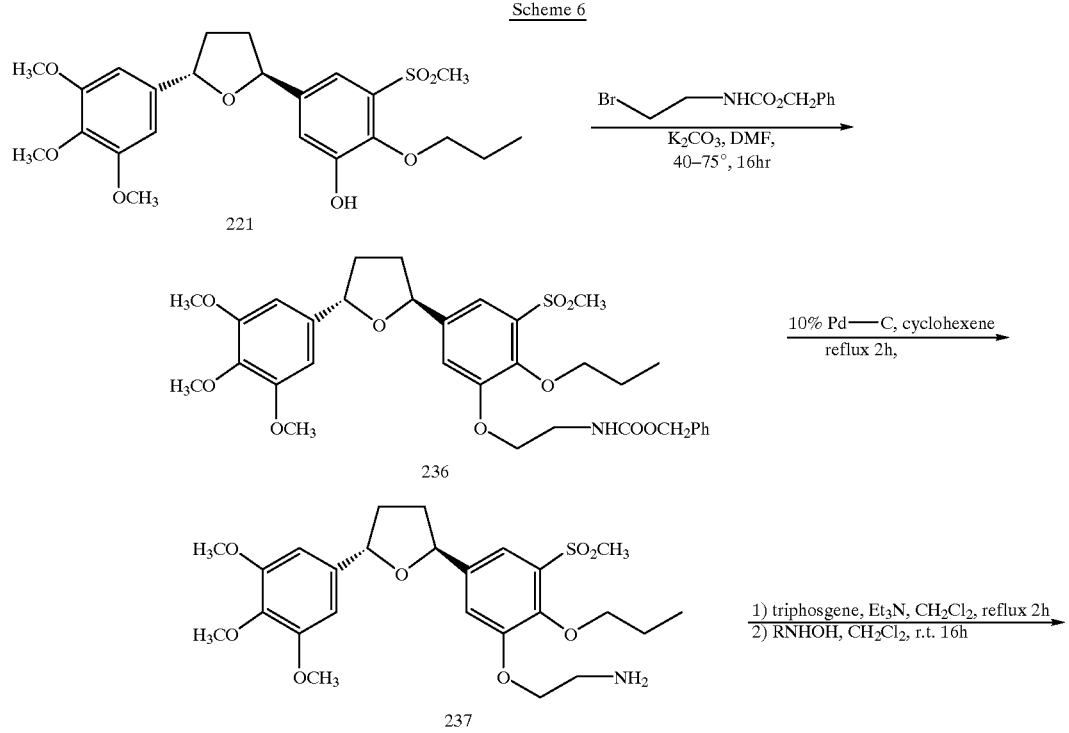

-continued
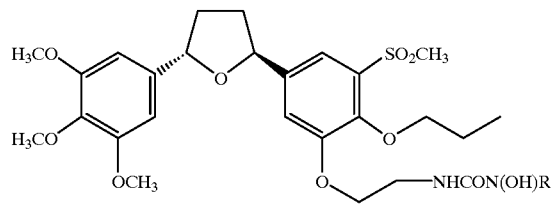
30 R = CH$_3$
31 R = C$_2$H$_5$
32 R = C$_4$H$_9$
Scheme 7
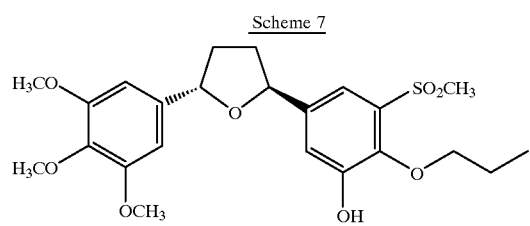
221
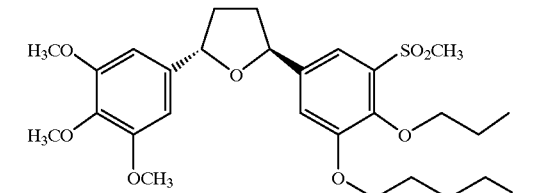
239
1) triphosgene, Et$_3$N, CH$_2$Cl$_2$, reflux 2h
2) RNHOH, CH$_2$Cl$_2$, r.t. 16h
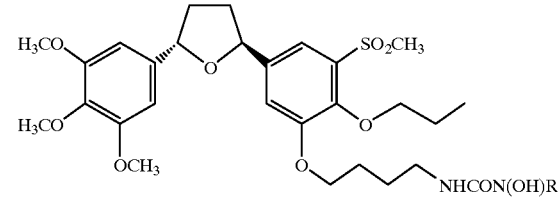
33 R = CH$_3$
34 R = CH$_2$CH$_3$
35 R = (CH$_3$)$_2$CH
36 R = CH$_2$CH$_2$CH$_2$CH$_3$
37 R = (CH$_2$)$_4$CH$_2$
Br(CH$_2$)$_4$-phthalimide
K$_2$CO$_3$, DMF, 100° C., 16h
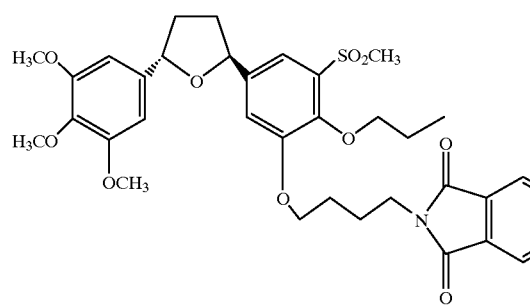
238
H$_2$NNH$_2$, EtOH, reflux O/N

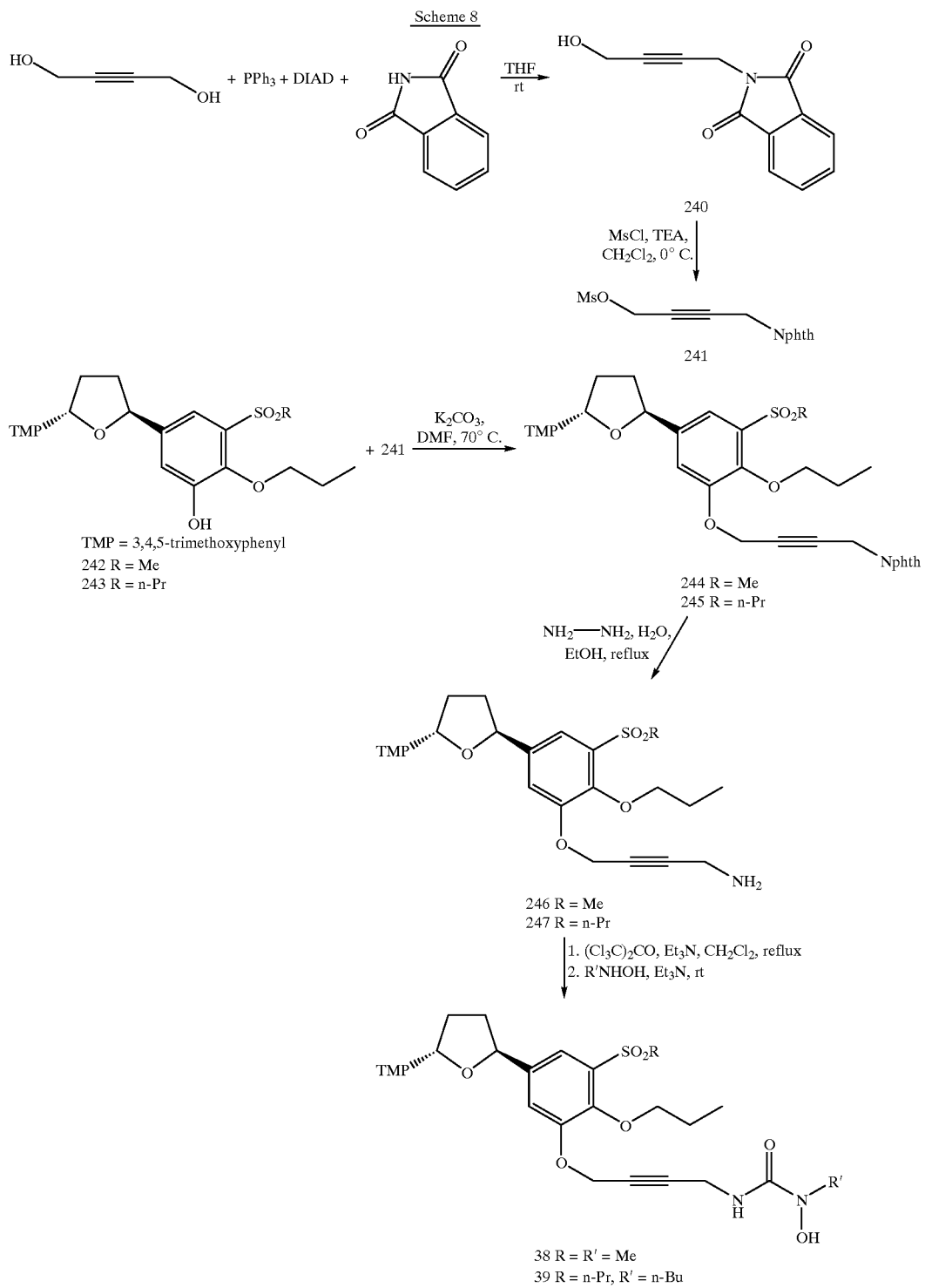

Scheme 9
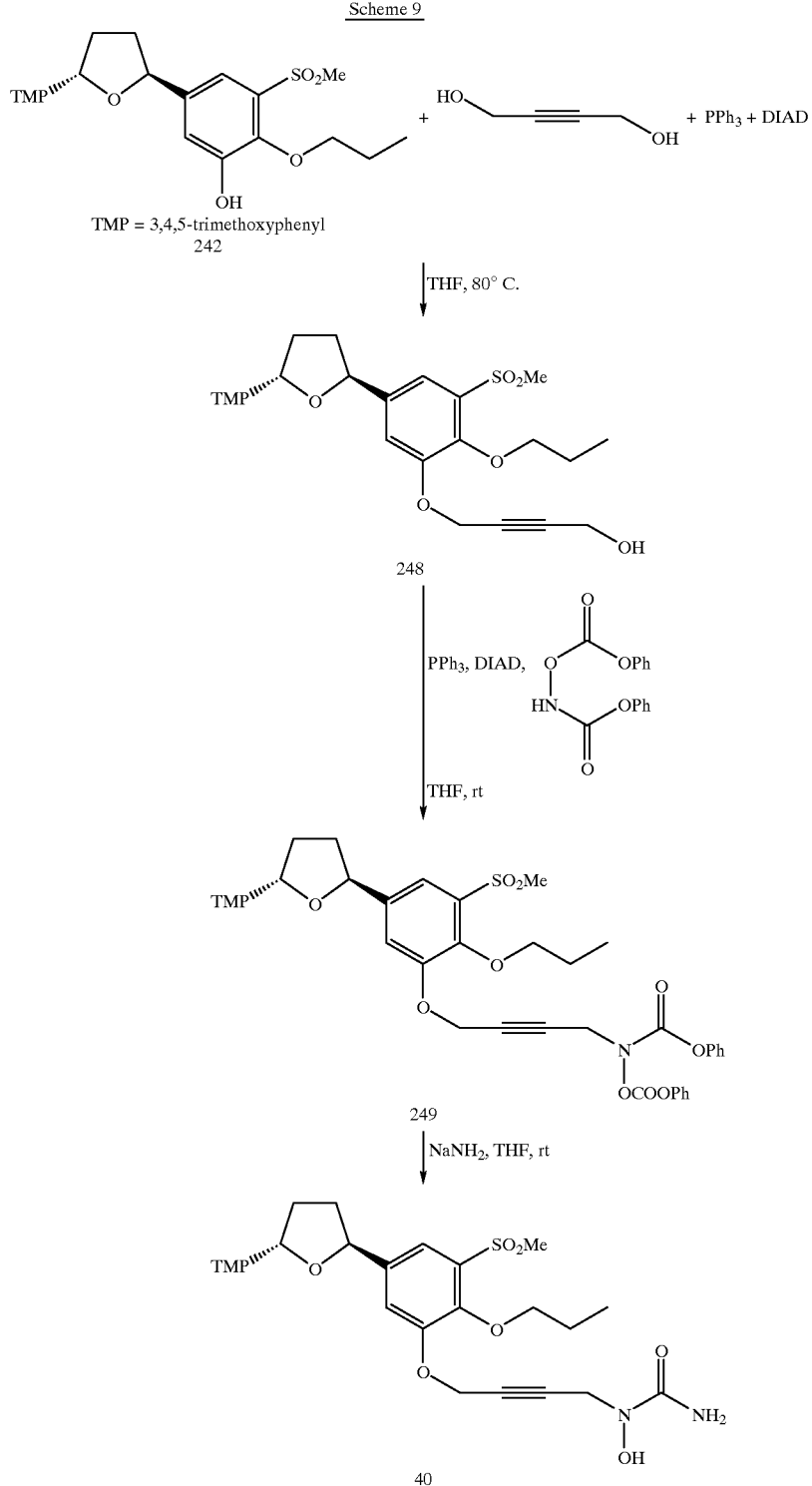

Scheme 10
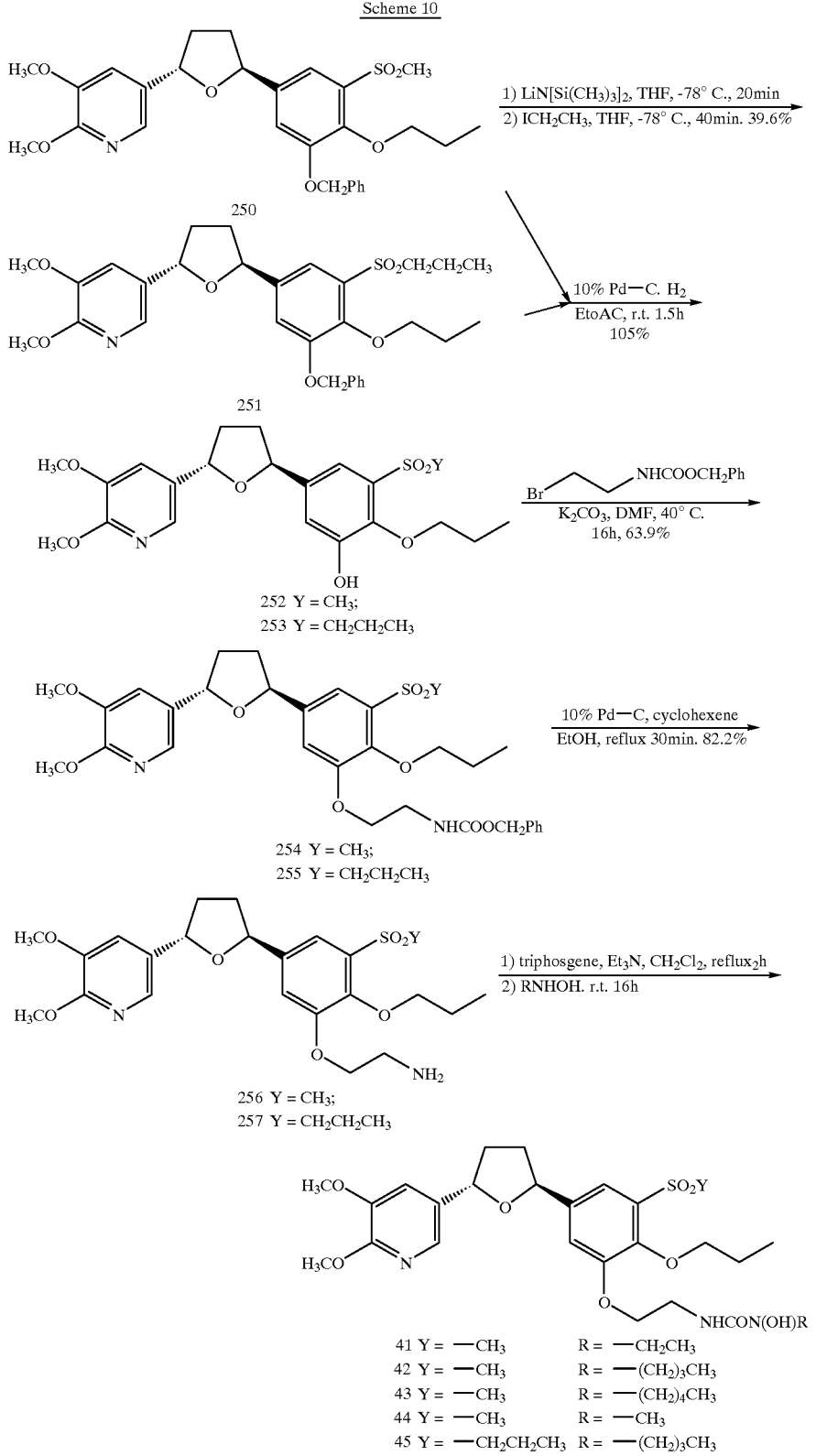
EXAMPLE 1
3-(N,N-Dimethylamino)-1-(3,4,5-trimethoxyphenyl)-1-propanone (compound 101)
3,4,5-Trimethoxyacetophenone (50 g, 237.8 mmole), paraformaldehyde (9.75 g, 304.7 mmole), dimethylamine hydrochloride (26.42 g, 324.0 mmole) and 5 mL conc. HCl were dissolved in 200 mL absolute ethanol and refluxed for 10 hours. Additional dimethylamine hydrochloride (13.21 g, 162.0 mmole) and paraformaldehyde (9.75 g, 304.7 mmole) were added and the solution returned to reflux. After 54 hours (total reaction time), 80 mL of 10% HCl and 500 mL of water were added and the solution was extracted with ethyl ether. The acidic aqueous layer was adjusted to pH 10 with 10% NaOH. The basic solution was extracted with ethyl acetate, dried over $MgSO_4$, filtered and evaporated in vacuo to provide 57.5 g of a yellow oil (92%). $^1$H NMR ($CDCl_3$): δ2.30 (s, 6 H); 2.74 (t, 2 H); 3.11 (t, 3 H); 3.91 (s, 9 H); 7.23 (s, 1 H); 7.32 (s, 1 H).

3-(N,N,N-Trimethylamino)-1-(3,4,5-trimethoxyphenyl)-1-propanone iodide (compound 102)

3-(N,N-Dimethylamino)-1-(3,4,5-trimethoxyphenyl)-1-propanone (57 g, 213.5 mmole) was dissolved in 200 mL of anhydrous diethyl ether. To this solution was added methyl iodide (57.6 g, 405.7 mmole). A white precipitate formed immediately, and the reaction mixture was stirred at room temperature for an additional 2 hours. This product was isolated by suction filtration (83.8 g, 96%).

3,4,5-Trimethoxyphenylvinylketone (compound 103)

3-(N,N,N-Trimethylamino)-1-(3,4,5-trimethoxyphenyl)-1-propanone iodide (50 g, 120 mmole) was dissolved in $H_2O$ (500 mL) and ethyl acetate (500 mL) was added. The mixture was vigorously stirred at reflux for 3 hours. The reaction mixture was cooled and the layers were separated. To the aqueous phase was added ethyl acetate (400 mL). This was brought to reflux for 1.5 hours. The reaction mixture was cooled and separated. The combined organic layers were washed with saturated NaCl solution, dried over $Na_2SO_4$, filtered and concentrated in vacuo to an oil which was purified by flash column chromatography using 3:1 hexane/ethyl acetate as solvent (14.7 g, 54%). $^1$H NMR ($CDCl_3$) δ3.92 (s, 9 H); 5.92 (d, 1 H); 6.44 (d, 1 H); 7.12 (m, 1 H); 7.22 (s, 2 H).

3-Methoxy-4-hydoxyethoxy-6-iodobenzaldehyde (compound 104)

5-Iodovanillin (25 g, 90 mmol) in DMF (100 mL) was added to potassium carbonate (18.6 g, 135 mmol). The mixture was heated at 40° C. for 16 hours. The reaction mixture was allowed to cool to room temperature and quenched with water (500 mL) and extracted with ethyl acetate. The organic layer was washed with water and saturated NaCl solution, and dried over $MgSO_4$, filtered and evaporated in vacuo to an oil, and then purified by column chromatography (silica, 2:1 hexane/ethyl acetate), to provide the product (16.6 g, 57%). $^1$H NMR ($CDCl_3$) δ2.70 (t, 1 H); 3.92 (t, 2 H); 3.92 (s, 3 H); 3.94 (s, 3 H); 4.29 (t, 2 H); 7.44 (s, 1 H); 7.87 (s, 1 H); 9.85 (9, 1 H).

I-(3-Methoxy-4-hydroxyethoxy-5-iodophenyl)-4-(3,4,5-trimethoxyphenyl)-1,4-butanedione (compound 105)

3,4,5-Trimethoxyphenylvinylketone (4.8 g, 21.6 mmol), 3-methoxy-4-hydroxyethoxy-5-iodobenzaldehyde (5.7 g, 17.8 mmol), and 3-benzyl-5-(2-hydroxyethyl)-4-methylthiazolium chloride (1.9 g, 7.0 mmol) were stirred in triethylamine (20 mL) at 60° C. for 16 hours. The reaction mixture was then acidified with 10% HCl, and extracted with dichloromethane. The organic layer was dried over $MgSO_4$, filtered and evaporated in vacuo. The product was purified in column chromatography (silica, 1:1 hexane/ethyl acetate) as a solid (9.7 g, 51%). $^1$H NMR ($CDCl_3$) δ3.41 (m, 4 H); 3.90 (m, 2 H); 3.92 (s, 3 H); 3.93 (s, 9 H); 4.26 (t, 2 H); 7.29 (s, 2 H); 7.57 (d, 1 H); 8.08 (d, I H).

1-(3-Methoxy-4-hydroxyethoxy-5-iodophenyl)-4-(3,4,5-trimethoxyphenyl)-1,4-butanediol (compound 106)

1-(3-Methoxy-4-hydroxyethoxy-5-iodophenyl)-4-(3,4,5-trimethoxyphenyl)-1,4-butanedione (11.6 g, 21.3 mmol), was added to 120 mL tetrahydrofuran and 240 mL methanol. To this solution was added dropwise sodium borohydride (1.45 g, 38.4 mmol), in 60 mL water. The reaction mixture was stirred at room temperature for 2.5 hours, and then cooled, quenched with water, and the aqueous layer extracted with ethyl acetate. The organic layer was dried over $MgSO_4$, filtered and evaporated in vacuo to provide the product (11.8 g, 98.8%). $^1$H NMR ($CDCl_3$) δ1.84 (m, 4 H); 3.84 (m, 2 H); 3.86 (s, 3 H); (s, 9 H); 4.15 (t, 2 H); 4.68 (m, 2 H); 6.57 (s, 2 H); 6.91 (9, 1 H); 7.32 (s, 1 H).

Trans-2-(3-methoxy-4-hydroxyethoxy-5-iodophenyl)-5-(3,4,5-trimethoxyphenyl)tetrahydrofuran (compound 107)

To 1-(3-methoxy-4-hydroxyethoxy-5-iodophenyl)-4-(3,4,5-trimethoxyphenyl)-1,4-butanediol (11.8 g, 21.5 mmol) in chloroform (100 mL) at 0° C. was added dropwise trifluoroacetic acid (9.82 g, 86.1 mmol) in chloroform (100 mL) over 30 minutes. The solution was stirred at 0° C. for 2 hours and then at room temperature for 1 hour. The reaction mixture was quenched with 1N NaOH and chloroform (100 mL) was added. The organic layer was washed with 1N NaOH solution, water and saturated NaCl solution, and then dried over $MgSO_4$, filtered and evaporated in vacuo to an oil which was a cis and trans mixture. The trans isomer was isolated by column chromatography (silica, 1:1 hexane/ethyl acetate) (4.7 g, 41.4%) as the faster eluting isomer. $^1$H NMR ($CDCl_3$) δ1.99 (m, 2 H); 2.47 (m, 2 H); 3.83 (t, 2 H); 3.84 (s, 3 H); 3.87 (s, 3 H); 3.89 (s, 6 H); 4.16 (t, 2 H); 5.18 (m, 2 H); 6.62 (s, 2 H); 6.96 (d, 1 H); 7.39 (d, 1 H).

Trans-2-(3-methoxy-4-methylsulfoxyethoxy-5-iodophenyl)-5-(3,4,5-trimethoxyphenyl) tetrahydrofuran (compound 108).

To the solution of trans-2-(3-methoxy-4-hydroxyethoxy-5-iodophenyl)-5-(3,4,5-trimethoxyphenyl)tetrahydrofuran (4.7 g, 8.87 mmol) in dichloromethane (50 mL) at 0° C. was added methylsulfonyl chloride (3.05 g, 26.6 mmole) and triethylamine (2.69 g, 26.60 mmol). The reaction mixture was stirred at 0° C. for 2 hours and room temperature overnight. The solvent was evaporated in vacuo and the residue purified by column chromatography (silica, 1:1 hexane/ethyl acetate) (4.17 g, 77.3%). $^1$H NMR ($CDCl_3$) δ1.98 (m, 2 H); 2.45 (m, 2 H); 3.15 (s, 3 H); 3.84 (s, 3 H); 3.88 (s, 9 H); 4.26 (t, 2 H); 4.61 (t, 2 H); 5.17 (m, 2 H); 6.62 (s, 2 H); 6.96 (d, 1 H); 7.38 (d, 1 H).

Preparation of trans-2-[4-(2-(N'-hydroxy-N'-substituted ureidyl)ethoxy)3-methoxy-5-methylsulfonylphenyl]-5-(3,4,5-trimethoxyphenyl)-tetrahydrofuran (compounds 1–3, scheme 1)

Trans-2-[4-(2-hydroxyethoxy)-3-methoxy-5-methylthio phenyl]-5-(3,4,5-trimethoxyphenyl)tetrahydrofuran (compound 202, scheme 1)

To a solution of trans-2-(4-(2-hydroxy ethoxy)-3-methoxy-5-iodophenyl]-5-(3,4,5-trimethoxyphenyl) tetrahydrofuran (201) (6.78 g, 12.79 mmol) in 80 mL of DMF was added copper powder (6.91 g, 108.74 mmol) and dimethyldisulfide (2.3 mL, 25.58 mmol). The reaction was heated at 140° C. for 20 hours. The mixture was then cooled, filtered and washed with ethyl acetate. Water was added to the filtrate and the mixture was extracted with ethyl acetate. The organic layer was washed three times with water, dried over magnesium sulfate, filtered and evaporated in vacuo to an oil which was purified by flash column chromatography (silica gel, 1:1 hexane/ethyl acetate) (5.2 g, 90.3%). $^1$H NMR ($CDCl_3$) δ1.99 (m, 2 H); 2.46 (s, 3 H); 2.47 (m, 2H; 3.79 (m, 2 H); 3.83 (s, 3 H); 3.84 (s, 3 H); 3.88 (s, 6 H); 4.20 (t, 2 H); 5.20 (m, 2 H); 6.61 (s, 2 H); 6.82 (s, 2 H).

Trans-2-[4-(2-hydroxyethoxy)-3-methoxy-5-methylsulfonylphonyl]-5(3,4,5-trimethoxyphenyl) tetrahydrofuran (compound 203, scheme 1)

A suspension of magnesium monoperoxyphthalic acid (10.4 g, 20.95 mmol) in 30 mL of water was added to 202 (5.03 g, 11.18 mmol) in 80 mL of acetonitrile. The reaction mixture was stirred at room temperature for 3 hours and then water was added and the mixture was extracted with ethyl acetate. The organic layer was washed with 10% sodium carbonate solution, water and saturated sodium chloride solution, dried over magnesium sulfate and evaporated to provide the product (5 g, 92.8%). $^1$H NMR (CDCl$_3$) δ2.00 (m, 2 H); (m, 2 H); 3.26 (s, 2 H); 3.84 (s, 3 H); 3.87 (m, 2 H); 3.88 (s, 6 H), (s, 3 H); 4.44 (m, 2 H); 5.22 (m, 2 H); 6.61 (s, 2 H); 7.31 (d, 1 H); 7.53 (d, 1 H).

Trans-2-[4-(2-methylsulfoxyethoxy)-3-methoxy-6-methylsulfonyl-phenyl]-5-(3,4,5-trimethoxyphenyl) tetrahydrofuran (compound 204, scheme 1)

To a solution of 203 (5 g, 10.37 mmol) in 30 mL dichloromethane at 0° C. was added methanesulfonyl chloride (1.78 g, 15.56 mmol) and triethylamine (2.36 g, 23.34 mmol). The reaction mixture was stirred at room temperature for 3 hours. The solvent was evaporated in vacuo and the residue purified by flash column chromatography (silica, 1:1 hexane/ethyl acetate) (4.82 g, 83.0%). $^1$H NMR (CDCl$_3$) δ1.99 (m, 2 H); 2.48 (m, 2 H); 3.12 (s, 3 H); 3.26 (s, 3 H); 3.83 (s, 3 H); 3.88 (s, 6 H); 3.92 (s. 3 H); 4.42 (t, 2 H); 4.61 (t, 2 H); 5.22 (m, 2 H); 6.60 (t, 2 H); 7.31 (d, 1 H); 7.51 (d, 1 H).

Trans-2-[4-(2-phthalimidylethoxy)-3-methoxy-5-methylsulfonylphenyl]-5-(3,4,5-trimethoxyphenyl) tetrahydrofuran (compound 205, scheme 1)

To a solution of 204 (500 mg, 0.89 mmol) in 25 mL ethanol was added potassium carbonate (122.3 mg, 0.88 mmol) and phthalimide potassium salt (248 mg, 1.34 mmol). The reaction mixture was refluxed for 16 hours. The reaction was quenched with water and extracted with ethyl acetate. The organic layer was washed with water and saturated sodium chloride solution, dried over magnesium sulfate, filtered and evaporated to an oil which was purified by flash column chromatography (silica, 1:1 hexane/ethyl acetate) (410 mg, 75.2%). $^1$H NMR (CDCl$_3$) δ1.99 (m, 2 H); 2.46 (m, 2 H); 3.28 (s. 3 H); (s, 3 H); 3.88 (s, 6 H); 3.91 (s, 3 H); 4.15 (t, 2 H); 4.32 (t, 2 H); (m, 2 H); 6.61 (s, 2 H); 7.20 (d, 1 H); 7.51 (d, 1 H); 7.73 (m, 2 H); 7.87 (m, 2 H).

Trans-2-[4-(2-aminoethoxy)-3-methoxy-5-methylsulfonylphenyl]-5-(3,4,5-trimethoxyphenyl) tetrahydrofuran (compound 206, scheme 1)

To a solution of 205 (100 mg, 0.16 mmol) in 5 mL ethanol was added hydrazine monohydrate (52.5 mg, 1.64 mmol). The reaction mixture was refluxed for 20 hours. The reaction was quenched with water and extracted with ethyl acetate. The organic layer was washed with water and saturated sodium chloride solution, dried over magnesium sulfate, filtered and evaporated to provide product. $^1$H NMR (CDCl$_3$) δ1.99 (m, 2 H); 2.49 (m, 2 H); 3.12 (m, 2 H); 3.26 (3, 3 H); 3.83 (s, 3 H); 3.88 (s, 6 H); 3.92 (s, 3 H); 4.24 (t, 2 H); 5.21 (m, 2 H); 6.61 (s, 2 H); 7.29 (d, 1 H); 7.51 (d, 1 H).

Trans-2-[4-(2-(N'-methyl-N'-hydroxyureidyl)ethoxy)-3-methoxy-5-methylsulfonylphenyl]-5-(3,4,5-trimethoxyphenyl)tetrohydrofuran (compound 1, scheme 1)

To a solution of 206 (20 mg, 0.042 mmol) in 3 mL dichloromethane was added triphosgene (4.1 mg, 0.014 mmol) and triethylamine (4.2 mg, 0.042 mmol). The reaction mixture was refluxed for 2 hours and then cooled with an ice both. To this cold solution was added triethylamine (18.9 mg, 0.187 mmol) and methylhydroxyamine hydrochloride (10.4 mg, 0.125 mmol). The reaction mixture was stirred at room temperature overnight, and solvent was evaporated in vacuo. The product was isolated by flash column chromatography (silica, ethyl acetate) (17 mg, 73.9%). $^1$H NMR (CDCl$_3$) δ2.00 (m, 2 H); 2.49 (m, 2 H); 3.17 (s, 3 H); 3.24 (2, 3 H); 3.64, m, 2 H); 3.85 (s, 3 H); 3.89 (s, 6 H); 3.94 (s, 3 H); 4.38 (t, 2 H); 5.22 (m, 2 H); 6.49 (s, I H); 6.62 (s, 2 H); 6.85 (t, 1 H); 7.29 (d. 1 H); 7.52 (d, 1 H).

Trans-2-[4-(2-(N'-butyl-N'-hydrozyureidyl) ethoxy)-3-methoxy-5-methylsulfonylphenyl]-5-(3,4,5-trimethozyphenyl)tetrahydrofuran (compound 2, scheme 1)

To a solution of 206 (36 mg, 0.075 mmol) in 3 mL dichloromethane was added triphosgene (7.3 mg, 0.025 mmol) and triethylamine (7.6 mg, 0.075 mmol). The reaction mixture was refluxed for 2 hours and then cooled with ice both. To this cold solution was added triethylamine (34.1 mg, 0.34 mmol) and butylhydroxyamine hydrochloride (28.1 mg, 0.22 mmol). The reaction mixture was stirred at room temperature overnight, and the solvent was evaporated in vacuo. The product was isolated by flash column chromatography (silica, ethyl acetate) (17 mg, 73.9%). $^1$H NMR (CDCl$_3$) δ0.94 (t, 3 H); 1.34 (m, 2 H); 1.59 (m, 2 H); 2.00 (m, 2 H); 2.49 (m, 2 H); 3.24 (s, 3 H); 3.51 (t, 2 H); 3.65 (m, 2 H); 3.84 (s, 3 H); 3.89 (s, 6 H); 3.93 (s, 3 H); 4.38 (t, 2 H); 5.22 (m, 2 H); 6.62 (s, 2 H); 6.82 (t, 1 H); 7.29 (d, 1 H); 7.51 (d, 1 H).

Trans-2-[4-(2-(N'-butyl-N'-cyclohexanyl-N'-hydroxy) ureidylethoxy)-3-methoxy-5-methylsulfonylphenyl]-5-(3,4,5-trimethoxyphenyl)tetrahydrofuran (compound 3, scheme 1)

To a solution of 206 (36 mg, 0.075 mmol) in 3 mL dichloromethane was added triphosgene (7.3 mg, 0.025 mmol) and triethylamine (7.6 mg, 0.075 mmol). The reaction mixture was refluxed for 2 hours and then cooled with ice bath. To this cold solution was added triethylamine (34.1 mg, 0.34 mmol) and cyclohexylhydroxyamine hydrochloride (34.0 mg, 0.22 mmol). The reaction mixture was stirred at room temperature overnight, and the solvent was evaporated in vacuo. The product was isolated by flash column chromatography (silica, ethyl acetate) (22 mg, 47.2%). $^1$H NMR (CDCl$_3$) δ1.12–1.96 (m, 10 H); 2.82 (m, 1 H); 2.00 (m, 2 H); 2.50 (m, 2 H); 3.25 (s, 3 H); 3.66 (m, 2 H); 3.85 (s, 3 H); 3.89 (s, 6 H); 3.94 (s, 3 H); 4.38 (t, 2 H); 5.23 (m, 2 H); 6.62 (s, 2 H); 6.86 (t, 1 H); 7.29 (d, 1 H); 7.53 (d, 1 H).

EXAMPLE 2

Preparation of trans-2-[4-(2-(N-hydroxy-N'-substituted ureidyl)ethoxy)-3-methoxy-5-methylsulfonylphenyl]-5-(3,4,5-trimethoxyphenyl)tetrahydrofuran (compounds 4–6. scheme 1)

Trans-2-[4-(2-N-hydroxyaminoethoxy)-3-methoxy-5-methylsulfonyl-phenyl]-5-(3,4,5-trimethoxyphenyl) tetrahydrofuran (compound 207, scheme 1)

To a solution of 204 (930 mg, 1.66 mmol) in 10 mL ethanol was added sodium carbonate (396 mg, 3.74 mmol) and hydroxylamine hydrochloride (173.1 mg, 2.49 mmol). The reaction mixture was refluxed for 16 hours, cooled to room temperature, quenched with water and extracted with ethyl acetate. The organic layer was washed with water and saturated sodium chloride solution, dried over magnesium sulfate, filtered and evaporated in vacuo to provide the named product (800 mg, 97.0%). $^1$H NMR (CDCl$_3$) δ2.00 (m, 2 H); 2.49 (m, 2 H); 3.26 (m, 2 H); 3.36 (m, 2 H); 3.83 (s, 3 H); 3.88 (s, 6 H); 3.92 (s, 3 H); 4.40 (m, 2 H); 5.21 (m, 2 H); 6.61 (s, 2 H); 7.30 (d, 1 H); 7.51 (d, 1 H).

Trans-2-[4-(2-(N-hydroxy-N'-hydrogen ureidyl) ethoxy)-3-methoxy-5-methylsulfonylphenyl]-5-(3,4,5-trimethoxyphenyl)tetrahydrofuran (compound 4, scheme 1)

To a solution of 207 (50 mg, 1.66 mmol) in 1 mL dichloromethane was added trimethylsilyl-isocyanate (11.6 mg, 0.101 mmol). The reaction was stirred at room temperature for 30 minutes. Saturated ammonium chloride solution was added to the reaction mixture and it was extracted with ethyl acetate. The organic layer was washed with saturated sodium chloride solution, dried over magnesium, sulfate, filtered and evaporated in vacuo to an oil which was purified by flash column chromatography (silica, ethyl acetate) (35 mg, 64.9%). $^1$H NMR (CDCl$_3$) δ2.02 (m, 2 H); 2.51 (m, 2 H); 3.32 (s, 3 H); 3.85 (s, 3 H); 3.89 (s, 6 H); 3.95 (s, 3 H); 3.98 (t, 2 H); 4.38 (t, 2 H); 5.22 (m, 2 H); 6.62 (s, 2 H); 7.32 (d, 1 H); 7.52 (d, 1 H); 7.97 (s, 1 H).

Trans-2-[4-(2-(N-hydroxy-N'-methylureidyl)ethoxy)-3-methoxy-5-methylsulfonylphenyl]-5-(3,4,5-trimethozyphenyl) tetrahydrofuran (compound 5, scheme 1)

To a solution of 207 (50 mg, 0.101 mmol) in 0.5 mL dichloromethane was added methyl isocyanate (5.7 mg, 0.101 mmol). The reaction mixture was stirred at room temperature for 30 minutes. Saturated ammonium chloride solution was added and the mixture was extracted with ethyl acetate. The organic layer was washed with saturated sodium chloride solution, dried over magnesium sulfate, filtered and evaporated in vacuo to an oil which was purified by flash column chromatography (silica, ethyl acetate) (42 mg, 75.4%). $^1$H NMR (CDCl$_3$) 51.99 (m, 2 H); 2.48 (m, 2 H); 2.85 (d, 3 H); 3.29 Is, 3 H); 3.82 (s, 3 H); 3.87 (s, 6 H); 3.91 (m, 2 H); 3.92 (s, 3 H); 4.35 (t, 2 H); 5.20 (m, 2 H); 6.01 (t, 1 H); 6.60 (s, 2 H); 7.29 (d, 1 H); 7.49 (d, 1 H); 7.74 (s, 1 H).

Trans-2-[4-(2-(N-hydroxy-N'-propylureidyl) ethoxy)-3-methoxy-5-methylsulfonylphenyl]-5-(3,4,5-trimethoxyphenyl)tetrahydrofuran (compound 6, scheme 1)

To a solution of 207 (40 mg, 0.080 mmol) in 0.5 mL dichloromethane was added propyl isocyanate (6.9 mg, 0.080 mmol). The reaction mixture was stirred at room temperature for 30 minutes. Saturated ammonium chloride solution was added to the reaction and extracted with ethyl acetate. The organic layer was washed with saturated sodium chloride solution, dried over magnesium sulfate, filtered and evaporated in vacuo to an oil which was purified by flash column chromatography (silica, ethyl acetate) (36 mg, 76.9%). $^1$H NMR (CDCl$_3$) δ0.94 (t, 3 H); 1.55 (m, 2 H); 2.00 (m, 2 H); 2.48 (m, 2 H); 3.22 (m, 2 H); 3.30 (s, 3 H); 3.83 (s, 3 H); 3.87 (s, 6 H); 3.92 (m, 2 H); 3.94 (s, 3 H); 4.38 (t, 2 H); 5.25 (m, 2 H); 6.10 (t, 1 H); 6.60 (s, 2 H); 7.30 (d, 1 H); 7.51 (d, 1 H); 7.77 (s, 1 H).

EXAMPLE 3

Preparation of trans-2-[3-(2-(N'-hydroxy-N'-substituted ureidyl)ethoxy)-4-propoxy-5-propylsulfonylphenyl]-5-(3,4,5-trimethoxyphenyl)-tetrahydrofuran (compounds 7–16, scheme 2)

1-(3-Benzyloxy-4-propoxy-5-methylsulfonylphenyl)-4-(3,4,5-trimethoxyphenyl)-1,4-butanediol (compound 209, scheme 2)

208 (15 g, 26.3 mmol) was added to 100 mL tetrahydrofuran and 200 mL methanol. To this solution was added dropwise sodium borohydride (1.79 g, 47.4 mmol) in 50 mL water. The reaction mixture was stirred at room temperature for 2.5 hours, cooled, quenched with water, and the aqueous layer extracted with ethyl acetate. The organic layer was dried over magnesium sulfate, filtered and evaporated in vacuo to provide the named product (15.2, 100%). $^1$H NMR (CDCl$_3$) δ0.98 (t, 3 H); 2.85 (m, 6 H); 3.25 (s, 3 H); 3.83 (s, 3 H); 3.88 (s, 6 H); 4.15 (t, 2 H); 4,72 (m, 2 H); 5.23 (s, 2 H); 6.57 (s, 2 H); 7.32 (d, 1 H); 7.43 (m, 4 H); 7.48 (d, 1 H).

Trans-2-(3-benzyloxy-4-propoxy-5-methylsulfonylphenyl)-5-(3,4,5-trimethoxyphenyl) tetrahydrofuran (compound 210, scheme 2)

To a solution of 209 (7 g, 12.2 mmol) in 38 mL chloroform at 0° C. was added dropwise trifluoroacetic acid (5.58 g, 48.9 mmol) in 38 mL chloroform over 20 minutes. The reaction mixture was stirred at 0° C. for 2 hours and then at room temperature for 2 hours. The reaction mixture was then quenched with 10% NAOH solution, extracted with dichloromethane and the organic layer was washed with 10% sodium chloride solution, water and saturated sodium chloride solution, and then dried over magnesium sulfate, filtered and evaporated in vacuo to provide a cis and trans mixture. The trans isomer was isolated by flash column chromatography (silica, 2:1 hexane/ethyl acetate) (2.76 g, 40.7%). $^1$H NMR (CDCl$_3$) δ1.00 (t, 3 H); 1.85 (m, 2 H); 1.99 (m, 2 H); 2.48 (m, 2 H); 3.27 (s, 3 H); 3.83 (s, 3 H); 3.88 (s, 6 H); 4.1 6 (t, 2 H); 5.17 (s, 2 H); 5.22 (m, 2 H); 6.61 (s, 2 H); 7.36 (d, 1 H); 7.43 (m, 4 H); 7.54 (d, 2 H).

Trans-2-(3-benzyloxy-4-propoxy-5-propylsulfonylphenyl)-5-(3,4,5-trimethozyphenyl) tetrahydrofuran (compound 211, scheme 2)

To a stirred solution of 210 (1 g, 1.80 mmol) in 4 mL dry THF at −78° C. was added dropwise lithium bis (trimethylsilyl)amide (4.17 mL, 4.17 mmol). After 20 minutes at this temperature, iodoethane (2.14 g, 13.75 mmol) was added dropwise, and after an additional 1.5 hour, water was added. The reaction mixture was warmed to room temperature, and the product was isolated by flash column chromatography (silica, 2:1 hexane/ethyl acetate, 0.9 g, 85.7%). $^1$H NMR (CDCl$_3$) δ1.00 (t, 3 H); 1.01 (t, 3 H); 1.74 (m, 2 H); 1.85 (m, 2 H); 1.99 (m, 2 H); 2.47 (m, 2 H); 3.40 (m, 2 H); 3.84 (3, 3 H); 3.88 (s, 6 H); 4.16 (t, 2 H); 5.16 (9, 2 H); 5.21 (m, 2 H); 6.61 (s, 2 H); 7.36 (d, 1 H); 7.42 (m, 4 H); 7.51 (d, 1 H).

Trans-2-(3-hydroxy-4-propoxy-5-propylsulfonylphenyl)-5-(3,4,5-trimethoxyphenyl) tetrahydrofuran (compound 212, scheme 2)

A solution of 211 (1 g, 1.71 mmol) in 15 mL ethyl acetate was hydrogenated over 10% palladium-on-charcoal (200 mg) at balloon pressure for 1.5 hour. The catalyst was filtered off over Celite, and the filtrate was evaporated in vacuo to give the product (910 mg, 108%). $^1$H NMR (CDCl$_3$) δ1.00 (t, 3 H); 1.10 (t, 3 H); 1.72 (m, 2 H); 1.91 (m, 2 H); 1.99 (m, 2 H); 2.48 (m, 2 H); 3.34 (m, 2 H); 3.82 (m, 2 H); 3.84 (s, 3 H); 3.88 (s, 6 H); 4.12 (t, 2 H); 5.21 (m, 2 H); 6.61 (s, 2 H); 7.32 (d, 1 H); 7.49 (d, 1 H).

Trans-2-[3-(2-(N-benzyloxycarbonylamino)ethoxy)-4-propoxy-5-propylsulfonylphenyl]-5-(3,4,5-trimethoxyphenyl)tetrahydrofuran (compound 213, scheme 2)

To a solution of 212 (910 mg, 1.84 mmol) in 5 mL DMF was added potassium carbonate (754 mg, 5.46 mmol) and the 2-bromo-1(N-benzyloxycarbonyl) ethylamine (564 mg, 2.18 mmol) (the reagent was prepared as described below). The reaction mixture was stirred at 40° C. for 20 hours. The reaction was quenched with water and extracted with ethyl acetate. The organic layer was washed with water and saturated sodium chloride solution, dried over magnesium sulfate, filters d and evaporated in vacuo. The product was purified by flash column chromatography (silica, 1:1 hexane/ethyl acetate) (1.01 g, 82.1%). $^1$H NMR (CDCl$_3$) δ1.00 (t, 3 H); 1.05 (t, 3 H); 1.72 (m, 2 H); 1.86 (m, 2 H); 1.99 (m, 2 H); 2.49 (m, 2 H); 3.37 (m, 2 H); 3.68 (m, 2 H); 4.10 (t, 2 H); 4.15 (t, 2 H); 5.12 (s, 2 H); 5.20 (m, 2 H); 6.61 (s, 2 H); 7.28 (d, 1 H); 7.51 (d, 1 H).

Preparation of the 2-bromo-1(N-benzyloxycarbonyl) ethylamine: (compound 216)

2-Bromoethylamine hydrobromide (2 g, 9.76 mmol) was dissolved in 2N sodium hydroxide solution (1.37 g, 34.16 mmol) and cooled with ice bath. To this cold solution was added benzyl chloroformate (1.83 g, 10.98 mmol) dropwise. The reaction mixture was stirred at 0° C. for 2 hours and then warmed to room temperature and stirred at that temperature for 2 hours. The reaction mixture was extracted with ethyl acetate. The organic layer was washed with water, saturated sodium chloride solution, dried over magnesium sulfate, filtered and evaporated in vacuo to provide product (2.1 g, 84%). $^1$H NMR (CDCl$_3$) δ3.48 (t, 2 H); 3.61 (t, 2 H); 5.13 (s, 2 H); 5.20 (bs, 1 H); 7.37 (m, 4 H).

Trans-2-[3-(2-aminoethoxy)-4-propoxy-5-propylsulfonylphenyl]-5-(3,4,5-trimethoxyphenyl) tetrahydrofuran (compound 214, scheme 2)

A solution of 213 (500 mg, 0.75 mmol) in 10 mL ethyl acetate was hydrogenated over 10% palladium-on charcoal (100 mg) at balloon pressure for 2 hours. The catalyst was filtered off over Celite, and the filtrate was evaporated in vacuo to give the product (360 mg, 90%). $^1$H NMR (CDCl$_3$) δ1.01 (t, 3 H); 1.08 (t, 3 H); 1.74 (m, 2 H); 1.90 (m, 2 H); 2.00 (m, 2 H); 2.49 (m, 2 H) 3.17 (t, 2 H); 3.40 (m, 2 H); 3.84 (s, 3 H); 3.88 (s, 6 H); 4.12 (m, 4 H); 5.22 (m, 2 H); 6.61 (8, 2 H); 7.30 (d, 1 H); 7.50 (d, 1 H).

Trans-2-[3-(2-(N'-(1-methylpropyn-2-yl)-N'-hydroxyureidyl)ethoxy)-4-propoxy-5-propylsulfonylphenyl]-5-(3,4,5-trimethoxyphenyl) tetrahydrofuran (compound 7, scheme 2)

214 (170 mg, 0.317 mmol) was dissolved in 4 mL dry dichloromethane. To this solution was added triphosgene (31 mg, 0.105 mmol) and triethylamine (32 mg, 0.317 mmol). The reaction mixture was refluxed for 2 hours and then cooled with ice bath. To this cold solution was added 3-butynyl-2-hydroxylamine 153.8 mg, 0.633 mmol) (preparation of the reagent was described below). The reaction mixture was stirred at room temperature overnight, and then quenched with water and extracted with ethyl acetate. The organic layer was washed with water and saturated sodium chloride solution, dried over magnesium sulfate, filtered and evaporated in vacuo. The product was purified by flash column chromatography (silica, ethyl acetate) (180.5 mg, 87.9%). $^1$H NMR (CDCl$_3$) δ1.06 (t, 3H; t, 3 H); 1.35 (d, d, 3 H); 1.74 (m, 2 H); 1.86 (m, 2 H); 2.00 (m, 2 H); 2.22 (m, 1 H); 2.48 (m, 2 H); 3.38 (m, 2 H); 3.71 (m, 2 H); 3.84 (s, 3 H); 3.89 (s, 6 H); 4.11 (t, 2 H); 4.20 (m, 2 H); 5.05 (m, 1 H); 5.21 (m, 2 H); 6.46 (t, 1 H); 6.52 (bs, 1 H); 6.61 (s, 2 H); 7.30 (d, 1 H); 7.50 (d, 1 H).

Preparation of 3-butynyl-2-hydroxylamine:

To a solution of 3-butyn-2-ol (3 g, 42.8 mmol) in 6 mL dichloromethane was added methanesulfonyl chloride (4.9 g, 42.8 mmol) dropwise at 0° C. The reaction mixture was stirred at room temperature for 2 hours, quenched with water, and extracted with dichloromethane. The organic layer was dried with magnesium sulfate, filtered and evaporated in vacuo to an oil. After drying on vacuum pump for 30 minutes, the oil was dissolved in 10 mL dichloromethane. To this solution was added hydroxylamine hydrochloride (4.5 g, 64.20 mmol) and triethylamine (7.8 g, 77.04 mmol). This reaction mixture was refluxed for 2 hours, quenched with water, and extracted with dichloromethane. The organic layer was washed with saturated sodium chloride solution, dried over magnesium sulfate and evaporated in vacuo to an oil which was purified by flash column chromatography (silica, 1:1 hexane/ethyl acetate). $^1$H NMR (CDCl$_3$) δ1.40 (d, 3 H); 2.35 (s, 1 H); 3.88 (q, 1 H); 5.13 (bs, 1 H); 5.63 (bs, 1 H).

Trans-2-[3-(2-(N'-(propyn-2-yl)-N'-hydroxyureidyl) ethoxy)-4-propoxy-5-propylsulfonylphenyl]-5-(3,4,5-trimethoxyphenyl) tetrahydrofuran (compound 8, scheme 2)

214 (50 mg, 0.093 mmol) was dissolved in 3 mL dry dichloromethane. To this solution was added triphosgene (9.1 mg, 0.031 mmol) and triethylamine (9.4 mg, 0.093 mmol). The reaction mixture was refluxed for 2 hours and then cooled with an ice bath. To this cold solution was added 2-propynyl hydroxylamine (10.2 mg, 0.186 mmol) (preparation of the reagent was as described below). The reaction mixture was stirred at room temperature overnight, quenched with water and extracted with ethyl acetate. The organic layer was washed with water and saturated sodium chloride solution, dried over magnesium sulfate, filtered and evaporated in vacuo. The product was purified by flash column chromatography (silica, ethyl acetate) (16 mg, 27%). $^1$H NMR (CDCl$_3$) δ1.01 (t, 3 H); 1.06 (t, 3 H); 1.75 (m, 2 H); 1.87 (m, 2 H); 2.00 (m, 2 H); 2.19 (s, 1 H); 2.49 (m, 2 H); 3.38 (m, 2 H); 3.71 (m, 2 H); 3.84 (s, 3 H); 3.89 (s, 6 H); 4.13 (m, 4 H); 4.21 (t, 2 H); 5.21 (m, 2 H); 6.45 (t, 1 H); 6.61 (s, 2 H); 7.31 (d, 1 H); 7.50 (d, 1 H).

Preparation of 2-propynylhydroxyamine:

To a solution of propargyl alcohol (5 g, 89.2 mmol) in 10 mL dichloromethane was added methanesulfonyl chloride (11.2 g, 98.1 mmol) dropwise at 0° C. The reaction mixture was stirred at room temperature for 2.5 hours, then quenched with water, and extracted with dichloromethane. The organic layer was dried with magnesium sulfate, filtered and evaporated in vacuo to an oil. After drying on a vacuum pump for 30 minutes, the oil was dissolved in 5 mL dichloromethane. To this solution was added hydroxylamine hydrochloride (12.4 g, 178.4 mmol) and triethylamine (45.1 g, 445.9 mmol). This reaction mixture was refluxed for 2 hours and then quenched with water, and extracted with dichloromethane. The organic layer was washed with saturated sodium chloride solution and dried over magnesium sulfate and evaporated in vacuo to an oil which was purified by flash column chromatography (silica, 1:1 hexane/ethyl acetate) (100 mg).

Trans-2-[3-(2-(N'-(1-methylpropen-2-yl)-N'-hydroxyureidyl)ethoxy)-4-propoxy-5-propylsulfonylphenyl]-5-(3,4,5-trimethoxyphenyl) tetrahydrofuran (compound 9, scheme 2)

214 (43 mg, 0.080 mmol) was dissolved in 3 mL dry dichloromethane. To this solution was added triphosgene (7.8 mg, 0.026 mmol) and triethylamine (8.1 mg, 0.080 mmol). The reaction mixture was refluxed for 2 hours and then cooled with ice bath. To this cold solution was added 3-buten-2-hydroxylamine (20.9 mg, 0.240 mmol) (preparation of this reagent was as described below). The reaction mixture was stirred at room temperature overnight, and then quenched with ethyl acetate. The organic layer was washed with water and saturated sodium chloride solution, dried over magnesium sulfate, filtered and evaporated in vacuo. The product was purified by preparative TLC (silica, ethyl acetate) (16.6 mg, 31.9%). $^1$H NMR (CDCl$_3$) δ1.01 (t, 3 H); 1.03 (t, 3 H); 1.20 (m, 3 H); 1.70 (m, 2 H); 1.85 (m, 2 H); 2.00 (m, 2 H); 2.47 (m, 2 H); 3.37 (m, 2 H); 3.79 (t, 2 H); 3.83 (s, 3 H); 3.88 (s, 6 H); 3.95 (m, 1 H); 4.10 (t, 2 H); 4.18 (t, 2 H); 5.20 (m, 2 H); 5.45 (m, 1 H); 5.65 (m, 1 H); 5.80 (m, 1 H); 6.36 (t, 1 H); 6.60 (a, 2 H); 7.29 (d, 1 H); 7.50 (d, 1 H).

Preparation of 3-buten-2-hydroxylamine:

To a solution of 3-buten-2-ol (1 g, 13.9 mmol) in 5 mL dichloromethane was added methanesulfonyl chloride (1.75 g, 15.3 mmol) dropwise at 0° C. the reaction mixture was stirred at room temperature for 2 hours and then quenched with water, extracted with dichloromethane. The organic layer was dried with magnesium sulfate, filtered and evaporated in vacuo to an oil. After dried on vacuum pump for 30 minutes, the oil was dissolved in 5 mL dichloromethane. To this solution was added hydroxylamine hydrochloride (2.89 g, 41.6 mmol) and triethylamine (10.5 g, 104.0 mmol). The reaction mixture was refluxed for 16 hours, then quenched with water, and extracted with dichloromethane. The organic layer was dried over magnesium sulfate and evaporated in vacuo to provide the product (100 mg).
Trans-2-[3-(2-(N'-(1-methylpropyl)-N'-hydroxyureidyl) ethoxy)-4-propoxy-5-propylsulfonylphenyl]-5-(3,4,5-trimethoxyphenyl)-tetrahydrofuran (compound 10, scheme 2)

A solution of 7 (30 mg, 0.046 mmol) in 2 mL ethyl acetate was hydrogenated over 10% palladium-on charcoal (5 mg) for 3 hours. The catalyst was filtered off over Celite, and the filtrate war, evaporated in vacuo to give the product (19.8 mg, 66%). $^1$H NMR (CDCl$_3$) δ0.84 (t, 3 H); 1.04 (m, 9 H); 1.40 (m, 1 H); 1.51 (m, 1 H); 1.73 (m, 2 H); 1.87 (m, 2 H); 1.99 (m, 2 H); 2.48 (m, 2 H); 3.38 (m, 2 H); 3.68 (m, 2 H); 3.84 (s, 3 H); 3.88 (s, 6 H); 4.11 (m, 3 H); 4.18 (t, 2 H); 5.21 (m, 2 H); 6.10 (in, 1 H); 6.33 (t, 1 H); 6.61 (s, 2 H); 7.30 (d, 1 H); 7.50 (d, 1 H).

Trans-2-[3-(2-(N'-(N'-hydroxyureidyl)ethoxy)-4-propoxy-5-propylsulfonylphenyl]-5-(3,4,5-trimethoxyphenyl) tetrahydrofuran (compound 11, scheme 2)

214 (170 mg, 0.317 mmol) was dissolved in 4 mL dry dichloromethane. To this solution was added triphosgene (31 mg, 0.105 mmol) and triethylamine (32 mg, 0.317 mmol). The reaction mixture was refluxed for 2 hours and then cooled with an ice bath. To this cold solution was added a solution of hydroxylamine hydrochloride (44 mg, 0.633 mmol) and a mixture of THF (1 mL), water (1 drop), and triethylamine (32 mg). The reaction mixture was stirred at room temperature overnight, the solvent was evaporated, and the reaction quenched with water. The water was then extracted with methylene chloride. The organic layer was washed with water and saturated sodium chloride, dried over magnesium sulfate, filtered and evaporated in vacuo. The product was purified by flash column chromatography (silica, ethyl acetate) (140 mg, 75%). $^1$H NMR (CDCl$_3$) δ7.50 (s, 1 H), 7.25 (s, 1 H), 6.60 (s, 2 H), 5.20 (m, 2 H), 4.15 (m, 4 H), 3.90 (s, 6 H), 3.85 (s, 3 H), 3.70 (m, 2 H), 3.35 (m, 2 H), 2.45, m, 2 H), 1.90 (m, 2 H), 1.70 (m, 2 H), 1.10 (t, 3 H), 0.9 (t, 3 H).

Trans-2-[3-(2-(N'-methyl-N'-hydroxyureidyl) ethoxy)-4-propoxy-5-propylsulfonylphenyl]-5-(3,4,5-trimethoxyphenyl)tetrahydrofuran (compound 12, scheme 2)

The reaction procedure for this compound was similar to that of compound 11, scheme 2, except methyl hydroxylamine hydrochloride was used instead of hydroxylamine hydrochloride (100 mg, 52%). $^1$H NMR (CDCl$_3$) δ7.50 (s, 1 H), 7.25 (s, 1 H), 6.60 (s, 2 H), 5.20 (m, 2 H), 4.20 (m, 2 H), 4.15 (m, 2 H), 3.90 (s, 6 H), 3.85 (s, 3 H), 3.70 (m, 2 H), 3.00 (t, 2 H), 3.05 (s, 3 H), 2.50 (m, 2 H), 2.10-1.60 (m, 6 H), 1.05 (m, 6 H).

For the following compounds the procedure used for compound 11, scheme 2 was followed except the corresponding hydroxylamine hydrochlorides were used. The respective percentage yield and the NMR spectral date are given below.

Compound 13, scheme 2, 110 mg (56%), $^1$H NMR (CDCl$_3$) δ7.50 (s, 1 H), 7.25 (s, 1 H), 6.60 (s, 2 H), 5.20 (m, 2 H), 4,20 (m, 2 H), 4.15 (m, 2 H), 3.90 (s, 6 H), 3.85 (s, 3 H), 3.70 (m, 2 H), 3.35 (m, 2 H), 2.50, m, 2 H), 2.00 (m, 2 H), 1.70 (m, 2 H), 1.05 (m, 9 H).

Compound 14, scheme 2, 85 mg (42%), $^1$H NMR (CDCl$_3$) δ7.50 (s, 1 H), 7.25 (s, 1 H), 6.60 (s, 2 H), 5.20 (m, 2 H), 4.35 (m, 1 H), 4.20 (t, 2 H), 4.10 (t, 2 H), 3.90 (m, 6 H), 3.85 (s, 3 H), 3.70 (m, 2 H), 3.40 (m, 4 H), 2.50 (m, 2 H), 2.00 (m, 2 H), 1.90 (m, 2 H), 1.70 (m, 2 H), 1.00 (m, 12 H).

Compound 15, scheme 2, 120 mg (58%), '1H NMR (CDCl$_3$), δ7.50 (s, 1 H), 7.25 (s, 1 H), 6.60 (s, 2 H), 5.20 (m, 2 H), 4.20 (m, 2 H), 4.10 (m, 2 H), 3.90 (m, 6 H), 3.85 (s, 3 H), 3.70 (m, 2 H), 3.40 (m, 4 H), 2.50, (m, 2 H), 2.00 (m, 2 H), 1.90 (m, 2 H), 1.70 (m, 2 H), 1.5 (m, 2 H), 1.2 (m, 2 H), 1.0 (m, 6 H), 0.80 (m, 3 H)

Compound 16, scheme 2, 79 mg (30%), $^1$H NMR (CDCl$_3$) δ7.75 (m, 1 H), 7.50 (m, 2 H), 7.45 (m, 2 H), 6.60 (s, 2 H), 5.20 (m, 2 H), 4.55 (m, 1 H), 4.15 (m, 4 H), 3.70 (m, 2 H), 3.35 (m, 2 H), 2.50, m, 2 H), 2.00 (m, 3 H), 1.70 (m, 2 H), 1.60 (m, 3 H), 1.05 (m, 3 H).

EXAMPLE 4
Preparation of trans-2-[3-(3-(N'-hydroxy-N'-substituted ureidyl)propoxy)-4-propoxy-5-propylsulfonylphenyl]-5-(3, 4,5-trimethoxyphenyl) tetrahydrofuran (compounds 17–19, scheme 3)
Trans-2-[3-(3-(N-benzyloxycarbonylamino) propoxy)-4-propoxy-5-propylsulfonylphenyl]-5-(3,4,5-trimethoxyphenyl)tetrahydrofuran (compound 217, scheme 3)

To a solution of 212 (150 mg, 0.30 mmol) in 5 mL DMF was added potassium carbonate (155.5 mg, 1.13 mmol) and 3-bromo-1-(N-benzyloxycarbonyl)propylamine (122.4 mg, 0.45 mmol) (this reagent was prepared as described below). The reaction was stirred at 40° C. for 16 hours. The reaction was quenched with water and extracted with ethyl acetate. The organic layer was washed with water and saturated sodium chloride solution, dried over magnesium sulfate, filtered and evaporated in vacuo to an oil which was purified by flash column (silica, 2:1 hexane/ethyl acetate) (149 mg, 72.5%). $^1$H NMR (CDCl$_3$) δ1.00 (t, 3 H); 1.03 (t, 3 H); 1.70 (m, 2 H); 1.84 (m, 2 H); 1.98 (m, 2, H); 2.08 (m, 2 H); 2.47 (m, 2 H); 3.36 (m, 2 H); 3.44 (m, 2 H); 3.84 (s, 3 H); 3.88 (s, 6 H); 4.11 (m, 4 H); 5.10 (s, 2 H); 5.20 (m, 2 H); 6.60 (s, 2 H); 7.25 (d, 1 H); 7.31 (m, 4 H); 7.49 (d, 1 H).

Preparation of the 3-bromo-1-(N-benzyloxycarbonyl) propylamine (compound 220)

3-Bromopropylamine hydrobromide (4 g, 18.27 mmol) was dissolved in 2N sodium hydroxide solution (2.56 g, 63.95 mmol in 30 mL water)) and cooled with an ice bath. To this cold solution was added benzylchloroformate (3.43 g, 20.10 mmol) dropwise. The reaction mixture was warmed to room temperature and stirred at that temperature for 4 hours. The reaction mixture was extracted with ethyl acetate. The organic layer was washed with water, saturated sodium chloride solution, dried over magnesium sulfate, filtered and evaporated in vacuo to provide the named product (4–5 g, 90.2%). $^1$H NMR (CDCl$_3$) δ2.10 (m, 2 H); 3.38 (q, 2 H); 3.46 (t, 2 H); 5.12 (s, 2 H); 7.38 (m, 4 H).

Trans-2-[3-(3-aminopropoxy)-4-propoxy-5-propylsulfonylphenyl]-5-(3,4,5-trimethoxyphenyl) tetrahydrofuran (compound 218, scheme 3)

A solution of 217 (149 mg, 0.22 mmol) in 3 mL ethyl acetate was hydrogenated over 10% palladium-on charcoal (50 mg) at balloon pressure for 2.5 hours. The catalyst was filtered off over Celite, and the filtrate was evaporated in vacuo to give the product (102.4 mg, 85.4%). $^1$H NMR (CDCl$_3$) δ1.00 (t, 3 H); 1.05 (t, 3 H); 1.70 (m, 2 H); 1.87 (m, 2 H); 1.99 (m, 2 H); 2.02 (m, 2 H); 2.18 (bs, 2 H); 2.47 (m, 2 H); 2.96 (t, 2 H); 3.36 (m, 2 H); 3.84 (s, 3 H); 3.88 (s, 6 H); 4.10 (t, 2 H); 4.15 (t, 2 H); 5.20 (m, 2 H); 6.60 (2, 2 H); 7.26 (d, 1 H); 7.46 (d, 1 H).

Trans-2-[3-(3-(N'-methyl-N'-hydrozyureidyl) propoxy)-4-propoxy-5-propylsulfonylphenyl]-5-(3,4,5-trimethoxyphenyl)tetrahydrofuran (compound 17, scheme 3)

218 (34 mg, 0.062 mmol) was dissolved in 2 mL dry dichloromethane. To this solution was added triphosgene (6.0 mg, 0.020 mmol) and triethylamine (6.2 mg, 0.062 mmol). The reaction mixture was refluxed for 2 hours and then cooled with an ice bath. To this cold solution was added methylhydroxyamine hydrochloride (15.5 mg, 0.185 mmol) and triethylamine (28.1 mg, 0.278 mmol). The reaction mixture was stirred at room temperature overnight. The solvent was evaporated in vacuo and the product was purified by preparative TLC (silica, ethyl acetate) (13 mg, 33.7%). $^1$NMR (CDCl$_3$ $\delta$1.01 (t, 3 H); 1.05 (t, 3 H); 1.71 (m, 2 H); 1.88 (m, 2 H); 2.00 (m, 2 H); 2.06 (m, 2 H); 2.49 (m, 2 H); 3.05 (s, 3 H); 3.40 (m, 4 H); 3.84 (s, 3 H); 3.88 (s, 6 H); 4.12 (m, 4 H); 5.21 (m, 2 H); 6.07 (t, 1 H); 6.61 (s, 2 H); 6.95 (s, 1 H); 7.28 (d, 1 H); 7.48 (d, 1 H).

Trans-2-[3-(3-(N'-butyl-N'-hydroxyureidyl) propoxy)-4-propoxy-5-propylsulfonylphenyl]-5-(3,4,5-trimethoxyphenyl)tetrahydrofuran (compound 18, scheme 3)

218 (34 mg, 0.062 mmol) was dissolved in 2 mL dry dichloromethane. To this solution was added triphosgene (6.0 mg, 0.020 mmol) and triethylamine (6.2 mg, 0.062 mmol). The reaction mixture was refluxed for 2 hours and then cooled with an ice bath. To this cold solution was added butylhydroxyamine (16.5 mg, 0.185 mmol). The reaction mixture was stirred at room temperature overnight. The solvent was evaporated in vacuo and the product was purified by preparative TLC (silica, ethyl acetate) (20 mg, 48.7%). $^1$H NMR (CDCl$_3$) $\delta$0.91 (t, 3 H); 1.01 t, 3 H); 1.05 (t, 3 H); 1.30 (m, 2 H); 1.52 (m, 2 H); 1.72 (m, 2 H); 1.86 (m, 2 H); 1.99 (m, 2 H); 2.06 (m, 2 H); 2.48 (m, 2 H); 3.36 (m, 2 H); 3.44 (m, 4 H); 3.84 (s 3 H); 3.88 (s, 6 H); 4.13 (m, 4 H); 5.21 (m, 2 H); 6.04 (t, 1 H); 6.61 (s, 2 H); 7.28 (d, 1 H); 7.49 (d, 1 H).

Trans-2-[3-(3-(N'-(1-methylpropyn-2-yl)-N'-hydroxyureidyl)-propoxy)-4-propoxy-5-propylsulfonylphenyl]-5-(3,4,5-trimethoxyphenyl)-tetrahydrofuran (compound 19, scheme 3)

218 (34 mg, 0.062 mmol) was dissolved in 2 mL dry dichloromethane. To this solution was added triphosgene (6.0 mg, 0.020 mmol) and triethylamine (6.2 mg, 0.062 mmol). The reaction mixture was refluxed for 2 hours and then cooled with an ice bath. To this cold solution was added 3-butynyl-2-hydroxyamine (15.7 mg, 0.185 mmol). The reaction mixture was stirred at room temperature overnight. The solvent was evaporated in vacuo and the product was purified by preparative TLC (silica, ethyl acetate) (30 mg, 73.3%). $^1$H NMR (CDCl$_3$) $\delta$1.02 (t, 3H; t, 3 H); 1.38 (d, d 3 H); 1.72 (m, 2 H); 1.88 (m, 2 H); 1.99 (m, 2 H); 2.07 (m, 2 H); 2.22 (m, 1 H); 2.47 (m, 2 H); 3.38 (m, 2 H); 3.48 (m, 2 H); 3.84 (s, 3 H); 3.88 (s, 6 H); 5.05 (m, 1 H); 5.21 (m, 2 H); 6.28 (t, 1 H); 6.21 (s, 2 H); 7.27 (d, 1 H); 7.48 (d, 1 H).

EXAMPLE 5

Preparation of trans-2-[3-(4-(N'-hydroxy-N'-substituted ureidyl)-2-butenoxy)-4-propoxy-5-methylsulfonylphenyl]-5-(3,4,5-trimethoxyphenyl) tetrahydrofuran (compounds 20–24, scheme 4)

Trans-2-(3-hydroxy-4-propoxy-5-methylsulfonylphenyl)-5-(3,4,5-trimethoxyphenyl) tetrahydrofuran (compound 221, scheme 4)

A solution of 210 (900 mg, 1.62 mmol) in 15 mL ethyl acetate was hydrogenated over 10% palladium-on charcoal (200 mg) at balloon pressure for 1.5 hours. The catalyst was filtered off over Celite, and the filtrate was evaporated in vacuo to give the product (790 mg, 104.7%). $^1$H NNR (CDCl$_3$) $\delta$1.12 (t, 3 H); 1.91 (m, 2 H); 1.99 (m, 2 H); 2.48 (m, 2 H); 3.24 (s, 3 H); 3.84 (s, 3 H); 3.88 (s, 3 H); 4.13 (t, 2 H); 5.21 (m, 2 H); 6.61 (s, 2 H); 7.24 (d, 1 H); 7.51 (d, 1 H).

Trans-2-[3-(4-phthalimidyl-2-butenoxy)-4-propoxy-5-methylsulfonyl-phenyl]-5-(3,4,5-trimethoxyphenyl) tetrahydrofuran (compound 222, scheme 4)

To a solution of 221 (300 mg, 0.65 mmol) in 2 mL DMF was added potassium carbonate (267 mg, 1.93 mmol) and the 4-bromo-1-phthalimidyl-2-butene (270.4 mg, 0.97 mmol) (this reagent was prepared as described below). The reaction was stirred at 40° C. for 16 hours. The reaction was quenched with water and extracted with ethyl acetate. The organic layer was washed with water and saturated sodium chloride solution, dried over magnesium sulfate, filtered and evaporated in vacuo to an oil which was purified by flash column (silica, 1:1 hexane/ethyl acetate) (387.8 mg, 90.6%). $^1$H NMR (CDCl$_3$) $\delta$1.02 (t, 3 H); 1.85 (m, 2 H); 1.97 (m, 2 H); 2.456 (m, 2 H); 3.24 (m, 2 H); 3.84 (s, 3 H); 3.88 (s, 6 H); 4.12 (t, 2 H); 4.36 (d, 2 H); 4.61 (d, 2 H); 5.20 (m, 2 H); 5.97 (m, 2 H); 6.61 (s, 2 H); 7.22 (d, 1 H); 7.51 (d, 1 H); 7.74 (m, 2 H); 7.86 (m, 2 H).

Preparation of 4-bromo-1-phthalimidyl-2-butene (compound 227):

To a solution of 1,4-dibromo-2-butene (5 g, 23.37 mmol) in 4 mL DMF was added phthalimide potassium salt (433 mg, 2.34 mmol). The reaction mixture was stirred at 40° C. for 16 hours. The reaction was quenched with water and extracted with ethyl acetate. The organic layer was washed with water and saturated sodium chloride solution, dried over magnesium sulfate, filtered and evaporated in vacuo to provide the product (250 mg). $^1$H NMR (CDCl$_3$) $\delta$3.92 (d, 2 H); 4.32 (d, 2 H); 5.90 (m, 2 H); 7.74 (m, 2 H); 7.87 (m, 2 H).

Trans-2-[3-(4-amino-2-butenoxy)-4-propoxy-5-methylsulfonylphenyl]-5-(3,4,5-trimethoxyphenyl) tetrahydrofuran (compound 223, scheme 4)

To a solution of 222 (100 mg, 0.15 mmol) in 5 mL ethanol was added hydrazine monohydrate (7.2 mg, 0.23 mmol). The reaction mixture was refluxed for 2 hours and then quenched with water, extracted with ethyl acetate. The organic layer was washed with water and saturated sodium chloride solution, dried over magnesium sulfate, filtered and evaporated in vacuo to provide the product (80 mg, 99.4%). $^1$H NMR (CDCl$_3$) $\delta$1.05 (t, 3 H); 1.89 (m, 2 H); 1.99 (m, 2 H); 2.48 (m, 2 H); 3.24 (s, 3 H); 3.39 (m, 2 H); 3.84 (s, 3 H); 3.88 (s, 6 H); 4.14 (t, 2 H); 4.62 (d, 2 H); 5.21 (m, 2 H); 5.88 (m, 1 H); 6.00 (m, 1 H); 6.61 (s, 2 H); 7.28 (d, 1 H) ; 7.51 (d, 1 H).

Trans-2-[3-(4-(N'-methyl-N'-hydroxyureidyl)-2-butenoxy)-4-propoxy-5-methylsulfonylphenyl]-5-(3,4,5-trimethoxyphenyl)tetrahydrofuran (compound 20, scheme 4)

223 (34 mg, 0.064 mmol) was dissolved in 3 mL dry dichloromethane. To this solution was added triphosgene (6.2 mg, 0.021 mmol) and triethylamine (6.4 mg, 0.064). The reaction mixture was refluxed for 2 hours and then cooled with an ice bath. To this cold solution was added methylhydroxyamine hydrochloride (23.2, 0.229 mmol) and triethylamine (15.9 mg, 0.191 mmol). The reaction mixture was stirred at room temperature overnight, and then quenched with water and extracted with ethyl acetate. The organic layer was washed with water and saturated sodium chloride solution, dried over magnesium sulfate, filtered and evaporated in vacuo. The product was purified by preparative TLC (silica, ethyl acetate) (21 mg, 54.2%). $^1$H NMR (CDCl$_3$) $\delta$1.05 (t, 3 H); 1.87 (m, 2 H); 1.99 (m, 2 H); 2.47 (m, 2 H); 3.06 (s, 3 H); 3.26 (s, 3 H); 3.84 (s, 3 H); 3.87 (m, 2 H); 3.88 (s, 6 H); 4.13 (t, 2 H); 4.62 (d, 2 H); 5.21 (m, 2 H); 5.86 (m, 1 H); 5.99 (m, 1 H); 6.61 (s, 2 H); 6.99 (s, 1 H); 7.23 (d, 1 H); 7.52 (d, 1 H).

Trans-2-[3-(4-(N'-ethyl-N'-hydroxyureidyl)-2-butenoxy)-4-propoxy-5-methylsulfonylphenyl]-5-(3,4,5-trimethoxyphenyl)tetrahydrofuran (compound 21, scheme 4)

223 (40 mg, 0.075 mmol) was dissolved in dry dichloromethane. To this solution was added triphosgene (7.3 mg, 0.025 mmol) and triethylamine (7.6 mg, 0.075 mmol). The reaction mixture was refluxed for 2 hours and then cooled with an ice bath. To this cold solution was added ethylhydroxyamine hydrochloride (21.9 mg, 0.224 mmol) and triethylamine (27.2 mg, 0.269 mmol). The reaction mixture was stirred at room temperature overnight, and then quenched with water and extracted with ethyl acetate. The organic layer was washed with water and saturated sodium chloride solution, dried over magnesium sulfate, filtered and evaporated in vacuo. The product was purified by preparative TLC (silica, ethyl acetate) (25.4 mg, 54.6%). $^1$H NMR (CDCl$_3$) δ1.04 (t, 3 H); 1.08 (t, 3 H); 1.87 (m, 2 H); 1.99 (m, 2 H); 2.47 (m, 2 H); 3.25 (s, 3 H); 3.47 (m, 2 H); 3.84 (s, 3 H); 3.87 (m, 2 H); 3.88 (s, 6 H); 4.12 (t, 2 H); 4.62 (d, 2 H); 5.21 (m, 2 H); 6.86 (m, 2 H); 6.03 (t, 1 H); 6.61 (s, 2 H); 6.78 (bs, 1 H); 7.22 (d, 1 H); 7.51 (d, 1 H).

Trans-2-[3-(4-(N'-butyl-N'-hydroxyureidyl)-2-butenoxy)-4-propoxy-5-methylsulfonylphenyl]-5-(3,4,5-trimethoxyphenyl)tetrahydrofuran (compound 22, scheme 4)

223 (34 mg, 0.064 mmol) was dissolved in 3 mL dry dichloromethane. To this solution was added triphosgene (6.2 mg, 0.021 mmol) and triethylamine (6.4 mg, 0.064 mmol). The reaction mixture was refluxed for 2 hours and then cooled with an ice bath. To this cold solution was added butylhydroxyamine (17.0 mg, 0.191 mmol) The reaction mixture was stirred at room temperature overnight. The solvent was evaporated in vacuo and the product was separated by preparative TLC (silica, ethyl acetate) (20.9 mg, 50.6%). $^1$H NMR (CDCl$_3$) δ0.90 (t, 3 H); 1.05 (t, 3 H); 1.29 (m, 2 H); 1.53 (m, 2 H); 1.88 (m, 2 H); 1.98 (m, 2 H); 2.47 (m, 2 H); 3.25 (s, 3 H); 3.43 (t, 2 H); 3.84 (s, 3 H); 3.87 (m, 2 H); 3.88 (s, 6 H); 4.13 (t, 2 H); 4.62 (d, 2 H); 5.21 (m, 2 H); 5.86 (m, 1 H); 5.98 (m, 1 H); 6.61 (s, 2 H); 7.23 (d, 1 H); 7.52 (d, 1 H).

Trans-2-[3-(4-(N'-(propyn-2-yl)-N'-hydroxyureidyl)-2-butenoxy)-4-propoxy-5-methylsulfonylphonyl]-5-(3,4,5-trimethoxyphenyl)tetrahydrofuran (compound 23, scheme 4)

223 (40 mg, 0.075 mmol) was dissolved in 3 mL dry dichloromethane. To this solution was added triphosgene (7.3 mg, 0.025 mmol) and triethylamine (7.6 mg, 0.075 mmol). The reaction mixture was refluxed for 2 hours and then cooled with an ice bath. To this cold solution was added 2-propynylhydroxyamine (10.6 mg, 0.150 mmol). The reaction mixture was stirred at room temperature overnight. The solvent was evaporated in vacuo and the product was isolated by preparative TLC (silica, ethyl acetate) (20.8 mg, 44.0%). $^1$H NMR (CDCl$_3$) δ1.05 (t, 3 H); 1.88 (m, 2 H); 1.99 (m, 2 H); 1.21 (s, 1 H); 2.48 (m, 2 H); 3.25 (s, 3 H); 3.84 (s, 3 H); 3.87 (m, 2 H); 3.88 (s, 6 H); 4.13 (t, 2 H); 4.20 (m, 2 H); 4.63 (d, 2 H); 5.21 (m, 2 H); 6.08 (m, 2 H); 6.15 (t, 1 H); 6.61 (s, 2 H); 7.22 (d, 1 H); 7.52 (d, 1 H).

Trans-2-[3-(4-(N'-(2,3-dichlorobenzyl)-N'-hydroxyureidyl)-2-butenoxy)-4-propoxy-5-methylsulfonylphenyl]-5-(3,4,5-trimethoxyphenyl) tetrahydrofuran (compound 24, scheme 4)

223 (40 mg, 0.075 mmol) was dissolved in 3 mL dry dichloromethane. To this solution was added triphosgene (7.3 mg, 0.025 mmol) and triethylamine (7.6 mg, 0.075 mmol). The reaction mixture was refluxed for 2 hours and then cooled with an ice bath. To this cold solution was added 2,3-dichlorobenzylhydroxyamine (51.4 mg, 0.224 mmol). The reaction mixture was stirred at room temperature overnight. The solvent was evaporated in vacuo and the product was isolated by preparative TLC (silica, ethyl acetate) (17.8 mg, 31.6%). $^1$H NMR (CDCl$_3$) δ1.04 (t, 3 H); 1.87 (m, 2 H); 1.99 (m, 2 H); 2.47 (m, 2 H); 3.24 (s, 3 H); 3.84 (s, 3 H); 3.87 (m, 2 H); 3.88 (s, 6 H); 4.12 (t, 2 H); 4.52 (d, 2 H); 4.77 (s, 2 H); 5.20 (m, 2 H); 5.86 (m, 2 H); 6.05 (t, 1 H); 6.59 (s, 2 H); 7.14 (m, 1 H); 7.24 (d, 1 H); 7.27 (m, 1 H); 7.36 (m, 1 H); 7.52 (d, 1 H).

EXAMPLE 6

Preparation of trans-2-[3-(4-(N'-amino-N-hydroxyureidyl)-2-butenoxy)-4-propoxy-5-methylsulfonylphenyl]-5-(3,4,5-trimethoxyphenyl) tetrahydrofuran (compound 25, scheme 4)

Trans-2-[3-(4-bromo-2-butenoxy)-4-propoxy-5-methylsulfonylphenyl]-5-(3.4.5-trimethoxyphenyl) tetrahydrofuran (compound 224, scheme 4)

To a solution of 221 (100 mg, 0.21 mmol) in 2 mL DMF was added potassium carbonate (59.3 mg, 0.43 mmol) and the 1,4-dibromo-2-butene (459 mg, 2.15 mmol). The reaction was stirred at room temperature for 16 hours. The reaction was quenched with water and extracted with ethyl acetate. The organic layer was washed with water and saturated sodium chloride solution, dried over magnesium sulfate, filtered and evaporated in vacuo to an oil which was purified by flash column (silica, 2:1 hexane/ethyl acetate) (106 mg, 82.8%). $^1$H NMR (CDCl$_3$) δ1.07 (t, 3 H); 1.89 (m, 2 H); 1.99 (m, 2 H); 2.48 (m, 2 H); 3.25 (s, 3 H); 3.84 (s, 3 H); 3.88 (s, 6 H); 4.00 (d, 2 H); 4.14 (t, 2 H); 4.66 (d, 2 H); 5.21 (m, 2 H); 6.01 (m, 2 H); 6.60 (s, 2 H); 7.26 (d, 1 H); 7.52 (d, 1 H).

Trans-2-[3-(4-hydroxyamino-2-butenoxy)-4-propoxy-5-methylsulfonyl-phenyl]-5-(3,4,5-trimethoxyphenyl) tetrahydrofuran (compound 225, scheme 4)

To a solution of 224 (100 mg, 0.17 mmol) in 5 mL ethanol was added sodium carbonate (68.3 mg, 0.64 mmol) and hydroxyamine hydrochloride (29.9 mg, 0.43 mmol). The reaction was refluxed for 2 hours. The reaction was quenched with water and extracted with ethyl acetate. The organic layer was washed with water and saturated sodium chloride solution, dried over magnesium sulfate, filtered and evaporated in vacuo to provide product (90 mg, 92.0%). $^1$H NMR (CDCl$_3$) δ1.05 (t, 3 H); 1.87 (m, 2 H); 1.99 (m, 2 H); 2.48 (m, 2 H); 3.25 (s, 3 H); 3.32 (m, 2 H); 3.84 (s, 3 H); 3.88 (s, 6 H); 4.12 (t, 2 H); 4.64 (d, 2 H); 5.20 (m, 2 H); 5.90 (m, 2 H); 6.60 (s, 2 H); 7.28 (d, 1 H); 7.50 (d, 1 H).

Trans-2-[3-(4-(N'-amino-N-hydroxyureidyl)-2-butenoxy)-4-propoxy-5-methylsulfonylphenyl]-5-(3,4,5-trimethoxyphenyl)tetrahydrofuran (compound 25, scheme 4)

To a solution of 225 (50 mg, 0.085 mmol) in 0.5 mL dichloromethane was added trimethylsilyl isocyanate (11.8 mg, 0.103 mmol). The reaction was stirred at room temperature for 3 hours. Saturated ammonium chloride solution was added to the reaction and it was extracted with ethyl acetate. The organic layer was washed with saturated sodium chloride solution, dried over magnesium sulfate, filtered and evaporated in vacuo to an oil which was purified by preparative TCL (silica, ethyl acetate) (5.1 mg, 10.0%). $^1$H NMR (CDCl$_3$) δ1.06 (t, 3 H); 1.90 (m, 2 H); 2.01 (m, 2 H); 2.50 (m, 2 H); 3.27 (s, 3 H); 3.51 (m, 1 H); 3.84 (s, 3 H); 3.88 (s, BH); 4.20 (m, 4 H); 4.80 (m, 2 H); 5.21 (m, 2 H); 5.82 (m, 2 H); 6.68 (s, 2 H); 7.20 (s, 1 H); 7.34.

EXAMPLE 7

Preparation of trans-2-[3-(2-(N'-hydroxy-N'-substituted ureidyl)propoxy)-4-propoxy-5-methylsulfonylphenyl]-5-(3,4,5-trimethoxyphenyl) tetrahydrofuran (compounds 26–27, scheme 5)

Trans-2-[3-(propoxy-2-one)-4-propoxy-5-methylsulfonylphenyl]-5-(3,4,5-trimethoxyphenyl) tetrahydrofuran (compound 228, scheme 5)

To a solution of 221 (330 mg, 0.71 mmol) in 4 mL DMF was added potassium carbonate (273.7 mg, 1.98 mmol), chloroacetone (73.3 mg, 0.79 mmol) and tetrabutylammonium iodide (292.5 mg, 0.79 mmol). The reaction mixture was stirred at 40° C. for 16 hours. The reaction was quenched with water and extracted with ethyl acetate. The organic layer was washed with water and saturated sodium chloride solution, dried over magnesium sulfate, filtered and evaporated in vacuo to provide the named product (355 mg, 94.9%). $^1$H NMR (CDCl$_3$) δ1.08 (t, 3 H); 1.92 (m, 2 H); 1.99 (m, 2 H); 2.33 (s, 3 H); 2.49 (m, 2 H); 3.27 (s, 3 H); 3.84 (s, 3 H); 3.88 (s, 6 H); 4.21 (t, 2 H); 4.68 (s, 2 H); 5.20 (m, 2 H); 6.60 (s, 2 H); 7.18 (d, 1 H); 7.60 (d, 1 H).

Trans-2-[3-(propoxy-2-ol)-4-propoxy-5-methylsulfonylphenyl]-5-(3,4,5-trimethoxyphenyl) tetrahydrofuran (compound 229, scheme 5)

228 (350 mg, 0.66 mmol) was added to 1 mL tetrahydrofuran and 2 mL methanol. To this solution was added dropwise sodium borohydride (25.1 mg, 0.66 mmol) in 0.5 mL water. The reaction mixture was stirred at room temperature for 2 hours, and then cooled, quenched with water, and the aqueous layer extracted with ethyl acetate. The organic layer was dried over magnesium sulfate, filtered and evaporated in vacuo to provide the named product (346 mg, 98.5%). $^1$H NMR (CDCl$_3$) δ1.05 (t, 3 H); 1.30 (d, 3 H); 1.78 (m, 2 H); 1.99 (m, 2 H); 2.49 (m, 2 H); 3.23 (s, 3 H); 4.02 (m, 2 H); 4.12 (t, 2 H); 4.22 (m, 1 H); 5.20 (m, 2 H); 6.60 (s, 2 H); 7.28 (d, 1 H); 7.51 (d, 1 H).

Trans-2-[3-(2-phthalimidyl)propoxy)-4-propoxy-5-methylsulfonyl-phenyl]-5-(3,4,5-trimethoxyphenyl) tetrahydrofuran (compound 230, scheme 5)

To a solution of 229 (244 mg, 0.47 mmol), triphenylphosphine (134.4 mg, 0.51 mmol) and phthalimide (82.2 mg, 0.56 mmol) in 5 mL dry THF was added dropwise the diisopropyl azodicarboxylate (100.7 mg, 0.49 mmol). The reaction mixture was stirred at room temperature for 16 hours. The solvent was evaporated in vacuo and the product was isolated by preparative TLC (silica, 1:1 hexane/ethyl acetate) (211 mg, 69.4%). $^1$H NMR (CDCl$_3$) δ0.84 (t, 3 H); 1.25 (d, 3 H); 1.62 (m, 2 H); 1.99 (m, 2 H); 2.48 (m, 2 H); 3.26 (s, 3 H); 3.84 (m, 1 H); 3.88 (s, 6 H); 4.14 (m, 2 H); 4.70 (m, 2 H); 4.88 (m, 1 H); 5.21 (m, 2 H); 6.61 (s, 2 H); 7.28 (m, 1 H); 7.49 (m, 1 H); 7.74 (m, 2 H); 7.84 (m, 2 H).

Trans-2-[3-(2-aminopropoxy)-4-propoxy-5-methylsulfonylphenyl]-5(3,4,5-trimethoxyphenyl) tetrahydrofuran (compound 231, scheme 5)

To a solution of 230 (63 mg, 0.096 mmol) in 3 mL ethanol was added hydrazine monohydrate (4.6 mg, 0.145 mmol). The reaction mixture was refluxed for 3 hours and then quenched with water, extracted with ethyl acetate. The organic layer was washed with water and saturated sodium chloride solution, dried over magnesium sulfate, filtered and evaporated in vacuo to provide the product (44.8 mg, 94.5%). $^1$H NMR (CDCl$_3$) δ1.05 (t, 3 H); 1.25 (d, 3 H); 1.78 (m, 2 H); 1.99 (m, 2 H); 2.48 (m, 2 H); 3.25 (s, 3 H); 3.42 (m, 2 H); 3.84 (8, 3 H); 3.88 (s, 6 H); 3.95 (m, 2 H); 4.12 (t, 2 H); 5.21 (m, 2 H); 6.61 (s, 2 H); 7.28 (d, 1 H); 7.51 (d, 1 H).

Trans-2-[3-(2-(N'-methyl-N'-hydroxyureidyl)-propoxy)-4-propoxy-5-methylsulfonylphenyl]-5-(3,4,5-trimethoxyphenyl)tetrahydrofuran (compound 26, scheme 5)

231 (44.4 mg, 0.090 mmol) was dissolved in 2 mL dry dichloromethane. To this solution was added triphosgene (8.9 mg, 0.030 mmol) and triethylamine (9.2 mg, 0.090 mmol). The reaction mixture was refluxed for 2 hours and then cooled with an ice bath. To this cold solution was added methylhydroxyamine hydrochloride (22.7 mg, 0.271 mmol) and triethylamine (32.9 mg, 0.326 mmol). The reaction mixture was stirred at room temperature overnight, then quenched with water and extracted with dichloromethane. The organic layer was washed with water and saturated sodium chloride solution, dried over magnesium sulfate, filtered and evaporated in vacuo. The product was purified by preparative TLC (silica, ethyl acetate) (17.4 mg, 32.3%). $^1$H NMR (CDCl$_3$) δ1.06 (t, 3 H); 1.35 (t, 3 H); 1.88 (m, 2 H); 2.00 (m, 2 H); 2.49 (m, 2 H); 3.05 (s, s 3 H); 3.25 (s, 3 H); 3.84 (s, 3 H); 3.88 (s, 6 H); 4.12 (m, 4 H); 4.28 (m, 1 H); 5.21 (m, 2 H); 6.04 (m, 1 H); 6.60 (d, 2 H); 7.32 (d, d, 1 H); 7.52 (d, d 1 H).

Trans-2-[3-(2-(N'-butyl-N'-hydroxyureidyl) propoxy)-4-propoxy-5-methylsulfonylphenyl]-5-(3,4,5-trimethoxyphenyl)tetrahydrofuran (compound 27, scheme 5)

231 (45 mg, 0.091 mmol) was dissolved in 2 mL dry dichloromethane. To this solution was added triphosgene (8.9 mg, 0.030 mmol) and triethylamine (9.2 mg, 0.090 mmol). The reaction mixture was refluxed for 2 hours and then cooled with an ice bath. To this cold solution was added butylhydroxyamine (24.5 mg, 0.275 mmol). The reaction mixture was stirred at room temperature overnight. The solvent was evaporated in vacuo and the product was purified by preparative TLC (silica, ethyl acetate) (39.2 mg, 67.0%). $^1$H NMR (CDCl$_3$) δ0.87 (m, 3 H); 1.06 (t, 3 H); 1.25 (m, 2 H); 1.34 (m, 3 H); 1.50 (m, 2 H); 1.88 (m, 2 H); 1.99 (m, 2 H); 2.48 (m, 2 H); 3.24 (s, 3 H); 3.41 (m, 2 H); 3.84 (s, 3 H); 3.88 (s, 6 H); 4.10 (t, 2 H); 4.14 (t, 2 H); 4.26 (m, 1 H); 5.21 (m, 2 H); 6.07 (m, 1 H); 6.60 (s, s, 2 H); 7.31 (d, d 1 H); 7.51 (d, d, 1 H).

EXAMPLE 8

Preparation of trans-2-[3-(2-(N-hydroxy-N'-substituted ureidyl)propoxy)-4-propoxy-5-propylsulfonylphenyl]-5-(3, 4,5-trimethoxyphenyl) tetrahydrofuran (compounds 28–29 scheme 5)

Trans-2-[3-(propoxy-2-one)-4-propoxy-5-propylsulfonylphenyl]-5-(3,4,5-trimethoxyphenyl) tetrahydrofuran (compound 232, scheme 5)

This compound was prepared from 212 in a manner similar to that used for 228. $^1$H NMR (CDCl$_3$) δ1.00 (t, 3 H); 1.05 (t, 3 H); 1.70 (m, 2 H); 1.88 (m, 2 H); 1.98 (m, 2 H); 2.29 (s, 3 H); 2.47 (m, 2 H); 3.36 (m, 2 H); 3.84 (s, 3 H); 3.88 (s, 6 H); 4.25 (t, 2 H); 4.64 (s, 2 H); 5.20 (m, 2 H); 6.60 (s, 2 H); 7.12 (d, 1 H); 7.51 (d, 1 H).

Trans-2-[3-(propoxy-2-ol)-4-propoxy-5-propylsulfonylphenyl]-5-13,4,5-trimethoxyphenyl) tetrahydrofuran (compound 233, scheme 5)

This compound was prepared from 232 in a manner similar to that used for 229. $^1$H NMR (CDCl$_3$) 6 1.00 (t, 3 H); 1.05 (t, 3 H); 1.32 (d, 3 H); 1.72 (m, 2 H); 1.88 (m, 2 H); 1.99 (m, 2 H); 2.48 (m, 2 H); 3.38 (m, 2 H); 3.84 (s, 3 H); 3.88 (s, 6 H); 3.99 (m, 2 H); 4.12 (t, 2 H); 4.23 (m, 1 H); 5.21 (m, 2 H); 6.60 (s, 2 H); 7.28 (d, 1 H); 7.51 (d, 2 H).

Trans-2-[3-(2-methylsufonylpropoxy)-4-propoxy-5-propylsulfonylphenyl]-5-(3,4,5-trimethoxyphenyl) tetrahydrofuran (compound 234,scheme 5)

To a solution of 233 (580 mg, 1.04 mmol) in 3 mL dichloromethane at 0° C. was added methanesulfonyl chloride (142.9 mg, 1.25 mmol) and triethylamine (189.3 mg, 1.87 mmol). The reaction was stirred at room temperature for 2 hours. The solvent was evaporated in vacuo and the residue purified by flash column chromatography (silica, 2:1 hexane/ethyl acetate) (600 mg, 91.6%). $^1$H NMR (CDCl$_3$) δ1.01 (t, 3 H); 1.06 (t, 3 H); 1.58 (d, 3 H); 1.72 (m, 2 H); 1.88 (m, 2 H); 1.99 (m, 2 H); 2.49 (m, 2 H); 3.08 (s, 3 H); 3.38 (m, 2 H); 3.84 (s, 3 H); 3.88 (s, 6 H); 4.16 (m, 4 H); 5.20 (m, 2 H); 6.61 (s, 2 H); 7.28 (d, 1 H); 7.51 (d, 1 H).
Trans-2-[3-(2-hydroxyaminopropoxy)-4-propoxy-5-propylsulfonylphenyl-5-(3,4,5-trimethoxyphenyl) tetrahydrofuran (compound 235, scheme 5)

To a solution of 234 (212 mg, 0.34 mmol) in 5 mL ethanol was added sodium carbonate (80.3 mg, 0.76 mmol) and hydroxyamine hydrochloride (35.1 mg, 0.50 mmol). The reaction mixture was refluxed for 40 hours. The reaction was quenched with water and extracted with ethyl acetate. The organic layer was washed with water and saturated sodium chloride solution, dried over magnesium sulfate, filtered and evaporated in vacuo to an oil which was purified by flash column chromatography (silica, ethyl acetate) (30 mg). $^1$H NMR (CDCl$_3$) δ1.01 (t, 3 H); 1.06 (t, 3 H); 1.25 (d, 3 H); 1.74 (m, 2 H); 1.89 (m, 2 H); 2.00 (m, 2 H); 2.49 (m, 2 H); 3.39 (m, 2 H); 3.48 (m, 1 H); 3.84 (s, 3 H); 3.88 (s, 6 H); 4.11 (m, 2 H); 5.21 (m, 2 H); 6.61 (s, 2 H); 7.31 (d, 1 H); 7.51 (d, 1 H).
Trans-2-[3-(2-(N'-amino-N-hydroxyureidyl)-propoxy)-4-propoxy-5-propylsulfonylphenyl]-5-(3,4,5-trimethoxyphenyl)tetrahydrofuran (compound 28, scheme 5)

To a solution of 235 (30 mg, 0.052 mmol) in 1 mL dichloromethane was added trimethylsilyl isocyanate (6.0 mg, 0.052 mmol). The reaction mixture was stirred at room temperature for 2 hours. Saturated ammonium chloride solution was added to the reaction and the mixture was extracted with ethyl acetate. The organic layer was washed with saturated sodium chloride solution, dried over magnesium sulfate, filtered and evaporated in vacuo to an oil which was purified by preparative TCL (silica, ethyl acetate) (10.7 mg, 33.4%). $^1$H NMR (CDCl$_3$) δ1.01 (m, 6 H); 1.26 (d, 3 H); 1.70 (m, 2 H); 1.84 (m, 2 H); 1.99 (m, 2 H); 2.46 (m, 2 H); 3.36 (t, 2 H); 3.83 (s, 3 H); 3.88 (s, 6 H); 4.00 (m, 1 H); 4.21 (m, 3 H); 4.71 (m, 1 H); 5.20 (m, 2 H); 5.29 (bs, 2 H); 6.60 (s, 2 H); 7.27 (d, 1 H); 7.49 (d, 1 H).
Trans-2-[3-(2-(N'-methyl-N-hydroxyureidyl)-propoxy)-4-propoxy-5-propylsulfonylphenyl]-5-(3,4,5-trimethoxyphenyl)tetrahydrofuran (compound 29, scheme 5)

To a solution of 235 (18 mg, 0.031 mmol) in 0.5 mL dichloromethane was added methyl isocyanate (1.8 mg, 0.031 mmol). The reaction mixture was stirred at room temperature for 0.5 hours. The solvent was evaporated in vacuo and the product was purified by preparative TCL (silica, ethyl acetate) (4.4 mg, 22.4%). $^1$H NMR (CDCl$_3$) δ1.01 (t, t, 6 H); 1.29 (m, 3 H); 1.71 (m. 2 H); 1.85 (m, 2 H); 1.99 (m, 2 H); 2.47 (m, 2 H); 2.80 (d, 3 H); 3.37 (t, 2 H); 3.83 (s, 3 H); 3.88 (s, 6 H); 4.11 (m, 4 H); 4.74 (m, 1 H); 5.21 (m, 2 H); 6.88 (m, 1 H); 6.61 (s, 2 H); 7.28 (d, 1 H); 7.49 (d, 1 H).

EXAMPLE 9

Preparation of trans-2-[3-(3-(N'-hydroxy-N'-substituted ureidyl)ethoxy)4-propoxy-5-methanesulfonylphenyl]-5-(3,4,5-trimethoxyphenyl) tetrahydrofuran (compounds 30–32, scheme 6)
Trans-2-[3-(3-(N-benzyloxycarbonylamino) propoxy)-4-ethoxy-5-methanesulfonylphenyl]-5-(3,4,5-trimethoxyphenyl)tetrahydrofuran (compound 236, scheme 6)

To a solution of 221 (437 mg, 1 mmol) in 20 mL DMF was added potassium carbonate (414 mg, 3 mmol) and 2-bromo-1-(N-benzyloxycarbonyl)ethylamine (322 mg, 1.25 mmol). The reaction was stirred at 40° C. for 16 hours. The reaction was quenched with water and extracted with ethyl acetate. The organic layer was washed with water and saturated sodium chloride solution, dried over magnesium sulfate, filtered and evaporated in vacuo to an oil which was purified by flash column (silica, 2:1 hexane/ethyl acetate) (563 mg, 92%). $^1$H NMR (CDCl$_3$) δ1.03 (t, 3 H); 1.85 (m, 2 H); 2.08 (m, 2 H); 2.50 (m, 2 H); 3.26 (s, 3 H); 3.70 (m, 2 H); 3.84 (s, 3 H); 3.88 (s, 6 H); 4.11 (m, 4 H); 5.10 (s, 2 H); 5.20 (m, 2 H); 6.60 (s, 2 H); 7.25 (d, 1 H); 7.31 (m, 4 H); 7.49 (d, 1 H).
Trans-2-[3-(3-aminoethoxy)-4-propoxy-5-methanesulfonylphenyl]-5-(3,4,5-trimethoxyphenyl) tetrahydrofuran (compound 237, scheme 6)

A solution of 236 (614 mg, 1 mmol) in 50 mL of ethanol was refluxed over 10% palladium-on charcoal (909 mg) and cyclohexene (21 mi) for 2.5 hours. The catalyst was filtered off over Celite, and the filtrate was evaporated in vacuo to give the named product (387 mg, 82%). $^1$H NMR (CDCl$_3$) δ1.05 (t, 3 H); 1.99 (m, 2 H); 2.02 (m, 2 H); 2.47 (m, 2 H); 3.15 (m, 2 H): 3.26 (m, 2 H); 3.84 (s, 3 H); 3.88 (s, 6 H); 4.10 (t, 2 H); 4.15 (t, 2 H); 5.20 (m, 2 H); 6.60 (2, 2 H); 7.26 (d, 1 H); 7.46 (d, 1 H).
Trans-2-[3-(3-(N'-methyl-N'-hydroxyureidyl) propoxy)-4-propoxy-5-propylsulfonylphenyl]-5-(3,4,5-trimethozyphenyl)tetrahydrofuran (compound 30, scheme 6)

237 (51 mg, 0.1 mmol) was dissolved in 5 mL dry dichloromethane. To this solution was added triphosgene (14 mg, 0.048 mmol) and triethylamine (25 μL, 0.18 mmol). The reaction mixture was refluxed for 2 hours and then cooled with an ice bath. To this cold solution was added methylhydroxyamine hydrochloride (20 mg, 0.239 mmol) and triethylamine (54 μL, 0.394 mmol). The reaction mixture was stirred at room temperature overnight. The solvent was evaporated in vacuo and the product was purified by preparative TLC (silica, ethyl acetate) (44 mg, 76%). $^1$H NMR (CDCl$_3$) δ1.0 (t, 3 H); 1.90 (m, 2 H); 2.00 (m, 2 H); 2.49 (m, 2 H); 3.05 (s, 3 H); 3.30 (s, 3 H); 3.85 (m, 11 H); 4.15 (t. 2 H); 4.25 (t, 2 H); 5.20 (m, 2 H); 6.60 (s, 2 H); 0.28 (d, 1 H); 7.48 (d, 1 H).

The following compounds were prepared in a similar manner to that described above by using the corresponding hydroxylamines.

Compound 31, scheme 6: $^1$H NMR (CDCl$_3$) δ1.10 (m, 6 H); 1.90 (m, 2 H); 2.00 (m, 2 H); 2.49 (m, 2 H); 3.30 (s, 3 H); 3.40 (m, 2 H); 3.70 (m, 2 H); 3.85 (m, 11 H); 4.15 (t, 2 H); 4.25 (t, 2 H); 5.20 (m, 2 H); 6.60 (s, 2 H); 7.28 (d, 1 H); 7.48 (d, 1 H).

Compound 32, scheme 6: $^1$H NMR (CDCl$_3$) δ0.09 (t, 3 H); 1.10 (t, 3 H); 1.30 (m, 4 H); 1.90 (m, 2 H); 2.00 (m, 2 H); 2.49 (m, 2 H); 3.30 (s, 3 H); 3.40 (m, 2 H); 3.70 (m, 2 H); 3.85 (m, 11 H); 4.15 (t, 2 H); 4.25 (t, 2 H); 5.20 (m, 2 H); 6.60 (s, 2 H); 7.28 (d, I H); 7.48 (d, 1 H).

EXAMPLE 10

Preparation of trans-2-[3-(4-(N'-hydroxy-N'-substituted ureidyl)butyloxy-4-propoxy-5-methylsulfonylphenyl]-5-(3,4,5-trimethoxyphenyl) tetrahydrofuran (compounds 33–37, scheme 7)
Trans-2-[3-(4-phthalimidylbutyloxy)-4-propoxy-5-methylsulfonyl-phenyl]-5-(3,4,5-trimethoxyphenyl) tetrahydrofuran (compound 238, scheme 7)

To a solution of 221 (437 mg, 1 mmol) in 15 mL DMF was added potassium carbonate (180 mg, 1.30 mmol) and the N-(4-bromobutyl)phthalimide (423 mg, 1.5 mmol), The reaction was stirred at 100° C. for 16 hours. The reaction was quenched with water and extracted with ethyl acetate.

The organic layer was washed with water and saturated sodium chloride solution, dried over magnesium sulfate, filtered and evaporated in vacuo to an oil which was purified by flash column (silica, 1:1 hexane/ethyl acetate) (600 mg, 94%). $^1$H NMR (CDCl$_3$) δ1.02 (t, 3 H); 1.70–2.10 (m, 8 H); 2.5 (m, 2 H); 3.24 (s, 3 H); 3.84 (s, 3 H); 3.88 (s, 6 H); 4.12 (m. 4 H); 5.20 (m, 2 H); 6.61 (s, 2 H); 7.22 (d, 1 H); 7.51 (d, 1 H); 7.74 (m, 2 H); 7.86 (m, 2 H).

Trans-2-[3-(4-aminobutyloxy)-4-propoxy-5-methylsulfonylphenyl]-5-(3,4,5-trimethoxyphenyl) tetrahydrofuran (compound 239, scheme 7)

To a solution of 238 (319 mg, 0.5 mmol) in 30 mL ethanol was added hydrazine monohydrate (120 µL, 1.74 mmol). The reaction mixture was refluxed overnight and then quenched with water, extracted with methylene chloride. The organic layer was washed with water and saturated sodium chloride solution, dried over magnesium sulfate, filtered and evaporated in vacuo to provide the product (160 mg, 60%). $^1$H NMR (CDCl$_3$) δ1.05 (t, 3 H); 1.70–2.10 (m, 8 H); 2.50 (m, 2 H); 3.24 (s, 3 H); 3.39 (m, 2 H); 3.84 (s, 3 H); 3.88 (s, 6 H); 4.14 (m, 4 H); 5.21 (m, 2 H); 6.61 (s, 2 H); 7.28 (d, 1 H); 7.51 (d, 1 H).

Trans-2-[3-(4-(N'-methyl-N'-hydroxyureidyl) butyloxy)-4-propoxy-5-methylsulfonylphenyl]-5-(3,4,5-trimethoxyphenyl)tetrahydrofuran (compound 33, scheme 7)

239 (53.7 mg, 0.1 mmol) was dissolved in 20 mL of dry dichloromethane. To this solution was added triphosgene (13 mg, 0.048 mmol) and triethylamine (27 µL, 0.197 mmol). The reaction mixture was refluxed for 2 hours and then cooled with an ice bath. To this cold solution was added methylhydroxyamine hydrochloride (20 mg, 0.239 mmol) and triethylamine (54 µL, 0.394 mmol). The reaction mixture was stirred at room temperature overnight, and then quenched with water and extracted with ethyl acetate. The organic layer was washed with water and saturated sodium chloride solution, dried over magnesium sulfate, filtered and evaporated in vacuo. The product was purified by preparative TLC (silica, ethyl acetate) (42 mg, 49%). $^1$H NMR (CDCl$_3$) δ1.05 (t, 3 H); 1.70 (m, 2 H); 1.87 (m, 4 H): 1.99 (m, 2 H); 2.47 (m, 2 H); 3.06 (s, 3 H); 3.26 (s, 3 H); 3.30 (m. 2 H); 3.84 (s, 3 H); 3.88 (s, 6 H); 4.13 (m, 4 H); 5.21 (m, 2 H); 6.61 (s, 2 H); 7.23 (d, 1 H); 7.52 (d, 1 H).

The following compounds were prepared in a manner similar to that described above by using the corresponding hydroxylamines.

Compound 34, scheme 7: $^1$H NMR (CDCl$_3$) δ1.05 (m, 6 H); 1.70 (m, 2 H); 1.87 (m, 4 H); 1.99 (m, 2 H); 2.47 (m, 2 H); 3.26 (s, 3 H); 3.36 (m, 2 H); 3.84 (s, 3 H); 3.88 (s, 6 H); 4.13 (m, 4 H); 4.40 (m, 1 H); 5.21 (m, 2 H); 6.61 (s, 2 H); 7.23 (d, 1 H); 7.52 (d, 1 H).

Compound 35, scheme 7: $^1$H NMR (CDCl$_3$) δ1.05 (t, 3 H); 1.10 (md, 6 H); 1.70 (m, 2 H); 1.87 (m, 2 H); 1.99 (m, 2 H); 2.47 (m, 2 H); 3.26 (s, 3 H); 3.36 (m, 2 H); 3.84 (s, 3 H); 3.87 (m, 2 H); 3.88 (s, 6 H); 4.13 (t, 2 H); 4.62 (d, 2 H); 5.21 (m, 2 H); 5.86 (m, 1 H); 5.99 (m, 1 H); 6.61 (s, 2 H); 6.99 (s, 1 H); 7.23 (d, 1 H); 7.52 (d, 1 H).

Compound 36, scheme 7: $^1$H NMR (CDCl$_3$) δ0.90 (t, 3 H); 1.05 (t, 3 H); 1.30 (m, 2 H); 1.55 (m, 2 H); 1.70 (m, 4 H); 1.87 (m, 2 H); 1.99 (m, 2 H); 2.47 (m, 2 H); 3.26 (s, 3 H); 3.30 (s, 3 H); 3.45 (m, 2 H); 3.84 (s, 3 H); 3.88 (s, 6 H); 4.13 (m, 4 H); 5.21 (m, 2 H), 6.61 (s, 2 H); 7.23 (d, 1 H); 7.52 (d, 1 H).

Compound 37 scheme 4: $^1$H NMR (CDCl$_3$) δ0.90 (t, 3 H); 1.05 (t, 3 H); 1.30 (m, 4 H); 1.55 (m, 2 H); 1.70 (m, 4 H); 1.87 (m, 2 H); 1.99 (m, 2 H); 2.47 (m, 2 H); 3.26 (s, 3 H); 3.30 (s, 3 H); 3.45 (m, 2 H); 3.84 (s, 3 H); 3.88 (s, 6 H); 4.13 (m, 4 H); 5.21 (m, 2 H); 6.61 (s, 2 H); 7.23 (d, 1 H); 7.52 (d, 1 H).

EXAMPLE 11

1-Hydroxy-4-phthalimido-2-butyne (compound 240, scheme 8):

1,4-Dihydroxy-2-butyne (430 mg, 5.0 mmol), triphenylphosphine (1.44 g, 5.5 mmol) and phthalimide (1.47 g, 10.0 mmol) were dissolved in 50 mL of dry THF. To this solution, with stirring under dry argon, was added diisopropyl azodicarboxylate (1.09 mL, 5.25 mmol) dropwise. After stirring at room temperature for 6 hours, the reaction mixture was evaporated in vacuo to remove the THF. The residue was dissolved in methylene chloride (25 mL) and ethyl acetate (25 mL), the insoluble phthalimide was filtered off and the filtrate was concentrated in vacuo. The residue was subjected to flash column chromatography (eluent, ethyl acetate-hexane, 1:1) to give 1-hydroxy-4-phthalimido-2-butyne (240) as a white solid (570 mg, 53%). $^1$H NMR (CDCl$_3$) δ7.88 (2H, dd, J=5.7, 3.1 Hz), 7.74 (2H, dd, J 5.7, 3.1 Hz), 4.49 (2H, t, J=2.0 Hz), 4.24 (2H, dt, J=6.2, 2.0 Hz), 1.92 (1 H, t, J=6.2 Hz).

Trans-2-(3-methylsulfonyl-5-(4-phthalimido-but-2-ynyloxy)-4-propylozyphenyl)-5-(3,4,5-trimethoxyphenyl) tetrahydrofuran (compound 244, scheme 8):

To a solution of 1-hydroxy-4-phthalimido-2-butyne (240, 71 mg, 0.33 mmol) and triethylamine (46 mL, 0.33 mmol) in dry methylene chloride (3.0 mL), with stirring at 0° C. under argon, was added methanesulfonyl chloride (25 mL, 0.33 mmol) dropwise. After stirring at the same temperature for 30 min. and then at room temperature for 2 hours, the reaction mixture was diluted with 10 mL of methylene chloride and washed with water (2×15 mL). The organic phase was dried over magnesium sulfate and concentrated in vacuo to yield 241.

Trans-2-(3-hydroxy-5-methylsulfonyl-4-propyloxyphenyl)-5-(3,4,5-trimethoxyphenyl) tetrahydrofuran (242), 130 mg, 0.28 mmol) was dissolved in dry DMF (1.5 mL) and K$_2$CO$_3$ (58 Mg, 0.42 mmol) was added to it. Stirred, at room temperature under argon, for 30 min and a solution of 241, made above, in 1.0 mL of dry DMF was added. The resulting reaction mixture was stirred at 70° C. overnight. The reaction mixture was diluted with methylene chloride (25 mL) and washed with water (25 mL). The water layer was extracted once with 25 mL of methylene chloride. The combined methylene chloride extracts were dried over magnesium sulfate and concentrated in vacuo to obtain trans-2-13-methylsulfonyl-5-(4-phthalimido-but-2-ynyloxy)-4-propyloxyphenyl]-5-(3,4,5-trimethoxyphenyl) tetrahydrofuran, 244, which was used without further purification. $^1$H-NMR (CDCl$_3$) (5 7.85 (2H, dd, J=5.3, 3.2 Hz), 7.73 (2H, dd, J=5.3, 3.2 Hz), 7.55 (1 H, d, J=2.0 Hz), 7.32 (1 H, d, J=2.0 Hz), 6.62 (2H, s), 5.16–5.21 (2H, m), 4.77 (2H, s), 4.49 (2H, s), 4.11 (2H, t, J=6.8 Hz), 3.89 (6H, s), 3.84 (3H, s), 3.24 (3H, s), 2.41–2.46 (2H, m), 1.80–2.01 4H, m), 1.04 (3H, t, J=6.8 Hz).

Trans-2-[3-(4-amino-but-2-ynyloxy)-5-methylsulfonyl-4-propyloxy-phenyl]-5-(3,4,5-trimethoxyphenyl) tetrahydrofuran (246):

To a solution of trans-2-[3-methylsulfonyl-5-(4-phthalimido-but-2-ynyloxy)-4-propyloxyphenyl]-5-(3,4,5-trimethoxyphenyl)tetrahydrofuran (244, whole amount obtained from the previous step) in ethanol (5.0 mL) was added hydrazine hydrate (1 36 mL, 2.8 mmol)The resulting solution was refluxed overnight. The ethanol was removed in vacuo and the residue was diluted with methylene chloride (25 mL) and water (25 mL). The layers were separated and the water layer was extracted with methylene chloride (25 mL). The combined organic extracts were dried and concentrated in vacuo. The residue was purified using PLC (eluent, 5% methanol in methylene chloride) to obtain 75 mg (50% overall from 242) of trans-2-[3-(4-amino-but-2-ynyloxy)-5-methylsulfonyl-4-propyloxyphenyl]-5-(3,4,5-trimethoxy-phenyl)tetrahydrofuran (244). $^1$H-NMR (CDCl$_3$) δ7.55 (1H, d, J=2.0 Hz), 7.37 (1H, d, J=2.0 Hz), 6.59 (2H, s), 5.16–5.28 (2H, m), 4.79 (2H, s), 4.12 (2H, t, J=6.6 Hz), 3.87 (6H, s), 3.81 (3H, s), 3.44 (2H, s), 3.23 (3H, s), 2.43–2.50 (2H, m), 1.83–2.03 (4H, m), 1.57 (2H, brs), 1.04 (3H, t, J=6.6 Hz).

Trans-2-[3-[4-(N'-methyl-N'-hydroxyureidyl)-but-2-ynyloxy]-5-methylsulfonyl-4-propyloxyphenyl]-5-(3,4,5-trimethoxyphenyl)tetrahydrofuran (compound 38, scheme 8):

A solution of trans-2-13-(4-amino-but-2-ynyloxy)-5-methylsulfonyl-4-propyloxyphenyl]-5-(3,4,5-trimethoxyphenyl) tetrahydrofuran (75 mg, 0.14 mmol) (246), triethylamine (41 mL, 0.3 mmol) and triphosgene (14.2 mg, 0.05 mmol) in dry methylene chloride (3.0 mL) was refluxed under argon for 3 hours. The reaction mixture was cooled to room temperature and a solution of N-hydroxymethylamine hydrochloride (23 mg, 0.28 mmol) and triethylamine (41 mL, 0.3 mmol) in THF-water (2 mL THF, 0.5 mL water) was added. This mixture was stirred at room temperature for 3 hours. The reaction mixture was diluted with methylene chloride (25 mL), washed with water, dried and concentrated in vacuo. The residue was subjected to PLC (eluent, 5% methanol in methylene chloride) to yield 60 mg of the target hydroxy urea, 1, (71%). IR (film) 3385, 2940, 2251, 1649, 1593, 1466, 1306, 1235, 1128, 1036 cm$^{-1}$; $^1$H NMR (CDCl$_3$) δ7.59 (1 H, d, J=1.9 Hz), 7.27–7.36 (2H, m), 6.61 (2H, s), 5.89 (1 H, t, J=5.6 Hz), 5.20–5.28 (2H, m), 4.82 (2H, s), 4.14 (2H, t, J=6.9 Hz), 3.82–3.98 (11H, m), 3.28 (3H, s), 2.93 (3H, s), 2.46–2.53 (2H, m), 1.80–2.07 ( 4H, m), 1.05 (3H, t, J=6.9 Hz); $^{13}$C NMR (CDCl$_3$) δ160.54, 153.40, 151.10, 146.88, 139.13, 138.01, 134.79, 118.85, 118.57, 102.79, 102.59, 86.00, 82.44, 81.14, 77.50, 60.90, 57.35, 56.25, 43.56, 38.60, 35.77, 35.57, 35.40, 30.03, 23.28, 10.43.

Trans-2-[3-propylsulfonyl-5-(4-phthalimido-but-2-ynyloxy)-4-propyloxyphenyl]-5-(3,4,5-trimethoxyphenyl) tetrahydrofuran (245):

Starting with 243 (36 mg, 0.073 mmol), and using the same procedure as for compound 244, compound 245 was obtained. The yield was not determined, and the whole amount obtained was used without any purification. $^1$H NMR (CDCl$_3$) δ7.83 (2H, dd, J=5.0, 3.3 Hz), 7.71 (2H, dd, J=5.0, 3.3 Hz), 7.50 (1H, d, J=1.9 Hz), 7.30 (1 H, d, J=1.9 Hz), 6.60 (2H, s), 5.10–5.21 (2H, m), 4.76 (2H, s), 4.47 (2H, s), 4.08 (2H, t, J=6.7 Hz), 3.86 (6H, s), 3.83 (3H, s), 3.32–3.37 (2H, m), 2.39–2.43 (2H, m), 1.60–2.05 (6H, m), 0.94–1.23 (6H, m).

Trans-2-[3-(4-amino-but-2-ynyloxy)-5-propylsulfonyl-4-propyloxy-phenyl]-5-(3,4,5-trimethoxyphenyl) tetrahydrofuran (247):

Using the same procedure as for compound 246, starting with 245 (the whole amount obtained in the previous step) 15 mg of compound 247 was obtained (37%, overall all from 243). $^1$H NMR (CDCl$_3$) δ7.54 (1H, d, J=1.6 Hz), 7.38 (1 H, d, J=1.6 Hz), 6.61 (2H, s), 5.15–5.30 (2H, m), 4.81 (2H, s), 4.13 (2H, t, J 6.9 Hz), 3.88 (6H, s), 3.84 (3H, s), 3.47 (2H, brs), 3.36–3.41 (2H, m), 2.40–2.55 (2H, m), 1.65–2.05 (8H, m), 0.97–1.08. (6H, M).

Trans-2-[3-[4-(N'-butyl-N'-hydroxyureidyl)-but-2-ynyloxy]-5-propylsulfonyl-4-propyloxyphenyl]-5-(3,4,5-trimethoxyphenyl)tetrahydrofuran (compound 39, scheme 8):

The procedure used for this compound was similar to the one used for the methylsulfonyl-N-methyl analogue. Thus starting with 247 (15 mg, 0.027 mmol), 5 mg of 39 was obtained (27%). $^1$H NMR (CDCl$_3$) δ7.57 (1H, d, J=2.0 Hz), 7.37 (1H, d, J=2.0 Hz), 7.27–7.36 (2H, m), 6.61 (2H, s), 5.89 (1 H, t, J=5.6 Hz), 5.20–5.28 (2H, m), 4.83 (2H, s), 4.14 (2H, t, J=6.7 Hz), 3.95–4.05 (2H, m), 3.90 (6H, s), 3.85 (3H, s), 3.38–3.40 (2H, m), 3.38 (2H, t, J 7.2 Hz), 2.43–2.55 (2H, m), 1.68–2.10 (6H, m), 1.35–1.50 (2H, m), 1.15–1.20 (2H, m), 0.95–1.12 (6H, m), 0.88 (3H, t, J=7.1 Hz).

EXAMPLE 12

Trans-2-[3-methylsulfonyl-5-(4-hydroxy-but-2-ynyloxy)-4-propyloxy-phenyl]-5-(3,4,5-trimethoxyphenyl)tetrahydrofuran (compound 248, scheme 9):

To a solution of trans-2-[3-hydroxy-5-methylsulfonyl-4-propyloxyphenyl]-5-(3,4,5-trimethoxyphenyl) tetrahydrofuran (242, 130 mg, 0.28 mmol), triphenylphosphine (87 mg, 0.33 mmol) and 1,4dihydroxy-but-2-yne (36 mg, 0.42 mmol) in 2 mL of dry THF, under argon, with stirring, was added diisopropyl azodicarboxylate (62 mL, 0.315 mmol) dropwise. The resulting solution was stirred at 80° C. for 1.5 hours. THF was removed in vacuo and the residue was subjected to PLC (eluent, ethyl acetate:hexane/ 3:1) to obtain 120 mg (80%) of 248. $^1$H NMR (CDCl$_3$) δ7.58 (1H, d, J=2.0 Hz), 7.43 (1H, d, J=2.0 Hz), 6.62 (2H, s), 5.18–5.21 (2H, m), 4.85 (2H, d, J=1.7 Hz), 4.28–4.30 (2H, m), 4.16 (2H, t, J=6.8 Hz), 3.89 (6H, s), 3.84 (3H, s), 3.26 (3H, s), 2.40–2.55 (2H, m), 1.72–2.05 (5H, m), 1.07 (3H, t, J=7.4, Hz).

Trans-2-[3-[4-(N-phenoxycarbonyloxy-N-phenoxycarbonylamino)-but-2-ynyloxy]-5-methylsulfonyl-4-propyloxyphenyl]-5-(3,4,5-trimethoxyphenyl) tetrahydrofuran (compound 249, scheme 9):

To a solution of 248 (120 mg, 0.224 mmol), triphenylphosphine (65 mg, 0.246 mmol) and N,O-bis-(phenoxycarbonyl)hydroxylamine (61 mg, 0.236 mmol) in 5 mL of dry THF, under argon with stirring, was added diisopropyl azodicarboxylate (47 mL, 0.236 mmol) dropwise. The resulting solution was stirred at room temperature for 2 hours. THF was removed in vacuo and the residue was subjected to PLC (eluent, ethyl acetate:hexane/1:1) to obtain 125 mg (72%) of 302. $^1$H NMR (CDCl$_3$) δ7.60 (1H, d, J=1.9 Hz), 7.09–7.43 (11H, m), 6.60 (2H, s), 5.18–5.29 (2H, m), 4.89 (2H, s), 4.66 (2H, s), 4.16 (2H, t, J=6.9 Hz), 3.84 (9H, s), 3.25 (3H, s), 2.40–2.52 (2H, m), 1.85–2.00 (4H, m), 1.06 (3H, t, J=7.4 Hz).

Trans-2-[3-[4-(N-hydroxyureidyl)-but-2-ynyloxy]-5-methylsulfonyl-4-propyloxyphenyl]-5-(3,4,5-trimethozyphenyl)tetrahydrofuran (compound 40, scheme 9):

To a solution of 249 (64 mg, 0.083 mmol) in 10 mL of dry THF, under argon, was added sodium amide (33 mg, 0.83 mmol). The reaction mixture was stirred at room temperature for 6 hours. THF was removed in vacuo and the residue was partitioned between methylene chloride (25 mL) and water (25 mL). The layers were separated and water layer was extracted once more with methylene chloride (25 mL). The combined organic extracts were dried over magnesium sulfate and concentrated in vacuo. The residue was subjected to PLC (eluent, 5% MeOH in methylene chloride) to obtained 40, (4 mg, 8.1%) along with 242 (10 mg). $^1$H NMR (CDCl$_3$) δ7.61 (1 H, d, J 1.6 Hz), 7.38 (1H, d, J 1.6 Hz), 6.62 (2H, s), 5.35 (1H, t, J=7.1 Hz), 5.24 (1 H, t, J=7.1 Hz), 5.00 (2H, d, J=2.2 Hz), 4.14 (2H, t, J=6.6 Hz), 3.81–3.87 (11H, m), 3.26 (3H, s), 2.40–2.60 (2H, m), 1.80–2.15 (4H, m), 1.05 (3H, t, J=7.4 Hz).

EXAMPLE 13

Preparation of trans-2-[3-(2-(N'-hydroxy-N'-substituted ureidyl)ethoxy)-4-propoxy-5-methylsulfonylphenyl)-5-[5-

(2,3-dimethoxy) pyridyl]tetrahydrofuran (compounds 41–44, scheme 10) and trans-2-[3-(2-(N'hydroxy-N'-butylureidyl)ethoxy)-4-propoxy-5-propylsulfonylphen yl]-5-[5-(2,3-dimethoxy)pyridyl]tetrahydrofuran (compound 45, scheme 10)

Trans-2-(3-benzyloxy-4-propoxy-5-propylsulfonylphenyl)-5-[5-(2,3-dimethoxy) pyridyl]tetrahydrofuran (compound 251, scheme 10)

To a stirred solution of 250 (prepared according to the procedure in U.S. Pat. No. 5,011,847) (60 mg, 0.11 mmol) in 0.5 mL dry THF at −78° C. was added dropwise lithium bis(trimethylsilyl) amide (0.31 mL, 0.31 mmol). After 20 minutes at this temperature, iodoethane (117 mg, 0.75 mmol) was added, and after an additional 40 minutes, a solution of saturated ammonium chloride was added. The reaction mixture was warmed to room temperature, and the product was isolated by flash column chromatography (silica, 2:1 hexane/ethyl acetate) (25 mg, 39.6%). $^1$H NMR (CDCl$_3$) δ1.00 (m, 6 H); 1.74 (m, 2 H); 1.85 (m, 2 H); 1.99 (m, 2 H); 2.46 (m, 2 H); 3.40 (m, 2 H); 3.91 (s, 3 H); 4.02 (s, 3 H); 4.16 (t, 2 H); 5.16 (s, 2 H); 5.20 (m, 2 H); 7.12 (d, 1 H); 7.32 (d, 1 H); 7.42 (m, 4 H); 7.50 (d, 1 H) 7.72 (d, 1 H).

Trans-2-(3-hydroxy-4-propoxy-5-methylsulfonylphenyl)-5-[5-(2,3-dimethoxy) pyridyl]tetrahydrofuran (compound 252, scheme 10)

A solution of 250 (300 mg, 0.57 mmol) in 2 mL ethyl acetate was hydrogenated over 10% palladium-on-charcoal (30 mg) at balloon pressure for 1.5 hour. The catalyst was filtered off over Celite, and the filtrate was evaporated in vacuo to give the product (261 mg, 105.2%). $^1$H NMR (CDCl$_3$) δ1.04 (t, 3 H); 1.88 (m, 2 H); 1.96 (m, 2 H); 2.45 (m, 2 H); 3.21 (s, 3 H); 3.88 (s, 3 H); 4.00 (s, 3 H); 4.10 (t, 2 H); 5.15 (m, 2 H); 7.10 (d, 1 H); 7.25 (d, 1 H); 7.44 (d, 1 H); 7.67 (d, 1 H).

Trans-2-(3-hydroxy-4-propoxy-5-propylsulfonylphenyl)-5-[5-(2,3-dimethoxy) pyridyl]tetrahydrofuran (compound 253, scheme 10)

This compound was prepared from 251 in a manner similar to that described for 252. $^1$H NMR (CDCl$_3$) δ1.01 (t, 3 H); 1.09 (t, 3 H); 1.72 (m, 2 H); 1.90 (m, 2 H); 2.00 (m, 2 H); 2.49 (m, 2 H); 3.34 (m, 2 H); 3.91 (s, 3 H); 4.01 (s, 3 H); 4.10 (t, 2 H); 5.20 (m, 2 H); 6.07 (s, 1 H); 7.11 (d, 1 H); 7.30 (d, 1 H); 7.46 (d, 1 H); 7.70 (d, 1 H).

Trans-2-[3-(2-N-benzyloxycarbonylaminoethoxy)-4-propoxy-5-methyl-sulfonylphenyl)]-5-[5-(2,3-dimethoxy)pyridyl]tetrahydrofuran (compound 254, scheme 10)

To a solution of 252 (223 mg, 0.51 mmol) in 3 mL DMF was added potassium carbonate (211.6 mg, 1.53 mmol) and 2-bromo-1-(N-benzyloxy-carbonyl)ethylamine (158 mg, 0.61 mmol). The reaction mixture was stirred at 40° C. for 16 hours. The reaction was quenched with water and extracted with ethyl acetate. The organic layer was washed with water and saturated sodium chloride solution, dried over magnesium sulfate, filtered and evaporated in vacuo to provide the product (200 mg, 63.9%). $^1$H NMR (CDl$_3$) δ1.02 (t, 3 H); 1.85 (m, 2 H); 2.99 (m, 2 H); 2.49 (m, 2 H); 3.22 (s, 3 H); 3.65 (m, 2 H); 3.90 (s, 3 H); 4.00 (s, 3 H); 4.12 (m, 4 H); 5.10 (s, 2 H); 5.20 (m, 2 H); 7.10 (d, 1 H); 7.26 (d, 1 H); 7.34 (m, 4 H); 7.51 (d, 1 H); 7.70 (d, 1 H).

Trans-2-[3-(2-N-benzyloxycarbonylaminoethoxy)-4-propoxy-5-propyl-sulfonylphenyl)]-5-[5-(2,3-dimethoxy)pyridyl]tetrahydrofuran (compound 255, scheme 10)

This compound was prepared from 253 in a manner similar to that described for 254. $^1$H NMR (CDCl$_3$) δ1.00 (t, 3 H); 1.02 (t, 3 H); 1.70 (m, 2 H); 1.84 (m, 2 H); 2.00 (m, 2 H); 2.35 (m, 2 H); 2.48 (m, 2 H); 2.65 (m, 2 H); 3.90 (s, 3 H); 4.00 (s, 3 H); 4.08 (t, 2 H); 4.15 (t, 2 H); 5.10 (s, 2 H); 5.20 (m, 2 H); 7.10 (d, 1 H); 7.26 (d, 1 H); 7.32 (m, 4 H).

Trans-2-[3-(2-aminoethoxy)-4-propoxy-5-methylsulfonylphenyl]-5-[5(2,3-dimethoxy) pyridyl] tetrahydrofuran (compound 256, scheme 10)

A solution of 254 (84 mg, 0.14 mmol) in 2 mL ethanol was added 10% palladium-on charcoal (12 mg) and cyclohexene (3 mL). The reaction mixture was refluxed for 1.5 hours. The catalyst was filtered off over Celite, and the filtrate was evaporated in vacuo to give the product (54 mg, 82.2%). $^1$H NMR (CDCl$_3$,) δ1.04 (t, 3 H); 1.87 (m, 2 H); 2.00 (m, 2 H); 2.49 (m, 2 H); 3.22 (s, 3 H); 3.90 (s, 3 H); 4.00 (s, 3 H); 4.12 (m, 4 H); 5.20 (m, 2 H); 7.10 (d, 1 H); 7.28 (d, 1 H); 7.50 (d, 1 H); 7.70 (d, 1 H).

Trans-2-[3-(2-aminoethoxy)-4-propoxy-5-propylsulfonylphenyl]-5-[5(2,3-dimethoxy) pyridyl] tetrahydrofuran (compound 257, scheme 10)

This compound was prepared from 255 in a manner similar to that described for 256. $^1$H NMR (CDCl$_3$) δ1.00 (t, 3 H); 1.06 (t, 3 H); 1.72 (m, 2 H); 1.86 (m, 2 H); 2.00 (m, 2 H); 2.49 (m, 2 H); 2.72 (m, 2 H); 3.11 (m, 2 H); 3.38 (m, 2 H); 3.90 (8, 3 H); 4.00 (s, 3 H); 4.10 (t, 3 H); 4.20 (t, 3 H); 5.20 (m, 2 H); 7.10 (d, 1 H); 7.26 (d, 1 H); 7.48 (d, 1 H); 7.50 (d, 1 H).

Trans-2-[3-(2-(N'-hydroxy-N-methylureidyl)ethoxy)-4-propoxy-5-methylsulfonylphenyl]-5-[5-(2,3-dimethoxy) pyridyl]tetrahydrofuran (compound 41, scheme 10)

256 (30 mg, 0.063 mmol) was dissolved in 3 mL dry dichloromethane. To this solution was added triphosgene (6.1 mg, 0.021 mmol) and triethylamine (6.3 mg, 0.063 mmol). The reaction mixture was refluxed for 2 hours and then cooled with an ice bath. To this cold solution was added methylhydroxyamine hydrochloride (15.7 mg, 0.187 mmol) and triethylamine (26.3 mg, 0.295 mmol). The reaction mixture was stirred at room temperature overnight. The solvent was evaporated in vacuo and the product was purified by preparative TLC (silica, ethyl acetate) (12 mg, 34.9%). $^1$H NMR (CDCl$_3$) 51.06 (t, 3 H); 1.89 (m, 2 H); 2.05 (m, 2 H); 2.50 (m, 2 H); 3.08 (s, 3 H); 3.26 (s, 3 H); 3.71 (m, 2 H); 3.92 (s, 3 H); 4.03 (s, 3 H); 4.14 (t, 2 H); 4.22 (t, 2 H); 5.21 (m, 2 H); 6.30 (t, 1 H); 6.70 (s, 1 H); 7.10 (d, 1 H); 7.32 (d, 1 H), 7.52 (d, 1 H); 7.72 (d, 1 H).

Trans-2-[3-(2-(N'-hydroxy-N'-butylureidyl)ethoxy)-4-propoxy-5-propyl-sulfonylphenyl]-5-[5-(2,3-dimethoxy)pyridyl]tetrahydrofuran (compound 45, scheme 10)

257 (50 mg, 0.098 mmol was dissolved in 3 mL dry dichloromethane. To this solution was added triphosgene (9.6 mg, 0.032 mmol) and triethylamine (10.0 mg, 0.098 mmol). The reaction mixture was refluxed for 2 hours and then cooled with an ice bath. To this cold solution was added butylhydroxyamine (26.3 mg, 0.295 mmol). The reaction mixture was stirred at room temperature overnight. The solvent was evaporated in vacuo and the product was purified by preparative TLC (silica, ethyl acetate) (18 mg, 29.4%). $^1$H NMR (CDCl$_3$) δ1.05 (t, t, t, 9 H); 1.30 (m, 2 H); 1.51 (m, 2 H); 1.72 (m, 2 H); 1.87 (m, 2 H); 2.02 (m, 2 H); 2.49 (m, 2 H); 3.40 (m 2 H); 3.45 (m, 2 H); 3.70 (t, 2 H); 3.91 (s, 3 H); 4.02 (s, 3 H); 4.12 (t, 2 H); 4.20 (t, 2 H); 5.20 (m, 2 H); 6.28 (t, 1 H); 7.10 (d, 1 H); 7.30 (d, 1 H); 7.50 (d, 1 H); 7.70 (d, 1 H).

Trans-2-[3-(2-(N'-hydroxy-N'-ethylureidyl)ethoxy)-4-propoxy-5-methyl-sulfonylphenyl]-5-[5-(2,3-dimethoxy)pyridyl]tetrahydrofuran (compound 43, scheme 10)

256 (48 mg, 0.10 mmol) was dissolved in 3 mL dry dichloromethane. To this solution was added triphosgene (14 mg, 0.05 mmol) and triethylamine (26 μL, 0.19 mmol). The reaction mixture was refluxed for 2 hours and then cooled with an ice bath. To this cold solution was added ethylhydroxylamine hydrochloride (20 mg, 0.20 mmol) and triethylamine (27 µL, 0.20 mmol). The reaction mixture was stirred at room temperature overnight. The solvent was evaporated in vacuo and the product was purified by preparative TLC (silica, ethyl acetate). $^1$H NMR (CDCl$_3$,) δ7.75 (s, 1 H), 7.55 (s, 1 H), 7.30 s, 1 H), 7.10 (s, 1 H), 5.20 (m, 2 H), 4.20 (t, 2 H), 4.15 (t, 2 H), 4.00 (s, 3 H), 3.90 (s, 3 H), 3.70 (t, 2 H), 3.50 (m, 2 H), 3.25 (s, 3 H), 2.50 (m, 2 H), 2.00 (m, 2 H), 1.90 (m, 2 H), 1.10 (m, 6 H).

The following compounds were prepared in a manner similar to that described above by using the corresponding hydroxylamines.

Compound 44, scheme 10: $^1$H NMR (CDCl$_3$) δ7.75 (s, 1 H), 7.55 (s, 1 H), 7.30 (s, 1 H), 7.10 (s, 1 H), 5.20 (m, 2 H), 4.20 (t, H), 4.15 (t, 2 H), 4.00 (s, 3 H), 3.90 (s, 3 H), 3.70 (t, 2 H), 3.50 (m, 2 H), 3.25 (s, 3 H), 2.50 (m, 2 H), 2.00 (m, 2 H), 1.90 (m, H), 1.50 (m, 2 H), 1.30 (m, 4 H), 1.10 (m, 3 H), 0.90 (t, 3 H).

Compound 42, scheme 10: $^1$H NMR (CDCl$_3$) δ7.75 (s, 1 H), 7.55 (s, 1 H), 7.30 (s, 1 H), 7.10 (s, 1 H), 5.20 (m, 2 H), 4.20 (t, 2 H), 4.15 (t, 2 H), 4.00 (s, 3 H), 3.90 (s, 3 H), 3.70 (t, 2 H), 3.50 (m, 2 H), 3.25 (s, 3 H), 2.50 (m, 2 H), 2.00 (m, 2 H), 1.90 (m, 2 H), 1.50 (m, 2 H), 1.30 (m, 4 H), 1.10 (m, 3 H), 0.90 (t, 3 H).

The following compounds are also preferred embodiments:

Trans-2-[2-(N'-sec-butyl-N'-hydroxyureidylmethylfuran-5-methylenoxy)-4-propoxy-5-methylsulfonylphenyl]-5-(3,4,5-trimethoxyphenyl)tetrahydrofuran, Trans-2-[2-(N'-methyl-N'-hydroxyureidylmethylfuran-5-methylenoxy)-4-propoxy-5-methylsulfonylphenyl]-5-(3,4,5-trimethoxyphenyl) tetrahydrofuran, Trans-2-[2-(N'-n-butyl-N'-hydroxyureidylmethylfuran-5-methylenoxy)-4-propoxy-5-methylsulfonylphenyl]-5-(3,4,5-trimethoxyphenyl)tetrahydrofuran, Trans-2-[2-(N'-sec-butyl-N'-hydroxyureidylmethylfuran-5-methylenoxy)-4-propoxy-5-methylsulfonylphenyl]-5-(3,4,5-trimethoxyphenyl)tetrahydrofuran, Trans-2-[2-(N'-hydroxyureidylmethylfuran-5-methylenoxy)-4-propoxy-5-methylsulfonylphenyl]-5-(3,4,5-trimethoxyphenyl)tetrahydrofuran, Trans-2-[2-(N'-(3-methylbutyl)-N'-hydroxyureidylmethylfuran-5-methylenoxy)-4-propoxy-5-methylsulfonylphenyl]-5-(3,4,5-trimethoxyphenyl) tetrahydrofuran, Trans-2-[2-(N'-isopropyl-N'-hydroxyureidylmethylfuran-5-methylenoxy)-4-propoxy-5-methylsulfonylphenyl]-5-(3,4,5-trimethoxyphenyl)tetrahydrofuran, Trans-2-[2-(N'-cyclopropylmethyl-N'-hydroxyureidylmethylfuran-5-methylenoxy)-4-propoxy-5-methylsulfonylphenyl]-5-(3,4,5-trimethoxyphenyl) tetrahydrofuran, Trans-2-[2-(N'-cyclobutyl-N'-hydroxyureidylmethylfuran-5-methylenoxy)-4-propoxy-5-methylsulfonylphenyl]-5-(3,4,5-trimethoxyphenyl)tetrahydrofuran, Trans-2-[2-(N'-hydroxyureidylmethylfuran-5-methylenoxy)-4-propoxy-5-methylsulfonylphenyl]-5-(3,4,5-trimethoxyphenyl)tetrahydrofuran, Trans-2-[2-(N'-(3-methylpropyl)-N'-hydroxyureidylmethylpyridine-6-methylenoxy)-4-propoxy-5-methylsulfonylphenyl]-5-(3,4,5-trimethoxyphenyl)tetrahydrofuran, Trans-2-[2-N'-cyclopropylmethyl-N'-hydroxyureidylmethylpyridine-6-methylenoxy)-4-propoxy-5-methylsulfonylphenyl]-5-(3,4,5-trimethoxyphenyl)tetrahydrofuran, Trans-2-[2-(N'-n-butyl-N'-hydroxyureidylmethylpyridine-6-methylenoxy)-4-propoxy-5-methylsulfonylphenyl]-5-(3,4,5-trimethoxyphenyl)tetrahydrofuran, Trans-2-[2-(N'-n-butyl-N'-hydroxyureidylmethylpyridine-6-methylenoxy)-4-propoxy-5-methylsulfonylphenyl]-5-(3,4,5-trimethoxyphenyl)tetrahydrofuran hydrochloride salt, Trans-2-[2-(N'-benzyl)-N'-hydroxyureidylmethylpyridine-6-methylenoxy)-4-propoxy-5-methylsulfonylphenyl]-5-(3,4,5-trimethoxyphenyl)tetrahydrofuran, Trans-2-[2-(N'-alkyl-N'-hydroxyureidylmethylfuran-5-methylenoxy)-4-propoxy-5-methylsulfonylphenyl]-5-(3,4,5-trimethoxyphenyl)tetrahydrofuran, Trans-2-[2-(N'-(3-alkyl)-N'-hydroxyureidylmethylpyridine-6-methylenoxy)-4-propoxy-5-methylsulfonylphenyl]-5-(3,4,5-trimethoxyphenyl)tetrahydrofuran, and Trans-2-[2-(N'-hydroxyureidylmethylfuran-5-methylenoxy)-4-propoxy-5-methylsulfonylphenyl]-5-(3,4,5-trimethoxyphenyl)tetrahydrofuran.

BIOLOGICAL ACTIVITY EXAMPLES

EXAMPLE 14

Ability of Compound to Bind to PAF Receptors a) Preparation of Human Platelet Membranes:

Human platelet membranes were prepared from platelet concentrates obtained from the American Red Cross Blood Services (Dedham, Mass.). After several washes with platelet wash solution (150 mM NaCl, 10 mM Tris, and 2 mM EDTA, pH 7.5), the platelet pellets were resuspended in 5 mM MgCl$_2$, 10 mM Tris, and 2 mM EDTA at pH 7.0. The cells were then quickly frozen with liquid nitrogen and thawed slowly at room temperature. The freezing and thawing procedure was repeated at least three times. For further fractionation of membrane fragments, the lysed membrane suspension was layered over the top of a discontinuous sucrose density gradient of 0.25, 1.03, and 1.5 M sucrose prepared in 10 mM MgCl$_2$, 10 mM Tris and 2 mM EDTA, pH 7.0, and centrifuged at 63, 500×g for 2 hours. The membrane fractions banding between 0.25 and 1.03 M (membrane A) and between 1.03 and 1.5 M (membrane B) were collected separately. The protein concentration of the membrane preparations was determined by Lowry's method with bovine serum albumin (BSA) as the standard. The membranes were then separated into smaller fractions (4 ml each) and stored at −80° C. and thawed before use.

b) [$^3$H]PAF Binding Inhibition:

The ability of [$^3$H]PAF to bind to specific receptors on human platelet membranes was evaluated at optimal conditions at pH 7.0 and in the presence of 10 mM MgCl$_2$. Membrane protein (100 µg) was added to a final 0.5 mL solution containing 0.15 pmol (0.3 nM concentration) of [$^3$H]PAF and a known amount of unlabeled PAF or PAF receptor antagonist in 10 mM MgCl$_2$, 10 mM Tris and 0.25% BSA at pH 7.0. After incubation for four hours at 0° C., the bound and unbound [$^3$H]PAF were separated through a Whatman GF/C glass fiber filter under vacuum. No degradation of filter bound [$^3$H]PAF has been detected under this assay condition. The nonspecific binding was defined as the total binding in the presence of excess unlabeled PAF (1 mM) where no further displacement was found with higher concentrations of either unlabeled PAF or PAF analogs or PAF receptor antagonists. The specific binding was defined as the difference between total binding and nonspecific binding.

To determine the relative potency of tested compounds, [$^3$]PAF binding in the presence of inhibitors was normalized in terms of percent inhibition by assigning the total binding in the absence of inhibitors as 0% inhibition and the total binding in the presence of 1 mM unlabeled PAF as 100%. The percent inhibition by the compound can be calculated by the formula expressed below:

% inhibition [(Total binding-total binding in the presence of compound)/nonspecific binding]×100%

The $IC_{50}$ was calculated as the concentration of the inhibitor necessary to obtain 50% inhibition of the specific [$^3$]PAF binding and was calculated by a nonlinear regression computer software program, GraphPad Inplot, version 3.0 (GraphPad software, San Diego, Calif.).

EXAMPLE 15
Effect of Compound on PAP-induced Hemoconcentration a) Animals

Female CD-1 mice, weighing 16–20 grams, were obtained from Charles River Laboratory (Wilmington, Mass.). Tap water and rodent laboratory chow (5001, Purina Mills, St. Louis, Mo.) were provided ad libitum. The mice were housed for an average of four days prior to use.

b) Hematocrit measurement

PAF (1-0-alkyl-2-acetyl-sn-glyceryl-3-phosphorylcholine, Sigma Chemical Co.) was dissolved in 0.25% bovine serum albumin (BSA) in 0.9% NaCl solution. Except for dose-response studies, 10,pg (10 ml/kg) of PAF solution was injected into the tail vein. All test compounds were dissolved in 0.5% DMSO/saline solution and intravenously injected at 3 mg/kg body weight 15 minutes prior to PAF challenge. Thirty to fifty μL blood was collected by cutting the tail end into a heparinized micro-hematocrit tube (O.D. 1.50 mm) 15 minutes after PAF administration.

All test compounds were given intravenously at 3 mg/kg 15 minutes before PAF (10 μg/kg, intravenously) or AA (0.5 mg/ear) in mice.

EXAMPLE 16
Effect of 2, 5-Diaryl Tetrahydrothiophones and Tetrahydrofurans on Endotoxin-induced Kouse Mortality a) Animals The mice are obtained and treated as in Example 15 above.

b) Mortality Measurement

Endotoxin (*E. coli* serotype 0127:B8) and lipopolysaccharide (Sigma Chemical Co., St. Louis, Mo.) were freshly dissolved in 0.9% NaCl solution. Except for dose-response studies, endotoxin at 50 mg/kg was injected into the tail vein. All test compounds were dissolved in 0.5% DMSO saline solution and intravenously injected at 3 mg/kg body weight 15 minutes prior to PAF challenge. Death occurred typically within 12–36 hours. Mortality was recorded 48 hours after endotoxin challenge, as death rarely occurred after 48 hours.

EXAMPLE 17
Effect of Compounds on Cytosol 5-Lipoxygenass of Rat Basophile Leukemia Cells a) Enzyme preparation Washed rat RBL cells (4×10$^8$) were suspended in 20 mL of 50 M potassium phosphate buffer at pH 7.4 containing 10% ethylene glycol/1 mM EDTA (Buffer A). The cell suspension was sonicated at 20 KHz for 30 seconds, and the sonicate was centrifuged at 10,000× g for 10 minutes, followed by further centrifugation at 105,000× g for 1 hour. The supernatant solution (cytosol fraction) containing 5-lipoxygenase is stored at −70° C. Protein concentration is determined according to the procedure of Bradford (Bradford Dye Reagent) with bovine serum albumin as a standard.

b) Enzyme assay

For routine assay of 5-LO the mixture contains 50 mM potassium phosphate buffer at pH 7.4, 2 mM $CaCl_2$, 2 mM ATP, 25 M arachidonic acid (0.1 Ci) and enzyme (50–100 mg of protein) in a final volume of 200 L. The reaction is carried out at 24° C. for 3 minutes. The mixture is extracted with 0.2 mL of an ice-cold mixture of ethyl ether:methanol: 0.2 M citric acid (30:4:1). The extract is subjected to thin-layer chromatography at −10° C. in a solvent system of petroleum ether:ethyl ether:acetic acid (15:85:0.1). The silica gel zones corresponding to authentic arachidonic acid, and its metabolites are scraped into scintillation vials for counting. The enzyme activity is expressed in terms of the amount of arachidonic acid oxygenated for 3 minutes.

Modifications and variations of the present invention relating to compounds that reduce the formation of oxygen radicals during an inflammatory or immune response will be obvious to those skilled in the art from the foregoing detailed description of the invention. Such modifications and variations are intended to come within the scope of the appended claims.

What is claimed is:

1. A compound having the following structure:

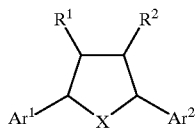

wherein:

$Ar^1$ is either

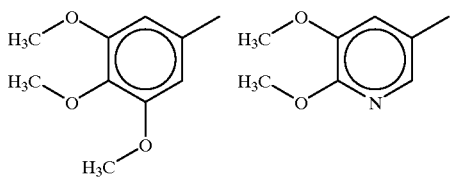

$Ar^2$ is

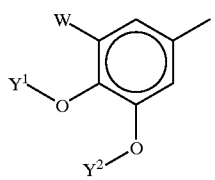

and wherein:

W is methyl sulfonyl;

X is O, S, S(O), $CR^5$;

$Y^1$, $Y^2$ are independently selected from the group consisting of:
(a) hydrogen;
(b) lower alkyl, lower alkoxy, lower alkenyl, lower alkynyl, alkylaryl;
(c) —AN(OM)C(O)N($R^3$)$R^4$, —AN($R^3$)C(O)N(OM)$R^4$, —AN(OM)C(O)$R^4$, —AC(O)N(OM)$R^4$, —AN($R^3$)C(O)N(OM)$R^4$, —C(O)N(OM)$R^4$, and —C(O)NH$R^3$;

wherein A is selected from the group consisting of substituted or unsubstituted lower alkyl, lower alkyl-alkoxy, -lower alkyl-heteroaromatic-lower alkyl, lower alkenyl, lower alkynyl, alkaryl or aralkyl;
M is selected from hydrogen, a pharmaceutically acceptable cation, and a metabolically cleavable leaving group;
$R^1$ and $R^2$ are independently selected from hydrogen, lower alkyl, $C_{3-8}$ cycloalkyl, halo lower alkyl, halo, —COOH;
$R^3$ and $R^4$ are independently selected from the group consisting of hydrogen, substituted or unsubstituted alkyl, substituted or unsubstituted alkyl where one or more carbon atoms are replaced by S, N, or O, substituted or unsubstituted cycloalkyl of from 3 to 8 carbon atoms, where one or more carbons are replaced by S, N, or O, alkenyl, alkynyl, aryl, aralkyl, alkaryl, $C_{1-6}$alkoxy-$C_{1-10}$alkyl, $C_{1-6}$alkylthio-$C_{1-10}$alkyl, $C_{1-6}$hydroxy-$C_{1-6}$alkyl, $C_{1-6}$carbonyl-$C_{1-6}$alkyl, $C_{1-6}$amino-$C_{1-6}$alkyl;
$R^5$ is selected from the group consisting of:
(a) hydrogen;
(b) lower alkyl lower alkenyl, lower alkynyl, alkaryl;
(c) —AN(OM)C(O)N($R^3$)$R^4$, —AN(R)C(O)N(OM)$R^4$, —AN(OM)C(O)$R^4$, —AC(O)N(OM)$R^4$, —AS(O)$_n R^3$, —AS(O)$_n$CH$_2$C(O)$R^3$, —AS(O)$_n$CH$_2$CH(OH)$R^3$, —AC(O)NH$R^3$;
wherein each n is independently 0, 1 or 2; A is selected from the group consisting of substituted or unsubstituted lower alkyl, lower alkyl-alkoxy, lower alkenyl, lower alkynyl, alkaryl and aralkyl; M is selected from hydrogen, a pharmaceutically acceptable cation, or a metabolically cleavable leaving group.

2. A compound having the following structure:

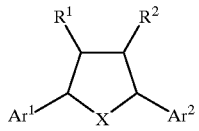

wherein:
$Ar^1$ is either

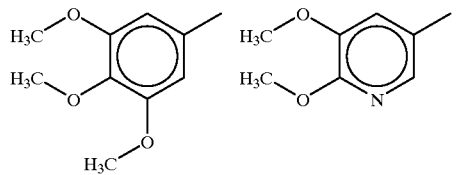

$Ar^2$ is

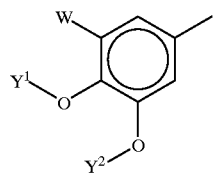

and wherein:
W is independently selected from the group consisting of:
—AN(OM)C(O)N($R^3$)$R^4$, —AN($R^3$)C(O)N(OM)$R^4$, —AN(OM)C(O)$R^4$, —AC(O)N(OM)$R^4$, —N(OM)C(O)N($R^3$)$R^4$, —N($R^3$)C(O)N(OM)$R^4$, —N(OM)C(O)$R^4$, —C(O)N(OM)$R^4$, —S(O)$_n R^3$, —S(O)$_4$CH$_2$C(O)A, —S(O)$_4$CH$_2$CH(OH)A, and —C(O)NHA,
X is O, S, S(O), CR$^5$;
$Y^1$, $Y^2$ are independently selected from the group consisting of:
(a) hydrogen;
(b) lower alkyl, lower alkoxy, lower alkenyl, lower alkynyl, alkylaryl;
(c) —AN(OM)C(O)N($R^3$)$R^4$, —AN($R^3$)C(O)N(OM)$R^4$, —AN(OM)C(O)$R^4$, —AC(O)N(OM)$R^4$, —AN($R^3$)C(O)N(OM)$R^4$, —C(O)N(OM)$R^4$, and —C(O)NH$R^3$;
wherein A is -lower alkyl-furan-lower alkyl;
M is selected from hydrogen, a pharmaceutically acceptable cation, and a metabolically cleavable leaving group;
$R^1$ and $R^2$ are independently selected from hydrogen, lower alkyl, $C_{3-8}$cycloalkyl, halo lower alkyl, halo, —COOH;
$R^3$ and $R^4$ are independently selected from the group consisting of hydrogen, substituted or unsubstituted alkyl, substituted or unsubstituted alkyl where one or more carbon atoms are replaced by S, N, or O, substituted or unsubstituted cycloalkyl of from 3 to 8 carbon atoms, where one or more carbons are replaced by S, N, or O alkenyl, alkynyl, aryl, aralkyl, alkaryl, $C_{1-6}$alkoxy-$C_{1-10}$alkyl, $C_{1-6}$alkylthio-$C_{1-10}$alkyl, $C_{1-6}$hydroxy-$C_{1-6}$alkyl, $C_{1-6}$carbonyl-$C_{1-6}$alkyl, $C_{1-6}$amino-$C_{1-6}$alkyl;
$R^5$ is selected from the group consisting of:
(a) hydrogen;
(b) lower alkyl lower alkenyl, lower alkynyl, alkaryl;
(c) —AN(OM)C(O)N($R^3$)$R^4$, —AN($R^3$)C(O)N(OM)$R^4$, —AN(OM)C(O)$R^4$, —AC(O)N(OM)$R^4$, —AS(O)$_n R^3$—AS(O)$_n$CH$_2$C(O)$R^3$, —AS(O)$_n$CH$_2$CH(OH)$R^3$, —AC(O)NH$R^3$;
wherein each n is independently 0, 1 or 2; A is selected from the group consisting of substituted or unsubstituted lower alkyl, lower alkyl-alkoxy, lower alkenyl, lower alkynyl, alkaryl and aralkyl; M is selected from hydrogen, a pharmaceutically acceptable cation, or a metabolically cleavable leaving group.

3. A compound having the following structure:

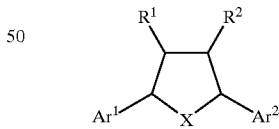

wherein:
$Ar^1$ is either

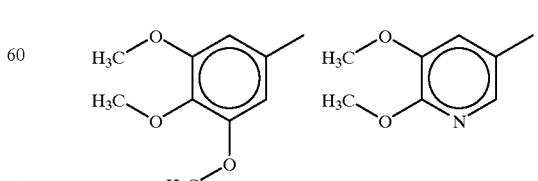

Ar² is

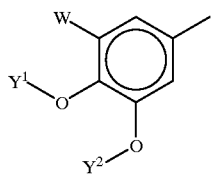

and wherein:

W is independently selected from the group consisting of:
—AN(OM)C(O)N(R³)R⁴, —AN(R³)C(O)N(OM)R⁴, —AN(OM)C(O)R⁴, —AC(O)N(OM)R⁴, —N(OM)C(O)N(R³)R⁴, —N(R³)C(O)N(OM)R⁴, —N(OM)C(O)R⁴, —C(O)N(OM)R⁴, —S(O)$_n$R³, —S(O)$_4$CH$_2$C(O)A, —S(O)$_4$CH$_2$CH(OH)A, and —C(O)NHA, X is O, S, S(O), CR⁵;

Y¹, Y² are independently selected from the group consisting of:
(a) hydrogen;
(b) lower alkyl, lower alkoxy, lower alkenyl, lower alkynyl, alkylaryl;
(c) —AN(OM)C(O)N(R³)R⁴, —AN(R³)C(O)N(OM)R⁴, —AN(OM)C(O)R⁴, —AC(O)N(OM)R⁴, —AN(R³)C(O)N(OM)R⁴, —C(O)N(OM)R⁴, and —C(O)NHR³;

wherein A is -lower alkyl-pyridine-lower alkyl;

M is selected from hydrogen, a pharmaceutically acceptable cation, and a metabolically cleavable leaving group;

R¹ and R² are independently selected from hydrogen, lower alkyl, C$_{3-8}$ cycloalkyl, halo lower alkyl, halo, —COOH;

R³ and R⁴ are independently selected from the group consisting of hydrogen, substituted or unsubstituted alkyl, substituted or unsubstituted alkyl, where one or more carbon atoms are replaced by S, N, or O, substituted or unsubstituted cycloalkyl of from 3 to 8 carbon atoms, where one or more carbons are replaced by S, N, or O, alkenyl, alkynyl, aryl, aralkyl, alkaryl, C$_{1-6}$alkoxy-C$_{1-10}$alkyl, C$_{1-6}$alkylthio-C$_{1-10}$alkyl, C$_{1-6}$hydroxy-C$_{1-6}$alkyl, C$_{1-6}$carbonyl-C$_{1-6}$alkyl, C$_{1-6}$amino-C$_{1-6}$alkyl;

R⁵ is selected from the group consisting of:
(a) hydrogen;
(b) lower alkyl lower alkenyl, lower alkynyl, alkaryl;
(c) —AN(OM)C(O)N(R³)R⁴, —AN(R³)C(O)N(OM)R⁴, —AN(OM)C(O)R⁴, —AC(O)N(OM)R⁴, —AS(O)$_n$R³, —AS(O)$_n$CH$_2$C(O)R³, —AS(O)$_n$CH$_2$CH(OH)R³, —AC(O)NHR³;

wherein each n is independently 0, 1 or 2; A is selected from the group consisting of substituted or unsubstituted lower alkyl, lower alkyl-alkoxy, lower alkenyl, lower alkynyl, alkaryl and aralkyl; M is selected from hydrogen, a pharmaceutically acceptable cation, or a metabolically cleavable leaving group.

4. A compound having the following structure:

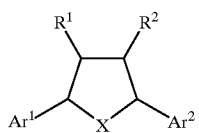

wherein:

Ar¹ is either

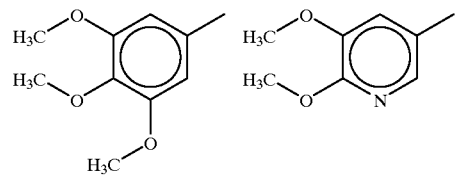

Ar² is

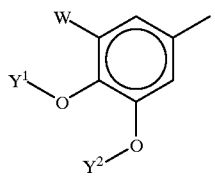

and wherein:

W is independently selected from the group consisting of:
—AN(OM)C(O)N(R³)R⁴, —AN(R³)C(O)N(OM)R⁴, —AN(OM)C(O)R⁴, —AC(O)N(OM)R⁴, —N(OM)C(O)N(R³)R⁴, —N(R³)C(O)N(OM)R⁴, —N(OM)C(O)R⁴, —C(O)N(OM)R⁴, —S(O)$_n$R³, —S(O)$_4$CH$_2$C(O)A, —S(O)$_4$CH$_2$CH(OH)A, and —C(O)NHA, Y¹ is independently selected from the group consisting of:
(a) hydrogen;
(b) lower alkyl, lower alkoxy, lower alkenyl, lower alkynyl, alkylaryl;
(c) —AN(OM)C(O)N(R³)R⁴, —AN(R³)C(O)N(OM)R⁴, —AN(OM)C(O)R⁴, —AC(O)N(OM)R⁴, —AN(R³)C(O)N(OM)R⁴, —C(O)N(OM)R⁴, and —C(O)NHR³;

wherein A is selected from the group consisting of substituted or unsubstituted lower alkyl, lower alkyl-alkoxy, -lower alkyl-heteroaromatic-lower alkyl, lower alkenyl, lower alkynyl, alkaryl or aralkyl;

M is selected from hydrogen, a pharmaceutically acceptable cation, and a metabolically cleavable leaving group;

R³ and R⁴ are independently selected from the group consisting of hydrogen, substituted or unsubstituted alkyl, substituted or unsubstituted alkyl where one or more carbon atoms are replaced by S, N, or O, substituted or unsubstituted cycloalkyl of from 3 to 8 carbon atoms, where one or more carbons are replaced by S, N, or O, alkenyl, alkynyl, aryl, aralkyl, alkaryl, C$_{1-6}$alkoxy-C$_{1-10}$alkyl, C$_{1-6}$alkylthio-C$_{1-10}$alkyl, C$_{1-6}$hydroxy-C$_{1-6}$alkyl, C$_{1-6}$carbonyl-C$_{1-6}$alkyl, C$_{1-6}$amino-C$_{1-6}$alkyl;

wherein each n is independently 0, 1 or 2.

5. The compound of claim 4 having the structure:

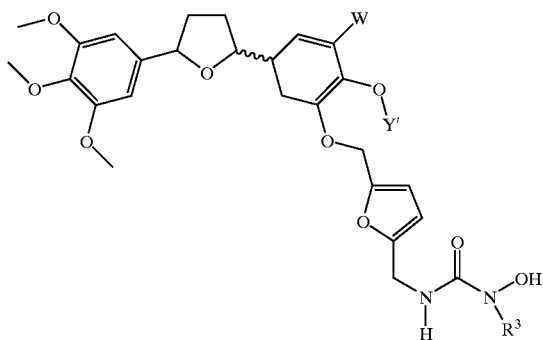

6. The compound of claim 4 having the structure:

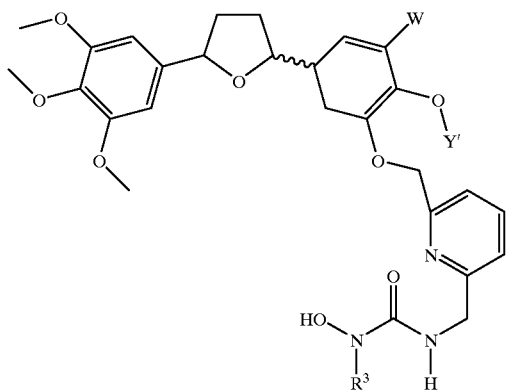

7. A pharmaceutical composition comprising a pharmaceutically active carrier and a therapeutically effective amount of a compound of claim 1, 2, 3, 4, 5 or 6.

8. A method for the treatment of a disorder mediated by platelet activating factor or products of 5-lipoxygenase in an animal, comprising administering to an animal in need of such treatment, an amount effective to reduce formation of oxygen radicals in vivo, of a compound of claim 1, 2, 3, 4, 5 or 6.

9. The method of claim 8, wherein the animal is a mammal selected from the group consisting of human, equine, canine and bovine.

10. The method of claim 8, wherein the disorders mediated by platelet activating factor or products of 5-lipoxygenase are selected from the group consisting of arthritis, acute inflammation, asthma, endotoxic shock, pain, psoriasis, ophthalmic inflammation, ischemia, gastrointestinal ulceration, myocardial infarction, inflammatory bowel diseases, and acute respiratory distress syndrome.

11. A method for the treatment of a disorder that is arthritis, acute inflammation, asthma, endotoxic shock, pain, psoriasis, ophthalmic inflammation, ischemia, gastrointestinal ulceration, myocardial infarction, an inflammatory bowel disease, or acute respiratory distress syndrome, comprising administering to an animal suffering from or susceptible such disorder an effective amount of a compound of claim 1, 2, 3, 4, 5 or 6.

* * * * *